United States Patent
Klar et al.

(10) Patent No.: US 9,156,877 B2
(45) Date of Patent: Oct. 13, 2015

(54) 17-HYDROXY-17-PENTAFLUORETHYL-ESTRA-4,9(10)-DIEN-11-BENZYLIDENE DERIVATIVES, METHODS FOR THE PRODUCTION THEREOF AND USE THEREOF FOR TREATING DISEASES

(75) Inventors: Ulrich Klar, Berlin (DE); Wolfgang Schwede, Glienicke (DE); Carsten Möller, Berlin (DE); Andrea Rotgeri, Berlin (DE); Wilhelm Bone, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 678 days.

(21) Appl. No.: 13/386,031

(22) PCT Filed: Jul. 7, 2010

(86) PCT No.: PCT/EP2010/004150
§ 371 (c)(1),
(2), (4) Date: Aug. 28, 2012

(87) PCT Pub. No.: WO2011/009532
PCT Pub. Date: Jan. 27, 2011

(65) Prior Publication Data
US 2012/0316145 A1   Dec. 13, 2012

(30) Foreign Application Priority Data
Jul. 20, 2009   (DE) .................. 10 2009 034 367

(51) Int. Cl.
| A61K 31/58 | (2006.01) |
| A61K 31/567 | (2006.01) |
| C07J 1/00 | (2006.01) |
| C07J 21/00 | (2006.01) |
| C07J 41/00 | (2006.01) |
| C07J 43/00 | (2006.01) |

(52) U.S. Cl.
CPC ............. *C07J 1/0033* (2013.01); *C07J 1/0085* (2013.01); *C07J 21/006* (2013.01); *C07J 41/0094* (2013.01); *C07J 43/003* (2013.01)

(58) Field of Classification Search
CPC .... C07J 1/0085; C07J 21/006; C07J 41/0094; C07J 43/003; A61K 31/567; A61K 31/58
USPC .................................. 552/648; 514/176, 179
See application file for complete search history.

(56) References Cited

U.S. PATENT DOCUMENTS

| 4,386,085 A | 5/1983 | Teutsch et al. |
| 4,609,651 A | 9/1986 | Rohde et al. |
| 4,634,695 A | 1/1987 | Torelli et al. |
| 4,900,725 A | 2/1990 | Nioue et al. |
| 4,921,846 A | 5/1990 | Nedelec et al. |
| 4,954,490 A | 9/1990 | Cook et al. |
| 5,073,548 A | 12/1991 | Cook et al. |
| 5,108,996 A | 4/1992 | Claussner et al. |
| 5,272,140 A | 12/1993 | Loozen |
| 5,407,928 A | 4/1995 | Kasch et al. |
| 5,576,310 A | 11/1996 | Schubert et al. |
| 5,693,628 A | 12/1997 | Schubert et al. |
| 5,712,264 A | 1/1998 | Hamersma et al. |
| 5,739,125 A | 4/1998 | Kasch et al. |
| 5,986,115 A | 11/1999 | Bohlmann et al. |
| 6,020,328 A | 2/2000 | Cook et al. |
| 6,043,234 A | 3/2000 | Stöckemann et al. |
| 6,225,298 B1 | 5/2001 | Spicer et al. |
| 6,316,432 B1 | 11/2001 | Schwede et al. |
| 6,476,079 B1 | 11/2002 | Jukarainen et al. |
| 6,503,895 B2 | 1/2003 | Schwede et al. |
| 6,806,263 B2 | 10/2004 | Schwede et al. |

(Continued)

FOREIGN PATENT DOCUMENTS

| CA | 2 280 041 | 8/1998 |
| EP | 0057115 A2 | 4/1982 |

(Continued)

OTHER PUBLICATIONS

Bagaria, et al.,"Low-dose Mifepristone in Treatment of Uterine Leiomyoma: A Randomized Double-blind Placebo-controlled Clinical Trial," Australian and New Zealand Journal of Obstetrics and Gynaecology, 2009, 49:77-83.
Bohl, et al.,"Molecular Mechanics and X-ray Crystal Structure Investigations in Conformations of 11β Substituted 4,9-dien-3-one Steroids," J. Mol. Graphics, Sep. 1989, 7:122-153.
Braga, et al.,"Crystal Polymorphism: Challenges at the Crossroads of Science and Technology," Making Crystals by Design, 2007, pp. 293-314.
Braja, et al., "Mifepristone [RU-486], the recently developed antiprogesterone drug and its analogues," J. Indian Inst. Sci., Jun. 29, 1999, 81:2870289.
Cabri, et al.,"Polymorphisms and Patent, Market, and Legal Battles: Cefdinir Case Study," Organic Process Research & Development, 2007, 11(1):64-72.
Caira,"Crystalline Polymorphism of Organic Compounds," Topics in Current Chemistry, 1998, 198: 164-208.
Chwalisz, et al.,"A Randomized, Controlled Trial of Asoprisnil, a Novel Selective Progesterone Receptor Modulator, in Women with Uterine Leiomyomata," Fertility and Sterility, Jun. 2007, 87(6):1399-1412.
Davey,"Solvent Effects in Crystallisation Processes," CurrentTopics in Material Science, 1982,8: 429-479.
English Transl. of Office Action for European Appl. No. 06 090 095 dated Jan. 16, 2007 (7,910,573 B2).

(Continued)

*Primary Examiner* — Barbara P Badio
(74) *Attorney, Agent, or Firm* — Karen B. King; Thomas C. Blankinship

(57) ABSTRACT

The invention relates to 17-hydroxy-17-pentafluoroethyl-estra-4,9(10)-diene 11-benzylidene derivatives of the formula I, in which Y and X are each as defined in the claims and the description, (I)

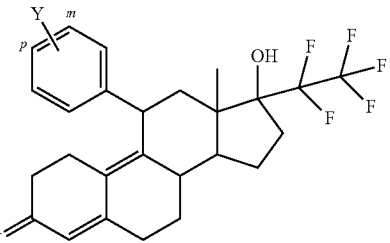

to a process for preparation thereof and to the use thereof as medicaments.

10 Claims, No Drawings

(56) References Cited

U.S. PATENT DOCUMENTS

| | | | |
|---|---|---|---|
| 6,825,182 B2 * | 11/2004 | Ring et al. .................. 514/179 |
| 6,861,415 B2 | 3/2005 | Kim et al. |
| 7,087,591 B2 | 8/2006 | Kim et al. |
| 7,148,213 B2 | 12/2006 | Schwede et al. |
| 7,192,942 B2 | 3/2007 | Grawe et al. |
| 7,550,451 B2 | 6/2009 | Hillisch et al. |
| 7,799,770 B2 | 9/2010 | Grawe et al. |
| 7,910,573 B2 | 3/2011 | Beckmann et al. |
| 8,053,426 B2 | 11/2011 | Fuhrmann et al. |
| 2001/0016578 A1 | 8/2001 | Spicer et al. |
| 2002/0045774 A1 | 4/2002 | Schwede et al. |
| 2002/0143000 A1 | 10/2002 | Hegele-Hartung et al. |
| 2003/0069434 A1 | 4/2003 | Bohlmann et al. |
| 2003/0191099 A1 | 10/2003 | Bohlmann et al. |
| 2004/0006241 A1 | 1/2004 | Grawe et al. |
| 2004/0048841 A1 | 3/2004 | Hoffmann et al. |
| 2004/0157811 A1 | 8/2004 | Lichtner et al. |
| 2005/0080060 A1 | 4/2005 | Schwede et al. |
| 2005/0277769 A1 | 12/2005 | Burton et al. |
| 2007/0105828 A1 | 5/2007 | Joshi et al. |
| 2009/0075989 A1 | 3/2009 | Schwede et al. |
| 2011/0112057 A1 | 5/2011 | Fuhrmann et al. |
| 2012/0149670 A1 | 6/2012 | Schwede et al. |
| 2012/0184515 A1 | 7/2012 | Klar et al. |
| 2012/0190660 A1 | 7/2012 | Klar et al. |
| 2012/0232042 A1 | 9/2012 | Klar et al. |
| 2012/0258941 A1 | 10/2012 | Klar et al. |
| 2013/0005697 A1 | 1/2013 | Schwede et al. |
| 2013/0072464 A1 | 3/2013 | Schwede et al. |

FOREIGN PATENT DOCUMENTS

| | | | |
|---|---|---|---|
| EP | 0411733 | | 2/1991 |
| EP | 0676203 | | 10/1995 |
| EP | 0909764 | A1 | 4/1999 |
| EP | 0970103 | B1 | 4/2002 |
| EP | 1862468 | | 12/2007 |
| IN | 978MUM2005 | | 8/2005 |
| JP | H11171774 | | 6/1999 |
| WO | 9834947 | | 6/1985 |
| WO | 9603130 | A1 | 2/1996 |
| WO | 9615794 | | 5/1996 |
| WO | 9623503 | A1 | 8/1996 |
| WO | 9805679 | | 2/1998 |
| WO | 9807740 | | 2/1998 |
| WO | 9826783 | | 6/1998 |
| WO | 9933855 | | 7/1999 |
| WO | 9953924 | | 10/1999 |
| WO | 0147490 | A1 | 7/2001 |
| WO | 0232429 | A2 | 4/2002 |
| WO | 03045972 | A1 | 6/2003 |
| WO | 03093292 | | 11/2003 |
| WO | 2004014935 | A1 | 2/2004 |
| WO | 2006010097 | A2 | 1/2006 |
| WO | 2008058767 | A1 | 5/2008 |
| WO | 2009138186 | A2 | 11/2009 |
| ZA | 977482 | | 2/1998 |

OTHER PUBLICATIONS

Fuhrmann, et al.,"Synthesis and Biological Activity of a Novel, Highly Potent Progesterone Receptor Antagonist," J. Med. Chem., 2000, 43:5010-5016.

Hazra, et al.,"Mifepristone (RU-486), the Recently Developed Antiprogesterone Drug and its Analogues," J. Indian Inst. Sci, May-Jun. 2001, 81:287-298.

Kettel, et al.,"Treatment of Endometriosis with the Antiprogesterone Mifepristone (RU486)," Fertility and Sterility, Jan. 1996, 65(1):23-28.

Kettel, et al.,"Endocrine Responses to Long-term Administration of the Antiprogesterone RU486 in Patients with Pelvic Endometriosis," Fertility and Sterility, Sep. 1991, 56(3):402-407.

Kettel, et al.,"Preliminary Report on the Treatment of Endometriosis with Low-dose Mifepristone (RU 486)," Am. J. Obstst. Gynecol., Jun. 1998, 178(6):1151-1156.

Maibauer, et al.,"First Human Data for ZK 230211 (ZK-PRA), a New Progesterone Receptor Antagonist: A Phase I Clinical Analysis of Safety and Pharmacokinetics in Healthy Postmenopausal Woment," Abstracts—Poster Session IV, 2006, N. 4074:S196.

Möller, et al.,"Investigational Developments for the Treatment of Progesterone-dependent Diseases," Expert Opin. Investig. Drugs, 2008, 17(4):469-479.

Murphy, et al.,"Regresssion of Uterine Leiomyomata in Response to the Antiprogesterone RU 486," J. Clin. Endocrinol. Metab., 1993, 76(2):513-517.

Patani, et al.,"Bioisosterism: A Rational Approach in Drug Design," Chem. Rev., 1996, 96:3147-3176.

Steinauer, et al.,"Systematic Review of Mifepristone for the Treatment of Uterine Leiomyomata," Obstetrics & Gynecology, Jun. 2004, 103(6):1331-1336.

Tellekson, et al.,"Strategies for Attacking and Defending Pharmaceutical Patents: A Modern Take on "The Art of War"," Intellectual Property & Technology Law Journal, Dec. 2005, 17(12):5-14.

Van Geerestein, et al.,"Structure of the n-Butul Acetate Solvate of 11β-[4-(Dimethylamino)phelyl]-17β-hydroxy-17α-(1-propynyl)estra-4,9-dien-3-one," Acta Cryst., 1986, C42:1521-1523.

Vippagunta, et al.,"Crystalline Solids," Advanced Drug Delivery Reviews, 2001, 48:3-26.

English Language Translation of EP0411733, 1991.
English Language Translation of EP0676203, 1995.
English Language Translation of WO1998/026783, 1998.
English Language Translation of WO1999/053924, 1999.
English Language Abstract of JP H11171774 (corresponding to Japanese Patent Application No. 19970335723), 1999.

* cited by examiner

17-HYDROXY-17-PENTAFLUORETHYL-ESTRA-4,9(10)-DIEN-11-BENZYLIDENE DERIVATIVES, METHODS FOR THE PRODUCTION THEREOF AND USE THEREOF FOR TREATING DISEASES

The invention relates to the subject-matter described in the claims, i.e. novel 17-hydroxy-13-methyl-17-pentafluoroethyl-11-phenyldodecahydrocyclopenta[a]-phenanthren-3-one derivatives with progesterone-antagonizing action, to processes for preparation thereof, to the use thereof for treatment and/or prophylaxis of disorders and to the use thereof for production of medicaments for treatment and/or prophylaxis of disorders.

Compounds with antagonistic action on the progesterone receptor (competitive progesterone receptor antagonists) became known for the first time in 1982 (RU 486; EP 0 057 115) and have been described many times since then. Progesterone receptor antagonists with a fluorinated 17 side chain were described by U. Fuhrmann et al., J. Med. Chem. 43, 5010-5016 (2000) and have been published in WO 98/134947. A particularly active compound disclosed therein is 11-β-(4-acetylphenyl)-20,20,21,21,21-pentafluoro-17-hydroxynor-17-pregna-4,9-dien-3-one. However, compared to the structurally similar compounds of the present invention, this substance exhibits a relatively short in vivo half-life and additionally poor water solubility.

It is an object of the present invention to provide highly potent competitive progesterone receptor antagonists and hence alternative possible treatments of gynaecological disorders.

It has been found that the inventive compounds of the general formula (I) are particularly suitable for achieving this object.

The present invention relates to 17-hydroxy-17-pentafluoroethylestra-4,9(10)-diene 11-benzylidene derivatives of the general formula (I)

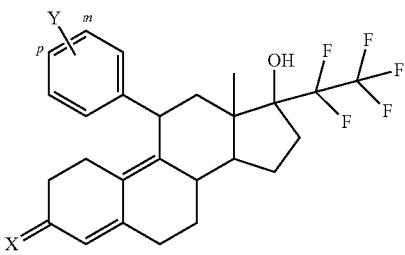

(I)

in which

Y is a —$CR^1$=$CHR^2$ or a —$CR^1$=$NR^3$ group, each of which is joined to the phenyl ring in the meta (m) or para (p) position, in which $R^1$ is hydrogen or a $C_1$-$C_{10}$-alkyl radical, $R^2$ is hydrogen, a $C_1$-$C_{10}$-alkyl, $C_2$-$C_{10}$-alkenyl, aryl, $C_7$-$C_{20}$-aralkyl, $C_1$-$C_{10}$-acyl, $CO_2R^4$, CN, CH=CH—$CO_2R^4$, $CH_2CH(CO_2R^4)_2$, $CH_2CH(CN)_2$ or a $CH_2NHCONHR^5$ radical and $R^3$ is a $C_1$-$C_{10}$-alkyl, O-alkyl, O—$(CH_2)_n$—$COOR^4$, O—$CH_2$-aryl, aryl, $C_7$-$C_{20}$-aralkyl or a $CH_2CO_2R^4$ radical in which $R^4$ is hydrogen or a $C_1$-$C_{10}$-alkyl group and $R^5$ is a $C_1$-$C_{10}$-alkyl, $C_2$-$C_{10}$-alkenyl, aryl, $C_7$-$C_{20}$-aralkyl, $(CH_2)_nCO_2R^4$ group where n=1 or 2 and $R^4$ is defined as specified, or is a

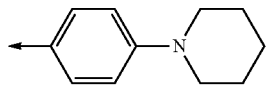

group and

X is oxygen, an $NOR^6$ or an $NNHSO_2R^6$ group, in which $R^6$ is hydrogen, a $C_1$-$C_{10}$-alkyl, aryl or $C_7$-$C_{20}$-aralkyl radical.

If $R^5$ is the arrow indicates the position of the bond to the amino group of the adjacent —$CH_2NHCONHR^5$ radical.

In a preferred embodiment of the invention, X is oxygen.

Preference is also given in accordance with the invention to the compounds of the formula (I) in which the substituent (radical) Y is bonded to the phenyl ring in the para position.

In the context of the present invention, the substituents, unless specified otherwise, are each defined as follows:

Alkyl in $R^1$, $R^2$, $R^3$, $R^4$, $R^5$ and $R^6$ and in other cases is understood to mean straight- or branched-chain alkyl groups with the specified number of carbon atoms or, as the case may be, 1-10 carbon atoms, for example methyl, ethyl, propyl, isopropyl, butyl, isobutyl, tert-butyl, pentyl, isopentyl, neopentyl, hexyl, heptyl, octyl, nonyl or decyl. The alkyl groups $R^1$, $R^2$, $R^3$, $R^4$, $R^5$ and $R^6$ may also be perfluorinated or substituted by 1-5 halogen atoms, hydroxyl groups, $C_1$-$C_4$-alkoxy groups, $C_6$-$C_{12}$-aryl groups (which may in turn be substituted by 1-3 halogen atoms). More particularly, alkyl may therefore also be hydroxymethylene (HO—$CH_2$), hydroxyethylene (HO—$C_2H_4$), hydroxypropylene (HO—$C_3H_6$) and hydroxybutylene (HO—$C_4H_8$) and the isomers thereof.

Alkenyl in $R^4$ and $R^5$ is understood to mean straight- or branched-chain alkenyl groups having 2-10 carbon atoms, for example vinyl, propenyl, butenyl, pentenyl, isobutenyl or isopentenyl.

The alkenyl groups $R^4$ and $R^5$ may be substituted by 1-5 halogen atoms, hydroxyl groups, $C_1$-$C_3$-alkoxy groups or $C_6$-$C_{12}$-aryl groups (which may in turn be substituted by 1-3 halogen atoms).

Aryl in $R^2$, $R^3$, $R^5$ and $R^6$ and in other cases is understood to mean substituted and unsubstituted carbocyclic or heterocyclic radicals with one or more heteroatoms, for example phenyl, naphthyl, furyl, thienyl, pyridyl, pyrazolyl, pyrimidinyl, oxazolyl, isoxazolyl, pyridazinyl, pyrazinyl, quinolyl, thiazolyl or tetrazolyl, which may be mono- or polysubstituted by halogen, OH, O-alkyl, S-alkyl, S(O)alkyl and $SO_2$ alkyl, $CO_2H$, $CO_2$-alkyl, $NH_2$, $NO_2$, $N_3$, CN, $C_1$-$C_{10}$-alkyl, $C_1$-$C_{10}$-acyl, $C_1$-$C_{10}$-acyloxy groups. If aryl is otherwise mentioned as a substituent on alkyl, alkenyl or alkynyl, it is especially aryl groups having 6-12 ring carbon atoms.

Aralkyl in $R^2$, $R^3$, $R^5$ and $R^6$ is understood to mean aralkyl groups which may contain up to 14 carbon atoms, preferably 6 to 10 carbon atoms, in the ring, and 1 to 8, preferably 1 to 4, carbon atoms in the alkyl chain. Useful aralkyl radicals include, for example, benzyl, phenylethyl, naphthylmethyl, naphthylethyl, furylmethyl, thienylethyl, pyridylpropyl. The rings may be mono- or polysubstituted by halogen, OH, O-alkyl, $CO_2H$, $CO_2$-alkyl, $NO_2$, $N_3$, CN, $C_1$-$C_{20}$-alkyl, $C_1$-$C_{20}$-acyl, $C_1$-$C_{20}$-acyloxy groups.

Possible heteroatoms include sulphur, oxygen or nitrogen, preference being given to nitrogen. One example is the pyridylpropyl radical.

Any mention of alkoxy (O-alkyl) refers to alkoxy groups having 1-4 carbon atoms. Alkoxy may especially be methoxy, ethoxy and propoxy.

Any mention of acyl (CO-alkyl) refers to acyl groups having 1-20 carbon atoms. Acyl may especially be formyl, acetyl, propionyl and butyryl.

Any mention of acyloxy (O—CO-alkyl) refers to acyloxy groups having 1-20 carbon atoms. Acyloxy may especially be formyloxy, acetyloxy, propionyloxy and butyryloxy.

Halogen is fluorine, chlorine or bromine. Among these, preference is given to fluorine and chlorine.

Depending on their structure, the inventive compounds of the general formula I can exist in stereoisomeric forms (enantiomers, diastereomers). The invention therefore also encompasses the enantiomers or diastereomers and the particular mixtures thereof, including the racemates. It is possible to isolate the stereoisomerically homogeneous constituents from such mixtures of enantiomers and/or diastereomers in a known manner.

Each of the said substituents on the steroid backbone may be either in an α position or in a β position. In addition, it is also possible for the substituents on the steroid backbone which contain a double bond and in which the double bond bears at least one non-hydrogen substituent on each atom to be present either in E or Z configuration.

When the inventive compounds can occur in tautomeric forms, the present invention encompasses all tautomeric forms.

The inventive compounds of the general formula I may also be present in the form of solvates, hydrates and salts, also including different crystal polymorphs, and α-, β- or γ-cyclodextrin clathrates, or compounds of the formula I encapsulated with liposomes.

Solvates in the context of the invention refer to those forms of the inventive compounds which, in the solid or liquid state, exhibit adduct formation with solvent molecules. If the derivatives of the formula I are in solvate form, the solvent present may be present in a stoichiometric or else non-stoichiometric ratio. In the case of stoichiometric solvates, these are also referred to as hemi-, (semi-), mono-, sesqui-, di-, tri-, tetra-, penta-, etc. solvates.

Hydrates are a specific form of the solvates in which the coordination is with water.

Among the solvates, preference is given to the hydrates, i.e. coordination compounds with water.

Preferred salts in the context of the present invention are physiologically compatible salts of the inventive compounds. Also included, however, are salts which are themselves unsuitable for pharmaceutical applications but can be used, for example, for the isolation or purification of the inventive compounds.

Physiologically compatible salts of the inventive compounds include—when a basic function is present—salts with inorganic or organic acids, especially of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid or benzoic acid.

Physiologically compatible salts of the inventive compounds include—when an acidic function is present—alkali metal salts, alkaline earth metal salts or ammonium salts, as obtainable by reaction with corresponding inorganic or organic bases. Preferred examples include alkali metal salts (e.g. sodium and potassium salts), alkaline earth metal salts (e.g. calcium and magnesium salts) and ammonium salts derived from ammonia or organic amines having 1 to 16 carbon atoms, preferred examples being ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methyl-glucamine, D-methylglucamine, ethylglucamine, 1,6-hexadiamine, glucosamine, N-methylglycine, 2-amino-1,3-propanediol, tris(hydroxymethyl)aminomethane or 1-amino-2,3,4-butanetriol.

Moreover, the present invention also encompasses prodrugs of the inventive compounds. The term "prodrugs" encompasses compounds which, during their time of residence in the body, are converted to inventive compounds, for example by enzymatic or hydrolytic processes.

The specific radical definitions given in the particular combinations or preferred combinations of radicals are, irrespective of the particular combinations of radicals specified, also replaced as desired by radical definitions of other combinations.

Very particular preference is given to combinations of two or more of the abovementioned preferred ranges.

It has been found that the inventive compounds of the formula (I), surprisingly, have good progesterone-antagonizing action, without having the disadvantages of the prior art compounds.

For instance, most inventive compounds have a surprisingly high metabolic stability in vitro in liver microsomes of rats and humans. At the same time, it has been possible to distinctly improve the water solubility for some compounds (see Example 60).

These compounds are valuable active pharmaceutical ingredients. They can be used, inter alia, for production of pharmaceutical formulations for treatment of fibroids of the uterus or of endometriosis, heavy menstrual bleeds, meningiomas, hormone-dependent breast cancers and complaints associated with the menopause, or for fertility control and emergency contraception.

For treatment of fibroids of the uterus or of endometriosis, the inventive compounds can be combined simultaneously or sequentially with gestagens or combinations of oestrogens and gestagens.

WO 96/15794 (Spicer et al., Balance Pharm. Inc.), WO 96/03130 (Stöckemann et al., Schering AG) and PCT/EP2009/003249 (Möller et al., Bayer Schering Pharma AG) disclose progesterone receptor antagonist/gestagen regimens. Fibroids of the uterus and endometriosis are very suitably treated by optionally repeating regimens in which the progesterone receptor antagonist is administered over a period of two to four months, followed by the administration of the gestagen over a period of one to four weeks. A particularly suitable administration is the optionally repeating 84-day administration of the progesterone receptor antagonist, followed by the 14-day administration of the gestagen.

For treatment of tumour disorders, it is possible, for example, to either simultaneously or sequentially administer the following active ingredients/active ingredient classes: SERMs, SERDs, antioestrogens, aromatase inhibitors, kinase inhibitors, angiogenesis inhibitors and/or cytostatics.

For treatment of fibroids of the uterus or of endometriosis, the inventive compounds can be combined simultaneously or sequentially with gestagens or combinations of oestrogens and gestagens.

For treatment of complaints associated with the menopause, one option is a simultaneous or sequential administration of the inventive compounds, for example, with SERMs, SERDs and oestrogens.

SERMs (Selective Estrogen Receptor Modulators) are, in accordance with the invention, those compounds which are tissue-selective and have either antioestrogenic or oestrogenic action, for example inhibit the action of oestrogen in the uterus, but have a neutral or oestrogen-like action in the bone. Examples are clomifene, raloxifene, tamoxifene, torimifene, bazedoxifene, lasofoxifene and ormeloxifene.

Selective oestrogen receptor destabilizers (SERDs) are medicaments which fully antagonize the oestrogen receptor and lead to degradation of the receptor.

Antioestrogens are compounds which fully antagonize the oestrogen receptor, for example fulvestrant.

Aromatase inhibitors inhibit the enzyme aromatase and hence the aromatization of androgens in oestrogens. These include anastrozole, letrozole, exemestane, vorozole, formestane and fadrozole.

Kinase inhibitors inhibit enzymes which transfer a phosphate residue from ATP to other substrates, and especially to hydroxyl groups therein, for example sorafenib (Nexavar) or imatinib (Gleevec).

Angiogenesis inhibitors, e.g. avastatin, reduce or block new vessel formation and hence the profusion of a tumour.

Cytostatics, e.g. cis-platin, taxol, Taxotere, sagopilone, ixabepilone, are natural or synthetic substances which drive tumour cells to apoptosis.

Gestagens in the context of the present invention are understood to mean either natural progesterone itself or synthetic derivatives which, like progesterone itself, bind to the progesterone receptor and inhibit ovulation in doses above the ovulation-inhibiting dose. Examples of synthetic derivatives include drospirenone, gestodene, levonorgestrel, cyproterone acetate, desogestrel and 3-ketodesogestrel, norethisterone, norethisterone acetate and dienogest.

Combinations of gestagens and oestrogens are active ingredient combinations present in the oral contraceptives known per se, for example Yasmin, Femovan, Triquilar, Marvelon, YAZ etc.

The inventive compounds can act systemically and/or locally. For this purpose, they can be administered in a suitable manner, for example by an oral, intrauterine, intravaginal, parenteral, pulmonary, nasal, sublingual, lingual, buccal, rectal, dermal, transdermal, conjunctival or otic route, or as an implant or stent.

"Intrauterine" means especially administration by means of an IUS (intrauterine system) or IUD (intrauterine device). One method of intravaginal administration is by means of an IVR (vaginal ring).

Intrauterine or intravaginal administration forms (cf., for example, WO 01/47490, especially page 1 line 10 to page 5 line 13 and page 7 line 19 to page 58 line 6, or for vaginal rings: WO 06/010097, especially page 10 line 22 to page 14 line 28) may comprise the inventive compounds and nonsilicone and/or silicone polymers, especially also siloxane-based elastomers (cf. WO 01/47490, especially page 7 line 19-page 15 line 15).

For these administration routes, the inventive compounds can be administered in suitable administration forms.

Suitable administration forms for oral administration are those which release the inventive compounds in a rapid and/or modified manner, work according to the prior art and contain the inventive compounds in crystalline and/or amorphous and/or dissolved form, for example tablets (uncoated or coated tablets, for example with enteric or retarded-dissolution or insoluble coatings which control the release of the inventive compound), tablets or films/wafers which disintegrate rapidly in the oral cavity, films/lyophilisates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardial, intraspinal or intralumbar route) or with inclusion of an absorption (for example by an intramuscular, subcutaneous, intracutaneous, percutaneous or intraperitoneal route). Suitable administration forms for parenteral administration include injection and infusion formulations in the form of solutions, suspensions, emulsions, lyophilisates or sterile powders.

For the other administration routes, suitable examples are inhalation medicaments (including powder inhalers, nebulizers), nasal drops, solutions or sprays; tablets for lingual, sublingual or buccal administration, films/wafers or capsules, suppositories, ear or eye preparations, vaginal capsules, aqueous suspensions (lotions, shaking mixtures), lipophilic suspensions, ointments, creams, transdermal therapeutic systems (for example patches), milk, pastes, foams, dusting powders, implants or stents.

The inventive compounds can be converted to the administration forms listed. This can be accomplished in a manner known per se by mixing with inert nontoxic pharmaceutically suitable excipients. These excipients include carriers (for example microcrystalline cellulose, lactose, mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and taste and/or odour correctors.

The present invention further provides medicaments which comprise at least one inventive compound, typically together with one or more inert nontoxic pharmaceutically suitable excipients, and for the use thereof for the aforementioned purposes.

In spite of this, it may be necessary to deviate from the amounts specified, specifically depending on body weight, administration route, individual behaviour towards the active ingredient, type of formulation, and time or interval of administration. For instance, less than the aforementioned minimum amount may be sufficient in some cases, while the upper limit mentioned has to be exceeded in other cases. In the case of administration of greater amounts, it may be advisable to divide them into several individual doses over the day.

The percentages in the tests and examples which follow are percentages by weight unless stated otherwise; parts are parts by weight. Solvent ratios, dilution ratios and concentration figures for liquid/liquid solutions are each based on volume.

The efficacy of the inventive compounds as progesterone receptor antagonists was demonstrated in vitro in transactivation tests and in vivo in rats (termination of early pregnancy).

Preference is given in accordance with the invention to the following compounds, the synthesis of which is described in the examples:

(8S,11R,13S,14S,17S)-17-hydroxy-13-methyl-17-pentafluoroethyl-11-(4-vinylphenyl)-1,2,6,7,8,11,12,13,14,15,16,17-dodecahydrocyclopenta[a]phenanthren-3-one (Example 1)

(8S,11R,13S,14S,17S)-17-hydroxy-11-[4-((E)-3-hydroxypropenyl)phenyl]-13-methyl-17-pentafluoroethyl-1,2,6,7,8,11,12,13,14,15,16,17-dodecahydrocyclopenta[a]phenanthren-3-one (Example 2)

(8S,11R,13S,14S,17S)-17-hydroxy-11-{4-[(E)-3-(4-methoxyphenyl)propenyl]phenyl}-13-methyl-17-pentafluoroethyl-1,2,6,7,8,11,12,13,14,15,16,17-dodecahydrocyclopenta[a]phenanthren-3-one (Example 3)

2-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}malonic acid dimethyl ester (Example 4)

2-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}malonic acid (Example 5)

(8S,11R,13S,14S,17S)-17-hydroxy-13-methyl-17-pentafluoroethyl-11-[4-((E)-2-pyridin-2-ylvinyl)phenyl]-1,2,6,7,8,11,12,13,14,15,16,17-dodecahydrocyclopenta[a]phenanthren-3-one (Example 6)

(8S,11R,13S,14S,17S)-17-hydroxy-13-methyl-17-pentafluoroethyl-11-[4-((E)-2-pyridin-3-ylvinyl)phenyl]-1,2,6,7,8,11,12,13,14,15,16,17-dodecahydrocyclopenta[a]phenanthren-3-one (Example 7)

(8S,11R,13S,14S,17S)-17-hydroxy-13-methyl-17-pentafluoroethyl-11-[4-((E)-2-pyridin-4-ylvinyl)phenyl]-1,2,6,7,8,11,12,13,14,15,16,17-dodecahydrocyclopenta[a]phenanthren-3-one (Example 8)

(8S,11R,13S,14S,17S)-17-hydroxy-13-methyl-11-{4-[(E)-2-(2-methylthiazol-4-yl)vinyl]phenyl}-17-pentafluoroethyl-1,2,6,7,8,11,12,13,14,15,16,17-dodecahydrocyclopenta[a]phenanthren-3-one (Example 9)

(8S,11R,13S,14S,17S)-17-hydroxy-13-methyl-11-{4-[(E)-2-(2-methylbenzothiazol-5-yl)vinyl]phenyl}-17-pentafluoroethyl-1,2,6,7,8,11,12,13,14,15,16,17-dodecahydrocyclopenta[a]phenanthren-3-one (Example 10)

(8S,11R,13S,14S,17S)-17-hydroxy-11-(4-isopropenylphenyl)-13-methyl-17-pentafluoroethyl-1,2,6,7,8,11,12,13,14,15,16,17-dodecahydrocyclopenta[a]phenanthren-3-one (Example 11)

(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]acrylic acid ethyl ester (Example 12)

(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]acrylic acid (Example 13)

(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]acrylonitrile (Example 14)

(2E,4E)-5-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]penta-2,4-dienoic acid ethyl ester (Example 15)

(8S,11R,13S,14S,17S)-17-hydroxy-13-methyl-11-[4-((E)-3-oxobut-1-enyl)phenyl]-17-pentafluoroethyl-1,2,6,7,8,11,12,13,14,15,16,17-dodecahydrocyclopenta[a]phenanthren-3-one (Example 16)

(2E,4E)-5-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]penta-2,4-dienoic acid (Example 17)

(8S,11R,13S,14S,17S)-11-[((E/Z)-4-buta-1,3-dienyl)phenyl]-17-hydroxy-13-methyl-17-pentafluoroethyl-1,2,6,7,8,11,12,13,14,15,16,17-dodecahydrocyclopenta[a]phenanthren-3-one (Example 18)

(8S,11R,13S,14S,17S)-17-hydroxy-13-methyl-17-pentafluoroethyl-11-(3-vinylphenyl)-1,2,6,7,8,11,12,13,14,15,16,17-dodecahydrocyclopenta[a]phenanthren-3-one (Example 19)

(8S,11R,13S,14S,17S)-17-hydroxy-11-(3-isopropenylphenyl)-13-methyl-17-pentafluoroethyl-1,2,6,7,8,11,12,13,14,15,16,17-dodecahydrocyclopenta[a]phenanthren-3-one (Example 20)

(8S,11R,13S,14S,17S)-17-hydroxy-13-methyl-17-pentafluoroethyl-11-[3-((E)-2-pyridin-2-ylvinyl)phenyl]-1,2,6,7,8,11,12,13,14,15,16,17-dodecahydrocyclopenta[a]phenanthren-3-one (Example 21)

(8S,11R,13S,14S,17S)-17-hydroxy-13-methyl-17-pentafluoroethyl-11-[3-((E)-2-pyridin-3-ylvinyl)phenyl]-1,2,6,7,8,11,12,13,14,15,16,17-dodecahydrocyclopenta[a]phenanthren-3-one (Example 22)

(8S,11R,13S,14S,17S)-17-hydroxy-13-methyl-17-pentafluoroethyl-11-[3-((E)-2-pyridin-4-ylvinyl)phenyl]-1,2,6,7,8,11,12,13,14,15,16,17-dodecahydrocyclopenta[a]phenanthren-3-one (Example 23)

(8S,11R,13S,14S,17S)-17-hydroxy-13-methyl-11-{3-[(E)-2-(2-methylthiazol-4-yl)vinyl]phenyl}-17-pentafluoroethyl-1,2,6,7,8,11,12,13,14,15,16,17-dodecahydrocyclopenta[a]phenanthren-3-one (Example 24)

(8S,11R,13S,14S,17S)-17-hydroxy-13-methyl-11-{3-[(E)-2-(2-methylbenzothiazol-5-yl)vinyl]phenyl}-17-pentafluoroethyl-1,2,6,7,8,11,12,13,14,15,16,17-dodecahydrocyclopenta[a]phenanthren-3-one (Example 25)

(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]acrylic acid ethyl ester (Example 26)

2-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}malononitrile (Example 27)

3-{(E)-2-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]vinyl}benzoic acid (Example 28)

4-{(E)-2-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]vinyl}benzoic acid (Example 29)

3-{(E)-2-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]vinyl}benzoic acid methyl ester (Example 30)

4-{(E)-2-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]vinyl}benzoic acid methyl ester (Example 31)

(8S,11R,13S,14S,17S)-17-hydroxy-11-{4-[(E)-2-(4-methanesulphonylphenyl)vinyl]phenyl}-13-methyl-17-pentafluoroethyl-1,2,6,7,8,11,12,13,14,15,16,17-dodecahydrocyclopenta[a]phenanthren-3-one (Example 32)

(8S,11R,13S,14S,17S)-17-hydroxy-13-methyl-11-{4-[(E)-2-(4-methylsulphanylphenyl)vinyl]phenyl}-17-pentafluoroethyl-1,2,6,7,8,11,12,13,14,15,16,17-dodecahydrocyclopenta[a]phenanthren-3-one (Example 33)

[1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]meth-(E)-ylideneaminooxy]acetic acid (Example 34)

4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzaldehyde O-benzyl oxime (Example 35)

4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzaldehyde O-ethyl oxime (Example 36)

4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzaldehyde O-(3,4-dichlorobenzyl)oxime (Example 37)

4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzaldehyde O-isobutyl oxime (Example 38)

1-ethyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea (Example 39)

1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]-3-isopropylurea (Example 40)

1-tert-butyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea (Example 41)

1-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}-3-phenylurea (Example 42)

1-(4-cyanophenyl)-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea (Example 43)

1-(4-fluorophenyl)-3-{(E)-3-[4-((8S,11R,13S,4S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea (Example 44)

1-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}-3-p-tolylurea (Example 45)

1-benzyl-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea (Example 46)

1-tert-butyl-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea (Example 47)

1-(3,5-dimethyl isoxazol-4-yl)-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea (Example 48)

3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)propionic acid ethyl ester (Example 49)

3-(3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)propionic acid (Example 50)

(3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)acetic acid ethyl ester (Example 51)

(3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)acetic acid (Example 52)

1-(4-chlorophenyl)-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea (Example 53)

1-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}-3-(4-methoxyphenyl)urea (Example 54)

4-(3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)benzoic acid ethyl ester (Example 55)

4-(3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)benzoic acid (Example 56)

1-allyl-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea (Example 57)

1-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}-3-(4-piperidin-1-ylphenyl)urea (Example 58)

The invention further relates to a process for preparing the inventive derivatives of the formula I. Such derivatives can be prepared as shown in Scheme 1, by converting an epoxide of the general formula II in which X' is an oxygen atom, two alkoxy groups $OR^7$, a $C_2$-$C_{10}$-alkylene-α,ω-dioxy group which may be straight-chain or branched, $R^7$ is $C_1$-$C_4$-alkyl, by organometallic coupling reactions, preferably by copper-catalysed Grignard reactions, to a compound of the general formula III in which $R^1$ and X' are each as defined above and $R^8$ is hydrogen, $R^9$ is a hydroxyl group, or $R^8$, $R^9$ together are a bond, and converting any functionalities present in $R^1$ and/or conducting further conversion reactions to give compounds of the general formula I' and optionally releasing the X group defined as oxygen from the X' group and/or producing a double bond ($R^8$, $R^9$ together are a bond) by elimination of water ($R^8$=hydrogen, $R^9$=hydroxyl group) and optionally further functionalizing the carbonyl group (X=oxygen) (X=$NOR^6$ or an $NNHSO_2R^6$ group).

Scheme 1

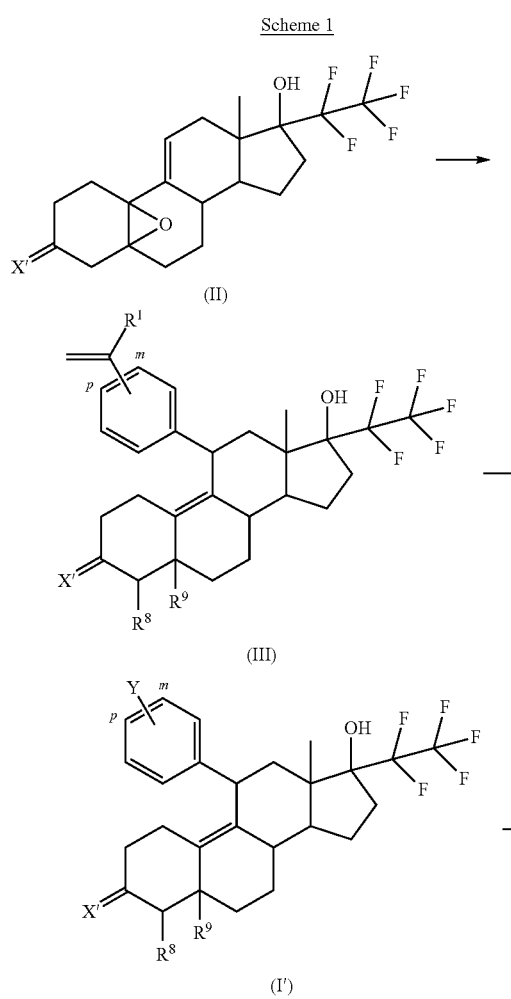

Typical details for the preparation of compounds of the general formula III can be found in Examples 1a, 1a, 19a and 20a.

If $R^8$ and $R^9$ together are a bond in the structure of the general formula I', this represents the three possible double bond isomers I'-A, I'-B and I'-C which can form in a wide variety of different ratios relative to one another during the reactions described.

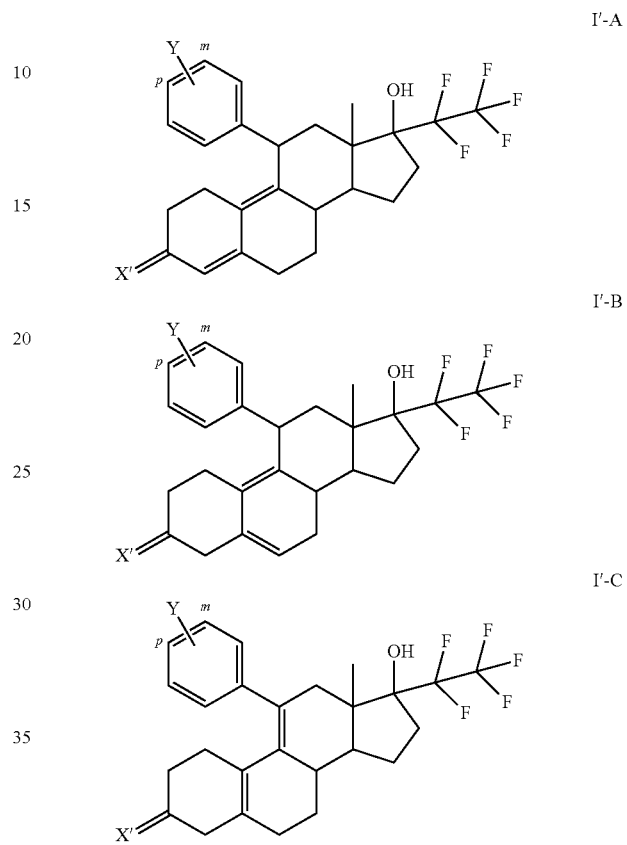

Some possible reaction sequences to give compounds of the general formula I' are shown by way of example in Scheme 2.

Scheme 2

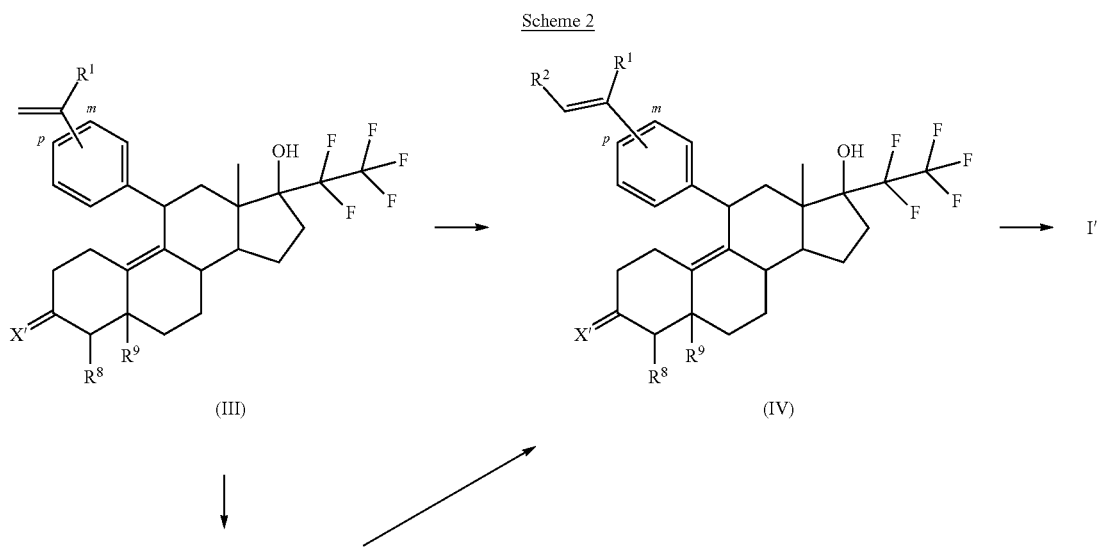

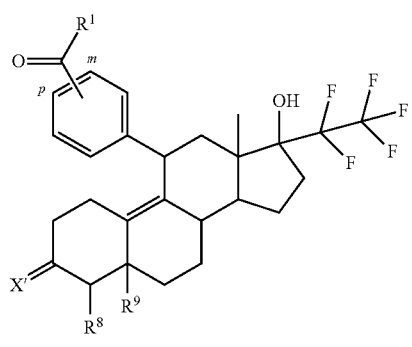

(V)

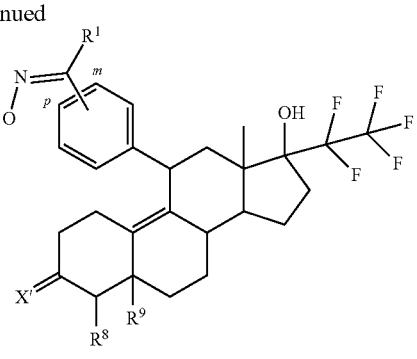

(VI)

Compounds of the general formula III are converted to compounds of the general formula IV by metal-catalysed coupling reactions with olefins by the methods known to those skilled in the art. Preferred catalysts are complexes with ruthenium. Typical details can be found in Examples 2a, 3a, 4a and 27a.

Compounds of the general formula III are converted to compounds of the general formula V by oxidative cleavage of the double bond by the methods known to those skilled in the art. Typical details can be found in Examples 21b and 28b.

Compounds of the general formula V are converted to compounds of the general formula IV in a Horner-Wittig or Wittig reaction by the methods known to those skilled in the art. Typical details can be found in Examples 6a-10a, 12a, 14a-16a, 18a, 21a-26a, 28a, 29, 32a and 33a.

Compounds of the general formula V are converted to compounds of the general formula VI by reaction with oximes or oxime ethers by the methods known to those skilled in the art. Typical details can be found in Examples 34a-38a.

Functional groups present in $R^1$, $R^2$ or $R^3$ in compounds of the general formulae III, IV, V, VI and I' can be converted further by the methods known to those skilled in the art. Examples include ester hydrolysis as described in Examples 5, 13, 17, 50, 52 and 56, esterification of carboxylic acids as described by way of example in Examples 30 and 31, conversion of a hydroxyl group to an azide group and reduction of the latter to an amino group as described by way of example in Examples 39b and 39a, and further functional transformation of the latter, for example to give ureas, as described by way of example in Examples 39, 40-48, 49a, 51a, 53, 54, 55a, 57 and 58.

If not already accomplished by the reactions described, any ketals present in the compounds of the general formulae I', IV, VI are cleaved to give X' and/or, if $R^8$ is defined as hydrogen and $R^9$ is defined as hydroxyl, water is eliminated. Typical details can be found in Examples 1-4, 6-12, 14-16, 18-28, 32-38, 49, 51 and 55.

To the extent that the preparation of the starting compounds is not described here, they are known to the person skilled in the art or are preparable analogously to known compounds or processes described here.

The salts are prepared in a customary manner, by admixing a solution of the compounds of the general chemical formula I with the equivalent amount or an excess of a base or acid which may be in solution, optionally removing the precipitate or working up the solution in a customary manner.

The examples which follow serve to illustrate the invention without restricting it in any way.

EXAMPLE 1

(8S,11R,13S,14S,17S)-17-hydroxy-13-methyl-17-pentafluoroethyl-11-(4-vinylphenyl)-1,2,6,7,8,11,12,13,14,15,16,17-dodecahydrocyclopenta[a]phenanthren-3-one

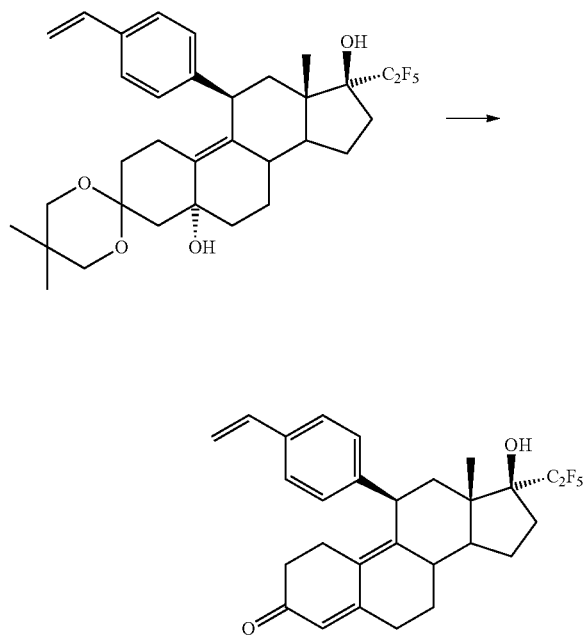

The solution of 5.0 g (8.38 mmol) of the compound prepared according to Example 1a in 250 ml of acetone was admixed with 12 ml of 4N hydrochloric acid and the mixture was stirred at 23° C. for 30 minutes. The mixture was poured into a saturated sodium hydrogencarbonate solution and extracted repeatedly with dichloromethane, the combined organic extracts were dried over sodium sulphate and the residue obtained after filtration and removal of solvent was purified by crystallization from diisopropyl ether. 3.92 g (95%) of the title compound were isolated as a crystalline solid.

$^1$H NMR (CDCl$_3$): =0.66 (3H), 1.45-1.60 (2H), 1.76-2.68 (14H), 2.77 (1H), 4.48 (1H), 5.27 (1H), 5.77 (1H), 5.83 (1H), 6.73 (1H), 7.18 (2H), 7.38 (2H) ppm.

EXAMPLE 1a (5R,8S,11R,13S,14S,17S)-11-(4-ethenylphenyl)-5',5',13-trimethyl-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

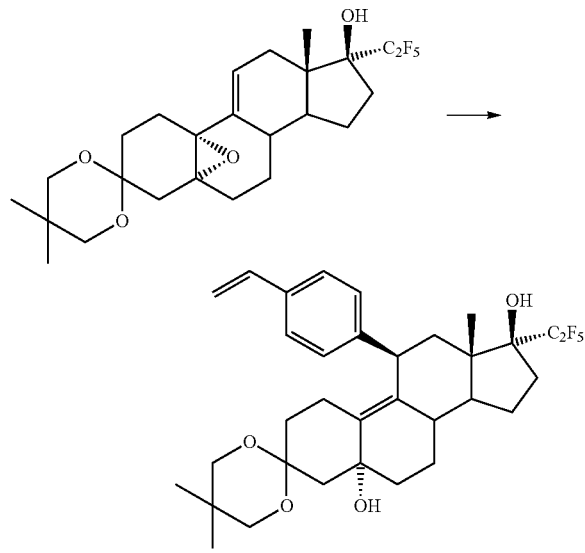

2.22 g of magnesium turnings and a solution of 11.95 ml of 4-bromostyrene in 75 ml of tetrahydrofuran were used to prepare the Grignard reagent, with gentle heating to 30-50° C. and optionally with addition of an iodine crystal. The mixture was cooled to 5° C., 117 mg of copper(I) chloride were added, and the solution of 15 g (30.5 mmol) of (5R,8S,10R,13S,14S,17S)-17-pentafluoroethyl-5,10-epoxy-5',5',13-trimethyl-1,2,3,4,6,7,8,12,13,14,15,16,17-tridecahydrospiro[cyclopenta[a]phenanthrene-3,2'-[1,3]dioxane]-17-ol in 150 ml of tetrahydrofuran was added dropwise. The mixture was stirred at 23° C. for another 1 hour, diluted with ethyl acetate and poured into a saturated ammonium chloride solution. The aqueous phase was extracted repeatedly with ethyl acetate, and the combined organic extracts were washed with saturated sodium chloride solution and dried over sodium sulphate. The solid obtained after filtration and removal of solvent was recrystallized from hexane, and 16.6 g (91%) of the title compound were isolated as a colourless solid.

EXAMPLE 2

(8S,11R,13S,14S,17S)-17-hydroxy-11-[4-((E)-3-hydroxypropenyl)phenyl]-13-methyl-17-pentafluoroethyl-1,2,6,7,8,11,12,13,14,15,16,17-dodecahydrocyclopenta[a]phenanthren-3-one

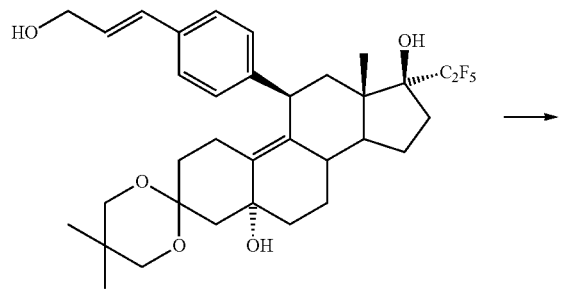

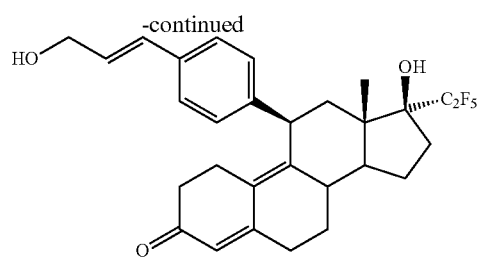

In analogy to Example 1, 7.9 mg (13 µmol) of the compound prepared according to Example 2a were converted and, after workup and purification, 4.5 mg (68%) of the title compound were isolated as a colourless foam.

$^1$H NMR (CDCl$_3$): =0.65 (3H), 1.42-1.64 (3H), 1.78-1.91 (3H), 2.04-2.69 (11H), 2.78 (1H), 4.37 (2H), 4.49 (1H), 5.83 (1H), 6.38 (1H), 6.63 (1H), 7.17 (2H), 7.36 (2H) ppm.

EXAMPLE 2a (5R,8S,11R,13S,14S,17S)-11-{4-[(1E)-3-hydroxyprop-1-en-1-yl]phenyl}-5',5',13-trimethyl-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

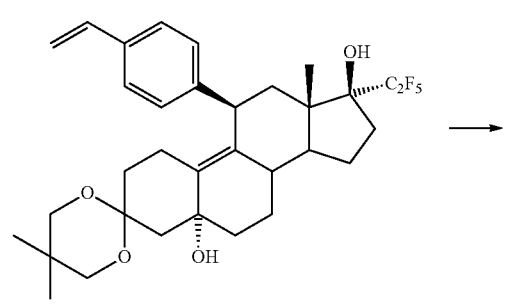

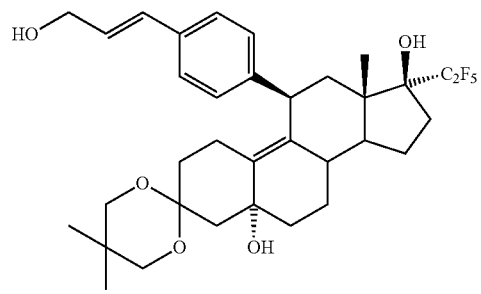

The solution of 1.0 g (1.68 mmol) of the compound prepared according to Example 1a in 16.5 ml of dichloromethane was admixed with 0.57 ml of allyl alcohol, 145 mg of [[1,3-bis(2,4,6-trimethylphenyl)-2-imidazolidinyl]methyl]dichloro(phenylmethylene)(tricyclohexylphosphoranyl)ruthenium, and heated under reflux for 4.5 hours. The mixture was purified by chromatography, and 163 mg (16%) of the title compound were isolated as a colourless foam.

EXAMPLE 3

(8S,11R,13S,14S,17S)-17-hydroxy-11-{4-[(E)-3-(4-methoxyphenyl)-propenyl]phenyl}-13-methyl-17-pentafluoroethyl-1,2,6,7,8,11,12,13,14,15,16,17-dodecahydrocyclopenta[a]phenanthren-3-one

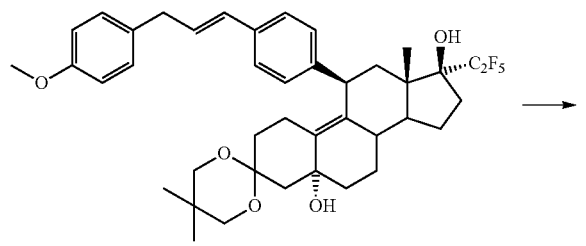

→

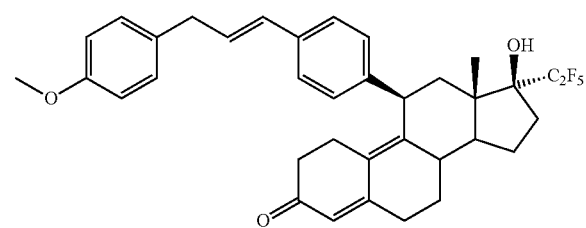

In analogy to Example 1, 15 mg (21 µmol) of the compound prepared according to Example 3a were converted and, after workup and purification, 7.3 mg (57%) of the title compound were isolated as a colourless foam.

¹H NMR (CDCl₃): =0.65 (3H), 1.44-1.60 (2H), 1.76-1.90 (3H), 2.07 (1H), 2.10 (1H), 2.26-2.68 (9H), 2.77 (1H), 3.52 (2H), 3.84 (3H), 4.46 (1H), 5.82 (1H), 6.30-6.47 (2H), 6.89 (2H), 7.13 (2H), 7.20 (2H), 7.31 (2H) ppm.

EXAMPLE 3a (5R,8S,11R,13S,14S,17S)-11-{4-[(1E)-3-(4-methoxyphenyl)prop-1-en-1-yl]phenyl}-5',5',13-trimethyl-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

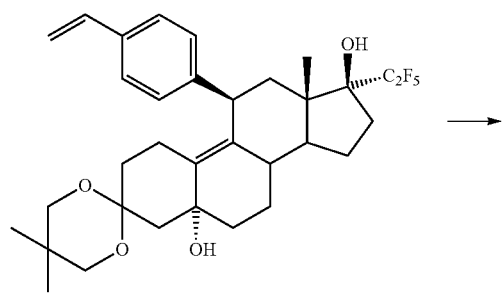

→

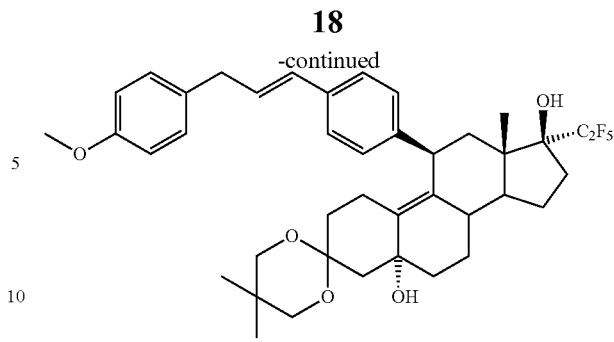

In analogy to Example 2a, 50 mg (84 µmol) of the compound prepared according to Example 1a were converted and, after workup and purification, 15 mg (25%) of the title compound were isolated as a colourless foam.

EXAMPLE 4

2-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}malonic acid dimethyl ester

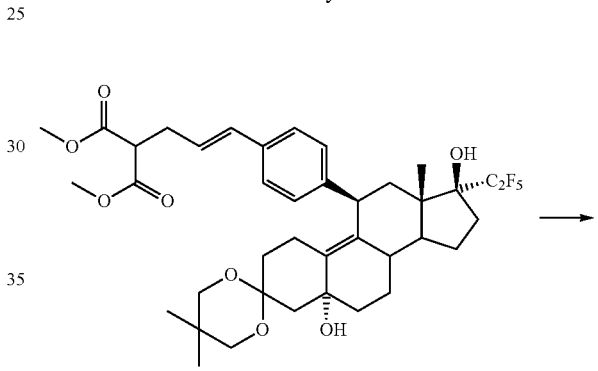

→

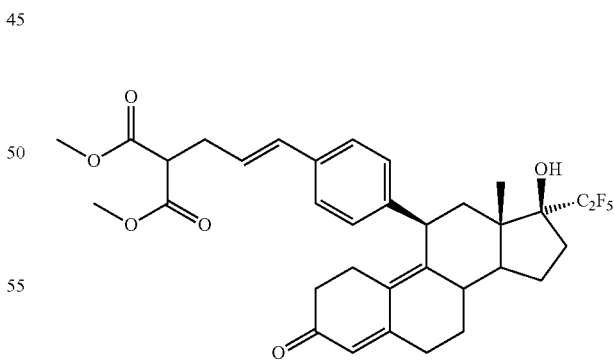

In analogy to Example 1, 51 mg (69 µmol) of the compound prepared according to Example 4a were converted and, after workup and purification, 15.2 mg (35%) of the title compound were isolated as a colourless foam.

¹H NMR (CDCl₃): =0.60 (3H), 1.40-1.54 (2H), 1.73-1.87 (3H), 2.05 (1H), 2.20 (1H), 2.24-2.63 (9H), 2.72 (1H), 2.79 (2H), 3.51 (1H), 3.74 (6H), 4.41 (1H), 5.78 (1H), 6.10 (1H), 6.43 (1H), 7.09 (2H), 7.24 (2H) ppm.

EXAMPLE 4a dimethyl[(2E)-3-{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-1-yl]phenyl}prop-2-en-1-yl]propanedioate

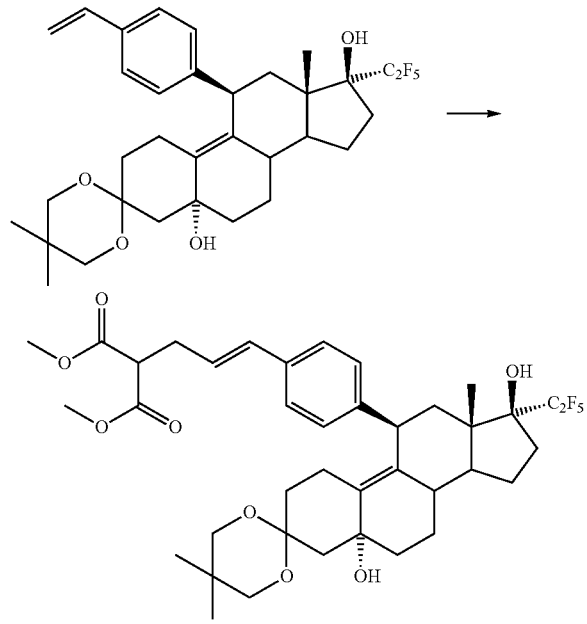

In analogy to Example 2a, 200 mg (340 μmol) of the compound prepared according to Example 1a were converted and, after workup and purification, 42 mg (20%) of the title compound were isolated as a colourless foam.

EXAMPLE 5

2-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}malonic acid

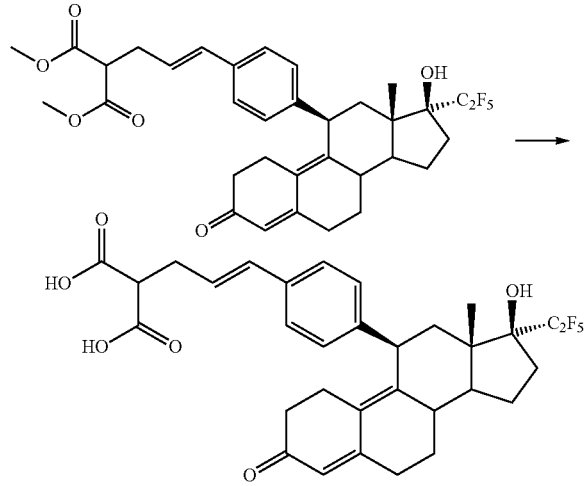

The solution of 323 mg (0.51 mmol) of the compound prepared according to Example 4 in 5.4 ml of tetrahydrofuran was admixed with 2.3 ml of a 5% aqueous lithium hydroxide solution and stirred at 23° C. for 3 hours. The mixture was acidified by adding 1 molar hydrochloric acid, saturated with sodium chloride and extracted repeatedly with ethyl acetate, and the combined organic extracts were dried over sodium sulphate. The residue obtained after filtration and solvent removal was purified by chromatography. 146 mg (47%) of the title compound were isolated.

$^1$H NMR (CD$_3$OD): =0.59 (3H), 1.33-1.55 (2H), 1.68-1.83 (3H), 2.08 (1H), 2.16-2.47 (5H), 2.54-2.84 (7H), 3.39 (1H), 4.48 (1H), 5.73 (1H), 6.17 (1H), 6.44 (1H), 7.15 (2H), 7.26 (2H) ppm.

EXAMPLE 6

(8S,11R,13S,14S,17S)-17-hydroxy-13-methyl-17-pentafluoroethyl-11-[4-((E)-2-pyridin-2-ylvinyl)phenyl]-1,2,6,7,8,11,12,13,14,15,16,17-dodecahydrocyclopenta[a]phenanthren-3-one

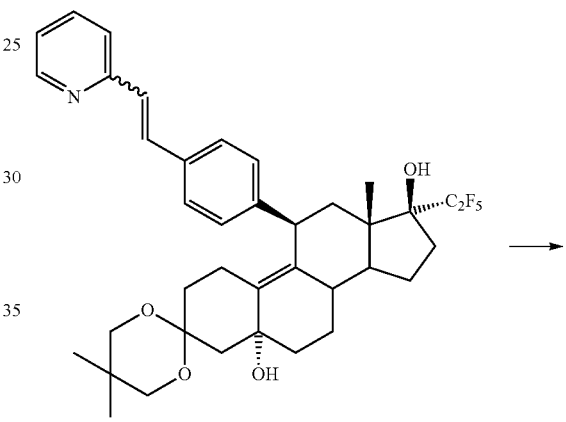

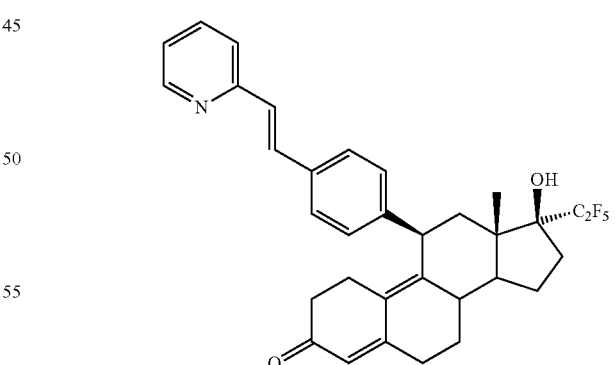

In analogy to Example 1, 67 mg (99 μmol) of a mixture of the compounds A and B prepared according to Example 6a were converted and, after workup and purification, 42 mg (74%) of the title compound were isolated as a colourless foam.

$^1$H NMR (CDCl$_3$): =0.67 (3H), 1.44-1.62 (2H), 1.79-1.92 (3H), 2.12 (1H), 2.24 (1H), 2.30-2.71 (9H), 2.79 (1H), 4.51

(1H), 5.84 (1H), 7.13-7.26 (4H), 7.43 (1H), 7.54 (2H), 7.62 (1H), 7.71 (1H), 8.64 (1H) ppm.

EXAMPLE 6a (5R,8S,11R,13S,14S,17S)-5',5',13-trimethyl-17-(pentafluoroethyl)-11-{4-[(E)-2-(pyridin-2-yl)ethenyl]phenyl}-1,2,3,4,6,7,8,11,12,13,14,15,16,17-tetradecahydrospiro[cyclopenta[a]phenanthrene-3,2'-[1,3]dioxane]-5,17-diol

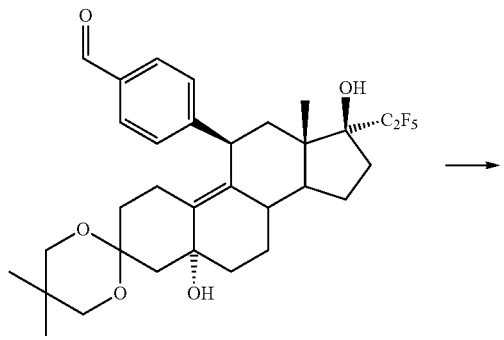

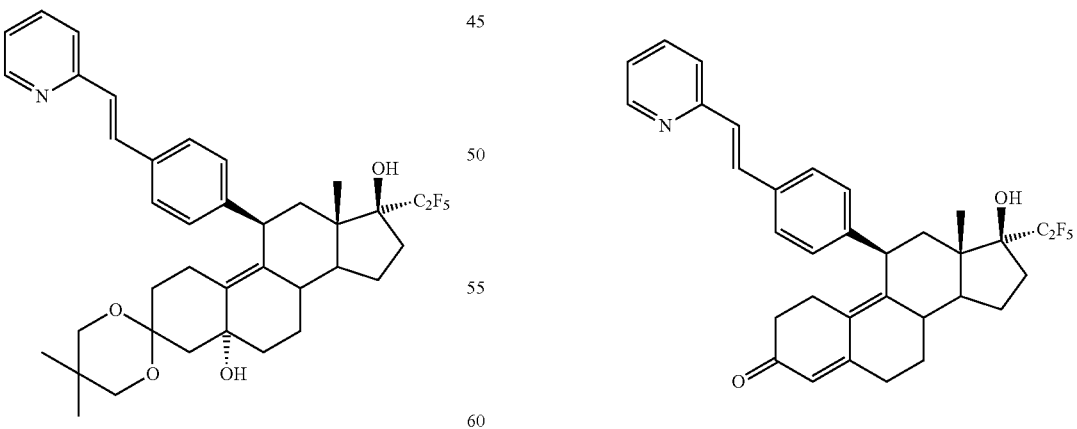

The solution of 345 mg of diethyl pyridin-2-ylmethylphosphonate in 10 ml of tetrahydrofuran was admixed at −10° C. with 0.6 ml of a 1.6 molar solution of n-butyllithium in hexane, and the mixture was stirred at 23° C. for 1.5 hours. Subsequently, the mixture was cooled to −70° C., the solution of 300 mg (0.5 mmol) of the compound prepared according to Example 28b in 5 ml of tetrahydrofuran was added dropwise, the cooling bath was removed and the mixture was left to react for 1.5 hours. The mixture was poured into a saturated ammonium chloride solution and extracted repeatedly with ethyl acetate, and the combined organic extracts were dried over sodium sulphate. The residue obtained after filtration and solvent removal was purified by chromatography. 302 mg (89%) of the title compound were isolated as a colourless foam.

EXAMPLE 7

(8S,11R,13S,14S,17S)-17-hydroxy-13-methyl-17-pentafluoroethyl-11-[4-((E)-2-pyridin-3-ylvinyl)phenyl]-1,2,6,7,8,11,12,13,14,15,16,17-dodecahydrocyclopenta[a]phenanthren-3-one

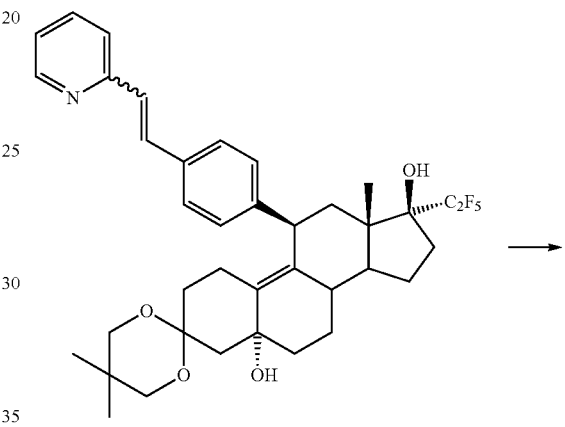

In analogy to Example 1, 100 mg (0.15 mmol) of a mixture of the compounds A and B prepared according to Example 7a were converted and, after workup and purification, 61.4 mg (73%) of the title compound were isolated as a colourless foam.

$^1$H NMR (CDCl$_3$): =0.66 (3H), 1.41-1.48 (2H), 1.75-1.91 (3H), 2.08 (1H), 2.22-2.65 (9H), 2.74 (1H), 3.97 (1H), 4.43

(1H), 5.80 (1H), 7.04 (1H), 7.09-7.18 (3H), 7.33 (1H), 7.43 (2H), 7.86 (1H), 8.46 (1H), 8.63 (1H) ppm.

EXAMPLE 7a (5R,8S,11R,13S,14S,17S)-5',5',13-trimethyl-17-(pentafluoroethyl)-11-{4-[(E/Z)-2-(pyridin-3-yl)ethenyl]phenyl}-1,2,3,4,6,7,8,11,12,13,14,15,16,17-tetradecahydrospiro[cyclopenta[a]phenanthrene-3,2'-[1,3]dioxane]-5,17-diol

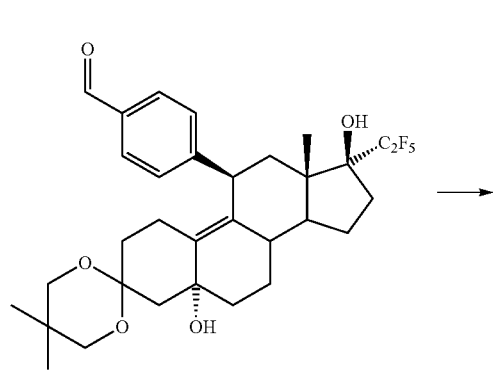

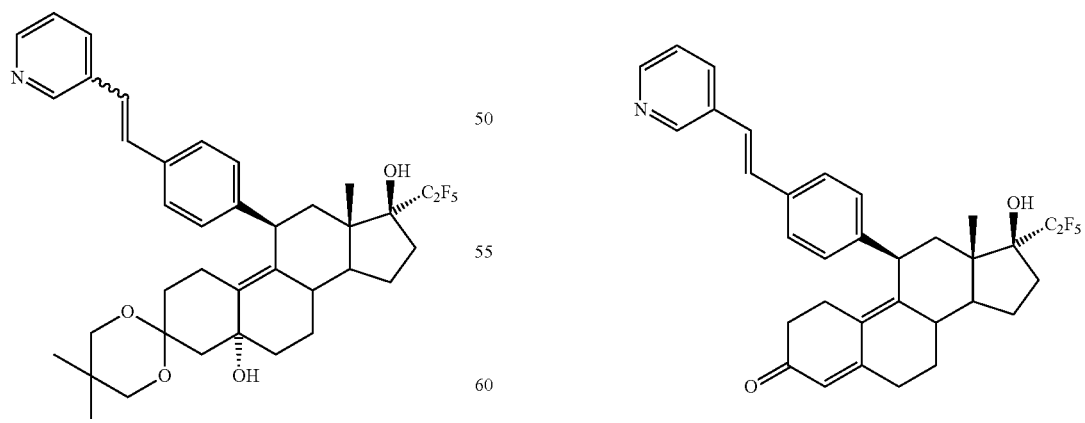

In analogy to Example 6a, 250 mg (0.42 mmol) of the compound prepared according to Example 28b were converted using diethyl pyridin-3-ylmethylphosphonate and, after workup and purification, 170 mg (60%) of a mixture of the two title compounds were isolated as a colourless foam.

EXAMPLE 8

(8S,11R,13S,14S,17S)-17-hydroxy-13-methyl-17-pentafluoroethyl-11-[4-((E)-2-pyridin-4-ylvinyl)phenyl]-1,2,6,7,8,11,12,13,14,15,16,17-dodecahydrocyclopenta[a]phenanthren-3-one

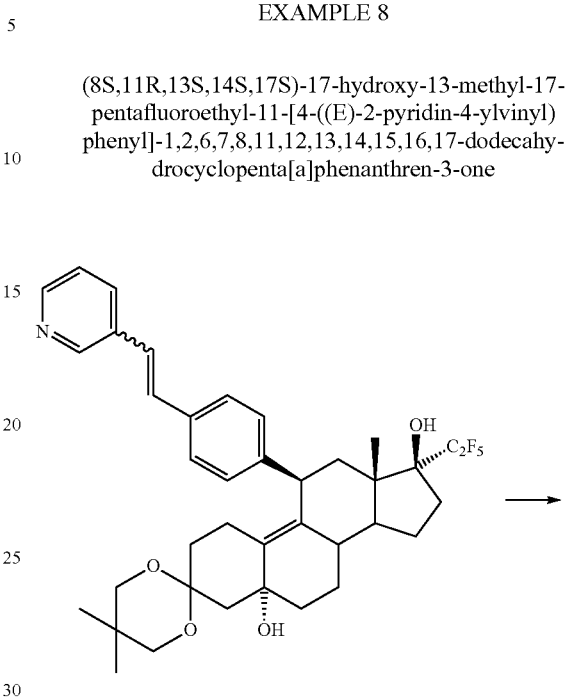

In analogy to Example 1, 100 mg (0.15 mmol) of a mixture of the compounds A and B prepared according to Example 8a were converted and, after workup and purification, 57.2 mg (68%) of the title compound were isolated as a colourless foam.

¹H NMR (CDCl₃): =0.63 (3H), 1.41-1.58 (2H), 1.74-1.89 (3H), 2.08 (1H), 2.22-2.68 (10H), 2.74 (1H), 4.46 (1H), 5.79 (1H), 6.98 (1H), 7.19 (2H), 7.27 (1H), 7.35 (2H), 7.45 (2H), 8.55 (2H) ppm.

EXAMPLE 8a (5R,8S,11R,13S,14S,17S)-5',5',13-trimethyl-17-(pentafluoroethyl)-11-{4-[(E/Z)-2-(pyridin-4-yl)ethenyl]phenyl}-1,2,3,4,6,7,8,11,12,13,14,15,16,17-tetradecahydrospiro[cyclopenta[a]phenanthrene-3,2'-[1,3]dioxane]-5,17-diol

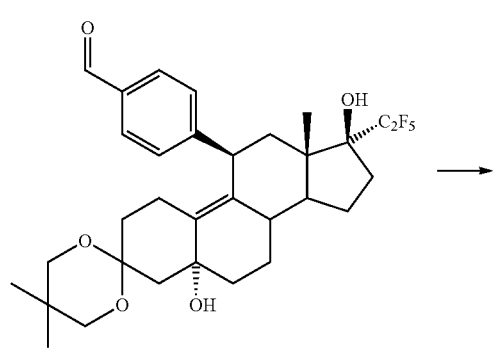

In analogy to Example 6a, 200 mg (0.33 mmol) of the compound prepared according to Example 28b were converted using diethyl pyridin-4-ylmethylphosphonate and,  after workup and purification, 182 mg (81%) of a mixture of the two title compounds were isolated as a colourless foam.

EXAMPLE 9

(8S,11R,13S,14S,17S)-17-hydroxy-13-methyl-11-{4-[(E)-2-(2-methylthiazol-4-yl)vinyl]phenyl}-17-pentafluoroethyl-1,2,6,7,8,11,12,13,14,15,16,17-dodecahydrocyclopenta[a]phenanthren-3-one

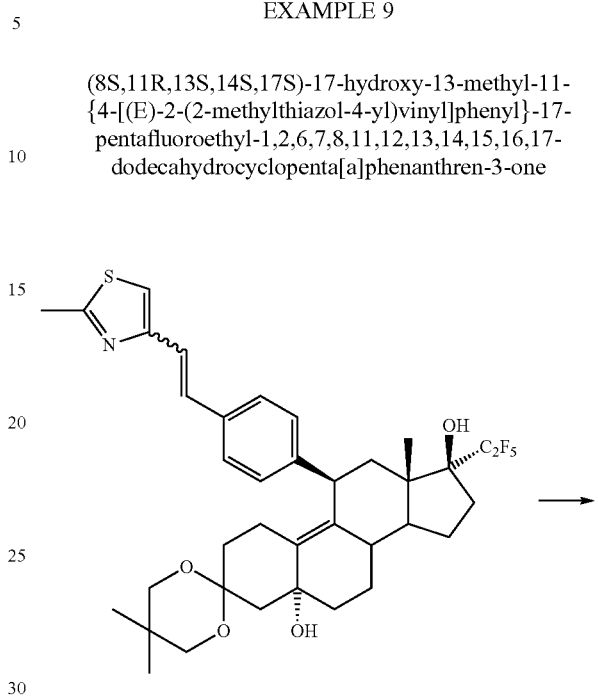

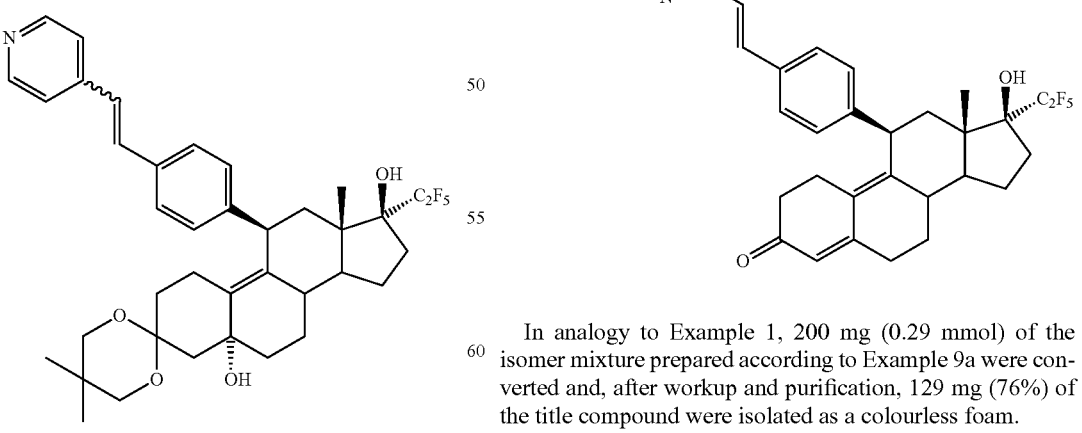

In analogy to Example 1, 200 mg (0.29 mmol) of the isomer mixture prepared according to Example 9a were converted and, after workup and purification, 129 mg (76%) of the title compound were isolated as a colourless foam.

¹H NMR (CDCl₃): =0.63 (3H), 1.41-1.55 (2H), 1.75-1.85 (3H), 2.06 (1H), 2.08 (1H), 2.27-2.65 (9H), 2.74 (1H), 2.75 (3H), 4.45 (1H), 5.79 (1H), 6.99 (1H), 7.01 (1H), 7.15 (2H), 7.38 (1H), 7.42 (2H) ppm.

EXAMPLE 9a (5R,8S,11R,13S,14S,17S)-5′,5′,13-trimethyl-1-{4-[(E/Z)-2-(2-methyl-1,3-thiazol-4-yl)ethenyl]phenyl}-17-(pentafluoroethyl)-1,2,3,4,6,7,8,11,12,13,14,15,16,17-tetradecahydrospiro[cyclopenta[a]phenanthrene-3,2′-[1,3]dioxane]-5,17-diol

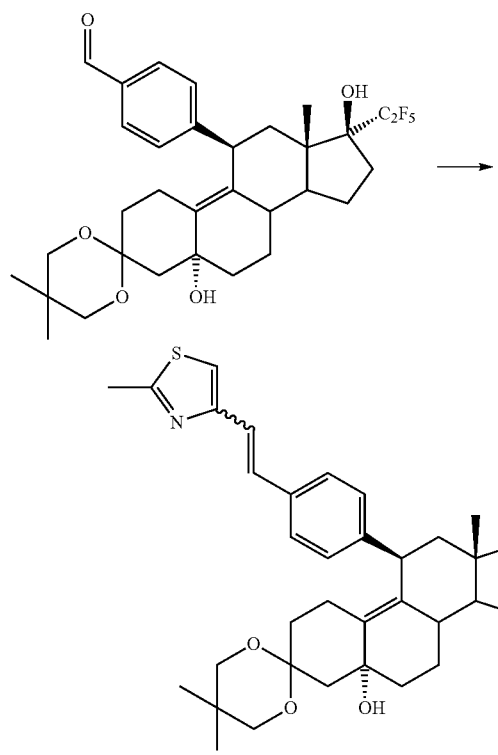

In analogy to Example 6a, 500 mg (0.84 mmol) of the compound prepared according to Example 28b were converted using diethyl (2-methylthiazol-4-ylmethyl)phosphonate and, after workup and purification, 479 mg (83%) of a mixture of the two title compounds were isolated as a colourless foam.

EXAMPLE 10

(8S,11R,13S,14S,17S)-17-hydroxy-13-methyl-11-{4-[(E)-2-(2-methylbenzothiazol-5-yl)vinyl]phenyl}-17-pentafluoroethyl-1,2,6,7,8,11,12,13,14,15,16,17-dodecahydrocyclopenta[a]phenanthren-3-one

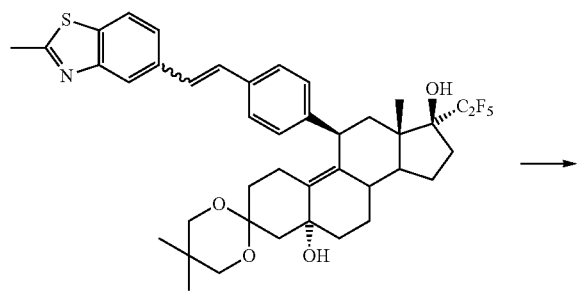

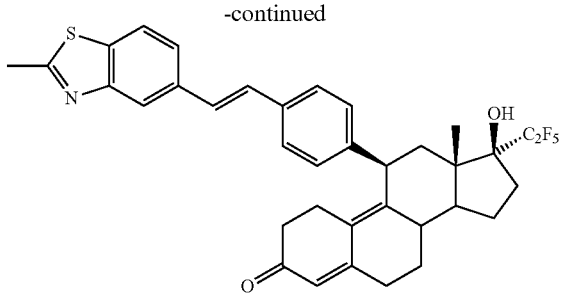

In analogy to Example 1, 84 mg (0.11 mmol) of the compound prepared according to Example 10a were converted and, after workup and purification, 44 mg (61%) of the title compound were isolated as a colourless foam.
$^1$H NMR (CDCl$_3$): =0.64 (3H), 1.41-1.57 (2H), 1.75-1.88 (3H), 2.07 (1H), 2.17 (1H), 2.24-2.67 (9H), 2.75 (1H), 2.84 (3H), 4.46 (1H), 5.79 (1H), 7.09-7.22 (4H), 7.45 (2H), 7.53 (1H), 7.78 (1H), 8.02 (1H) ppm.

EXAMPLE 10a (5R,8S,11R,13S,14S,17S)-5′,5′,13-trimethyl-11-{4-[(E)-2-(2-methyl-1,3-benzothiazol-5-yl)ethenyl]phenyl}-17-(pentafluoroethyl)-1,2,3,4,6,7,8,11,12,13,14,15,16,17-tetradecahydrospiro[cyclopenta[a]phenanthrene-3,2′-[1,3]dioxane]-5,17-diol

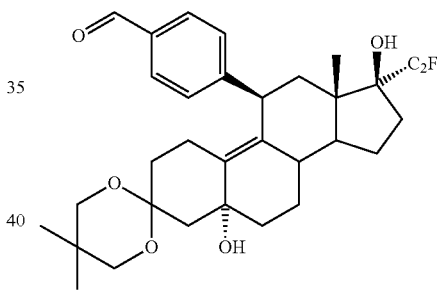

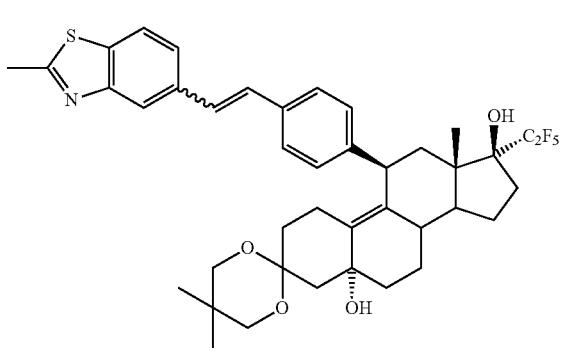

In analogy to Example 6a, 196 mg (0.33 mmol) of the compound prepared according to Example 28b were converted using diethyl (2-methylbenzothiazol-5-ylmethyl)

phosphonate and, after workup and purification, 98 mg (40%) of the title compounds were isolated as a colourless foam.

EXAMPLE 11

(8S,11R,13S,14S,17S)-17-hydroxy-11-(4-isopropenylphenyl)-13-methyl-17-pentafluoroethyl-1,2,6,7,8,11,12,13,14,15,16,17-dodecahydrocyclopenta[a]phenanthren-3-one

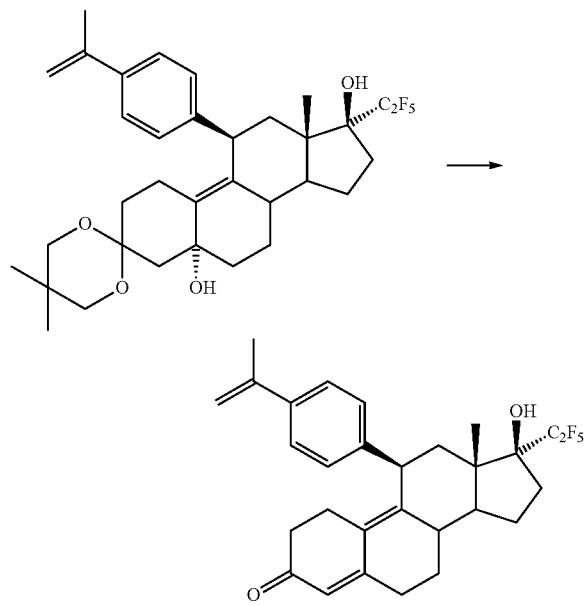

In analogy to Example 1, 21.4 mg (35 μmol) of the compound prepared according to Example 11a were converted and, after workup and purification, 11.1 mg (63%) of the title compound were isolated as a colourless foam.

$^1$H NMR (CDCl$_3$): =0.62 (3H), 1.37-1.57 (2H), 1.73-1.88 (3H), 2.01-2.65 (11H), 2.13 (3H), 2.74 (1H), 4.44 (1H), 5.06 (1H), 5.37 (1H), 5.78 (1H), 7.13 (2H), 7.40 (2H) ppm.

EXAMPLE 11a (5R,8S,11R,13S,14S,17S)-5',5',13-trimethyl-17-(pentafluoroethyl)-11-[4-(prop-1-en-2-yl)phenyl]-1,2,3,4,6,7,8,11,12,13,14,15,16,17-tetradecahydrospiro[cyclopenta[a]phenanthrene-3,2'-[1,3]dioxane]-5,17-diol

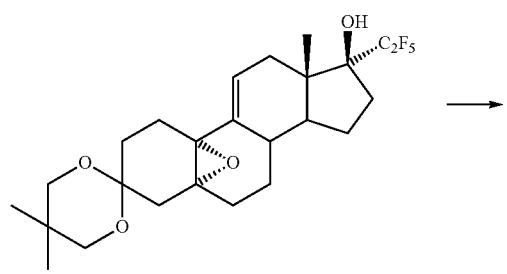

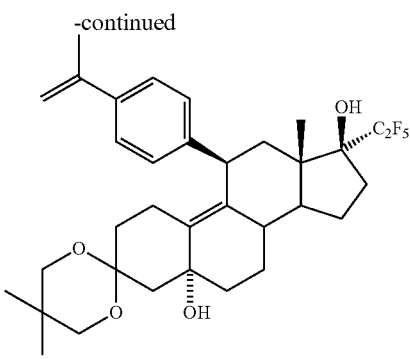

In analogy to Example 1a, 5 g (10.2 mmol) of (5R,8S,10R,13S,14S,17S)-17-(pentafluoroethyl)-5,10-epoxy-5',5',13-trimethyl-1,2,3,4,6,7,8,12,13,14,15,16,17-tridecahydrospiro[cyclopenta[a]phenanthrene-3,2'-[1,3]dioxan]-17-ol were reacted with the Grignard reagent prepared from 10 g of 1-bromo-4-isopropenylbenzene and, after workup and purification, 4.01 g (65%) of the title compound were isolated as a colourless foam.

EXAMPLE 12

(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]acrylic acid ethyl ester

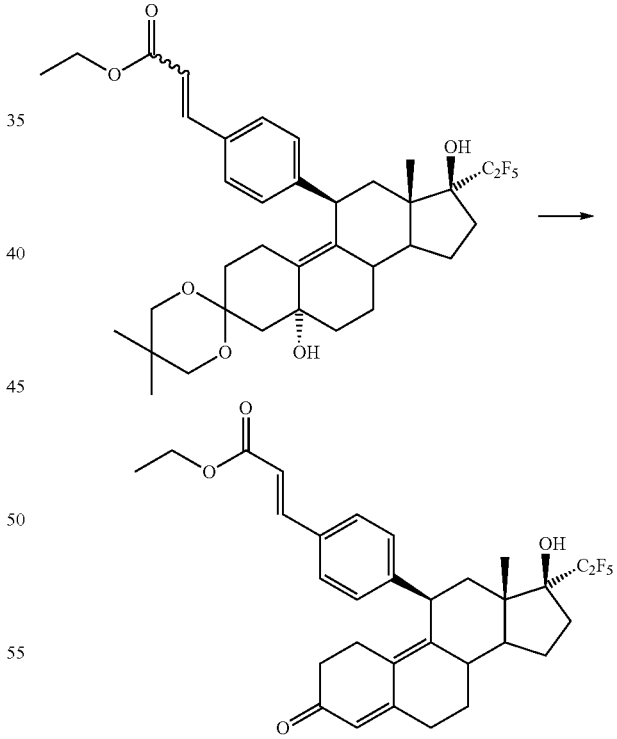

In analogy to Example 1, 50 mg (75 μmol) of the compound prepared according to Example 12a were converted and, after workup and purification, 25.2 mg (60%) of the title compound were isolated as a colourless foam.

$^1$H NMR (CDCl$_3$): =0.60 (3H), 1.33 (3H), 1.42-1.54 (2H), 1.76-1.86 (3H), 2.07 (1H), 2.13 (1H), 2.23-2.64 (9H), 2.73 (1H), 4.26 (2H), 4.46 (1H), 5.79 (1H), 6.40 (1H), 7.21 (2H), 7.45 (2H), 7.64 (1H) ppm.

EXAMPLE 12a ethyl(2E)-3-{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl]phenyl}prop-2-enoate

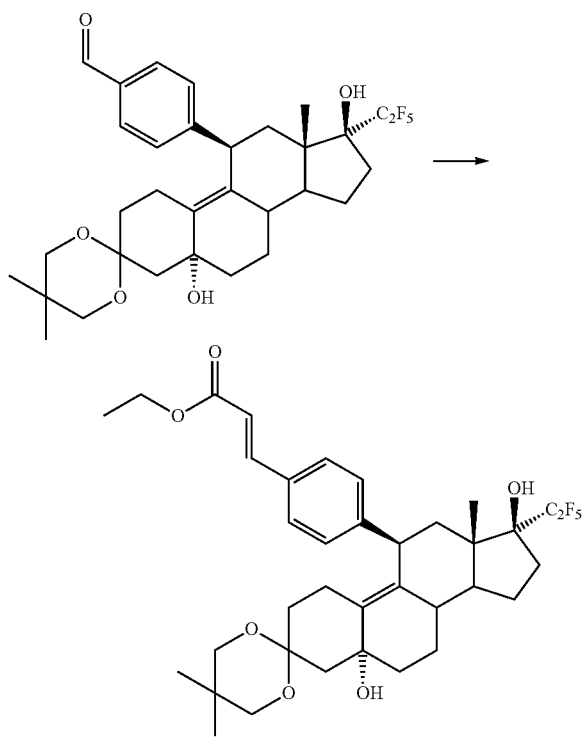

In analogy to Example 6a, 250 mg (0.42 mmol) of the compound prepared according to Example 28b were converted using ethyl(diethoxyphosphoryl)acetate and, after workup and purification, 230 mg (82%) of the title compound were isolated as a colourless foam.

EXAMPLE 13

(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]acrylic acid

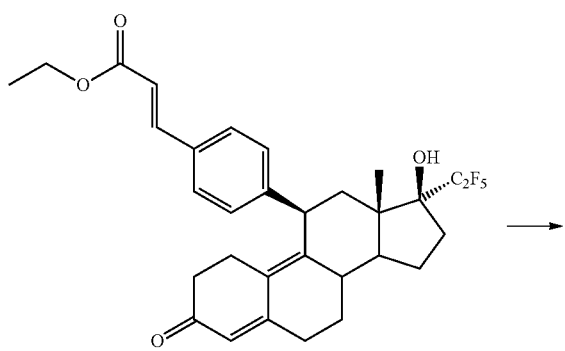

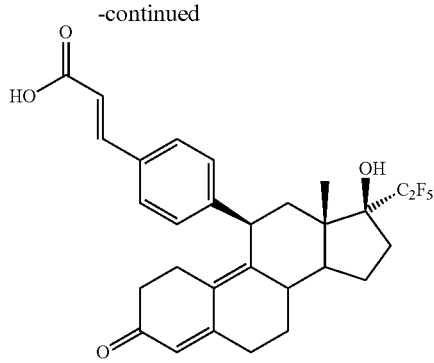

In analogy to Example 5, 20 mg (35 μmol) of the compound prepared according to Example 12 were converted and, after workup and purification, 5.2 mg (28%) of the title compound were isolated as a colourless foam.

$^1$H NMR (CD$_3$OD): =0.59 (3H), 1.37-1.55 (2H), 1.71-1.82 (3H), 2.10 (1H), 2.18-2.46 (5H), 2.56-2.73 (4H), 2.81 (1H), 4.54 (1H), 5.74 (1H), 6.44 (1H), 7.27 (2H), 7.46-7.52 (3H) ppm.

EXAMPLE 14

(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]acrylonitrile

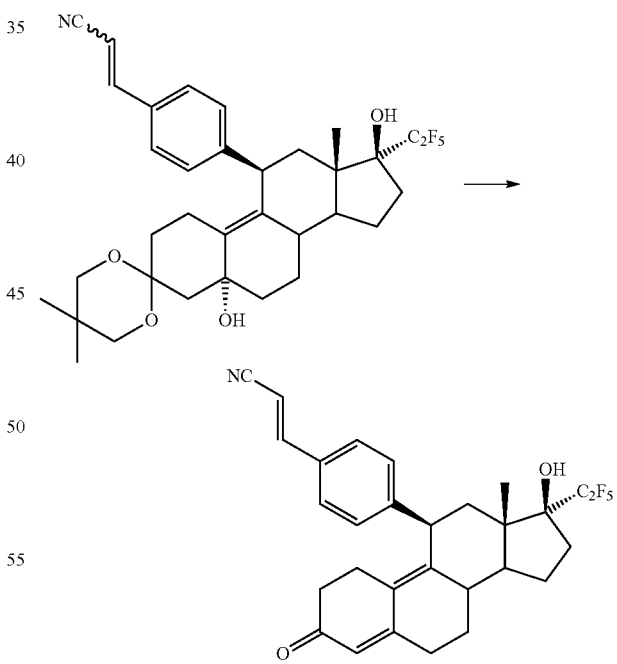

In analogy to Example 1, 50 mg (80 μmol) of the compound prepared according to Example 14a were converted and, after workup and purification, 21.2 mg (51%) of the title compound were isolated as a colourless foam.

$^1$H NMR (CDCl$_3$): =0.58 (3H), 1.40-1.56 (2H), 1.74-1.87 (3H), 2.03-2.13 (2H), 2.18-2.65 (9H), 2.72 (1H), 4.47 (1H), 5.80 (1H), 5.84 (1H), 7.24 (2H), 7.36 (1H), 7.38 (2H) ppm.

EXAMPLE 14a (2E/Z)-3-{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl]phenyl}prop-2-enonitrile

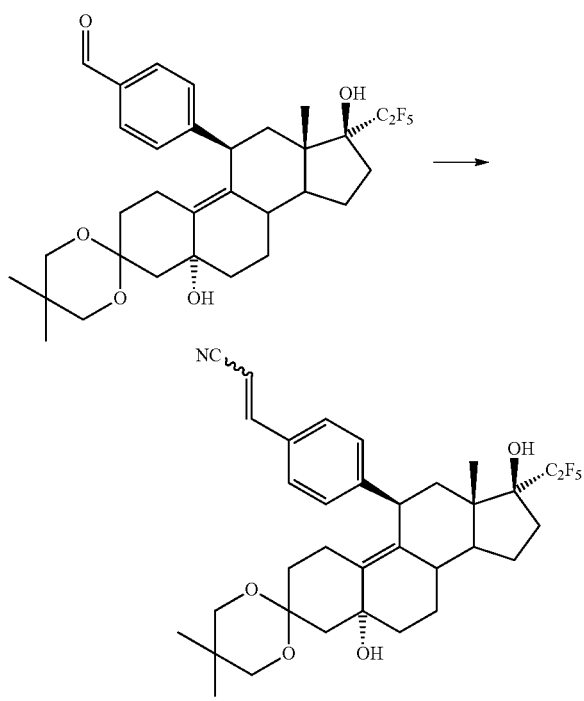

In analogy to Example 6a, 1.0 g (1.67 mmol) of the compound prepared according to Example 28b were converted using diethyl cyanomethylphosphonate and, after workup and purification, 961 mg (93%) of the title compound were isolated as a colourless foam.

EXAMPLE 15

(2E,4E)-5-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]penta-2,4-dienoic acid ethyl ester

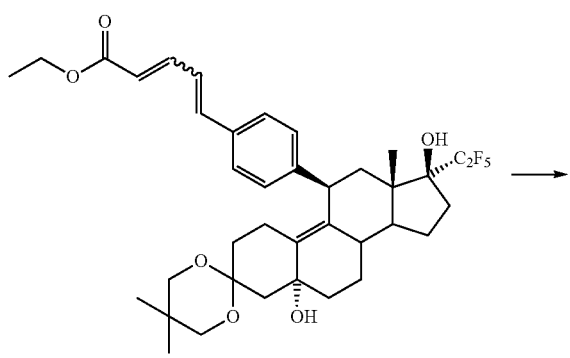

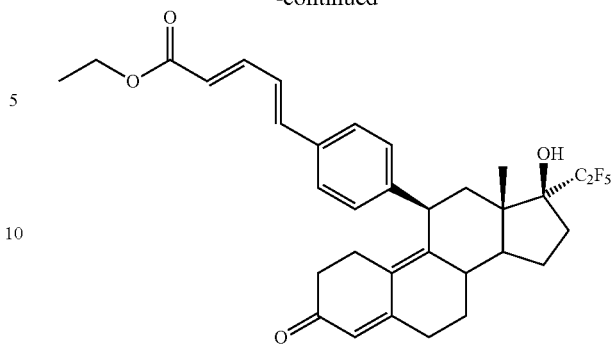

In analogy to Example 1, 50 mg (72 µmol) of a mixture of the compounds prepared according to Example 15a were converted and, after workup and purification, 27.7 mg (65%) of the title compound were isolated as a yellow foam.

$^1$H NMR (CDCl$_3$): =0.61 (3H), 1.31 (3H), 1.40-1.56 (2H), 1.73-1.87 (3H), 2.07 (1H), 2.11 (1H), 2.21-2.65 (9H), 2.73 (1H), 4.22 (2H), 4.45 (1H), 5.79 (1H), 5.98 (1H), 6.77-6.91 (2H), 7.17 (2H), 7.38 (2H), 7.44 (1H) ppm.

EXAMPLE 15a ethyl(2E/Z,4E/Z)-5-{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl]phenyl}penta-2,4-dienoate

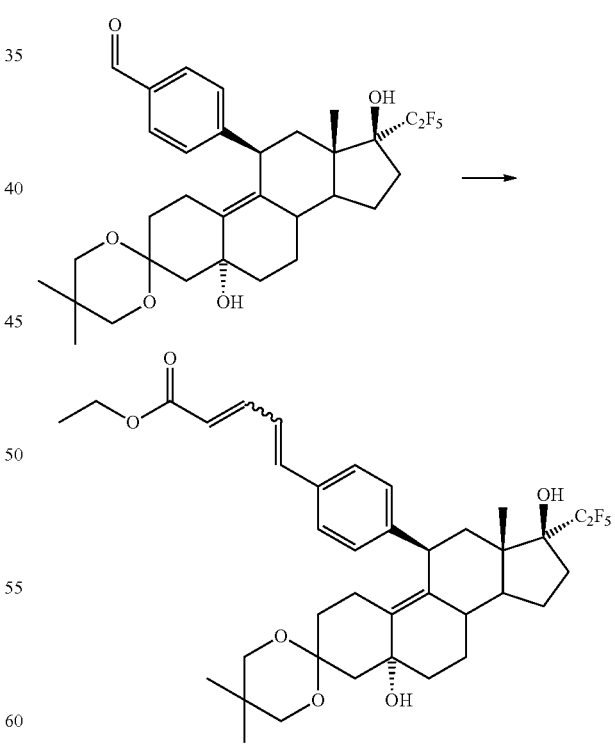

In analogy to Example 6a, 180 mg (0.3 mmol) of the compound prepared according to Example 28b were converted using ethyl (E)-4-(diethoxyphosphoryl)but-2-enoate and, after workup and purification, 170 mg (81%) of the title compound were isolated as a colourless foam.

EXAMPLE 16

(8S,11R,13S,14S,17S)-17-hydroxy-13-methyl-11-[4-((E)-3-oxobut-1-enyl)phenyl]-17-pentafluoroethyl-1,2,6,7,8,11,12,13,14,15,16,17-dodecahydrocyclopenta[a]phenanthren-3-one

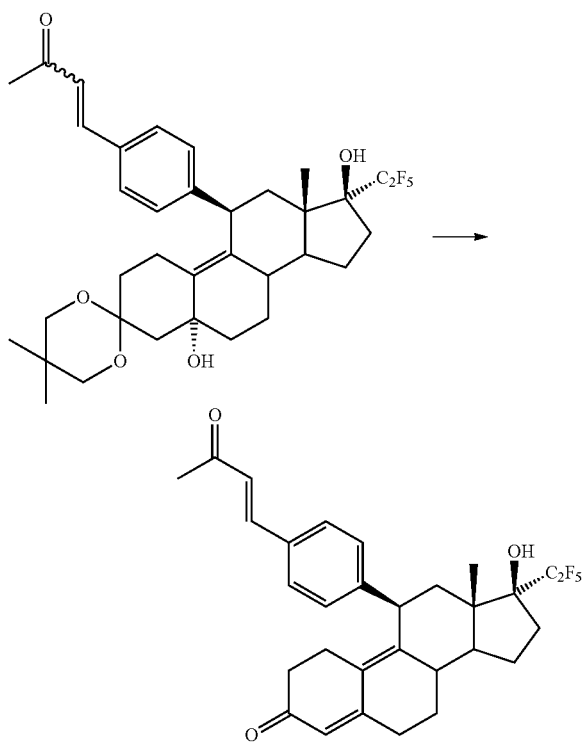

In analogy to Example 1, 33 mg (52 µmol) of a mixture of the compounds prepared according to Example 16a were converted and, after workup and purification, 6.7 mg (24%) of the title compound were isolated as a pale yellow foam.

$^1$H NMR (CDCl$_3$): =0.60 (3H), 1.41-1.56 (2H), 1.74-1.87 (3H), 2.03-2.15 (2H), 2.21-2.65 (9H), 2.38 (3H), 2.73 (1H), 4.46 (1H), 5.80 (1H), 6.68 (1H), 7.23 (2H), 7.43-7.51 (3H) ppm.

EXAMPLE 16a (3E/Z)-4-{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxan]-11-yl]phenyl}but-3-en-2-one

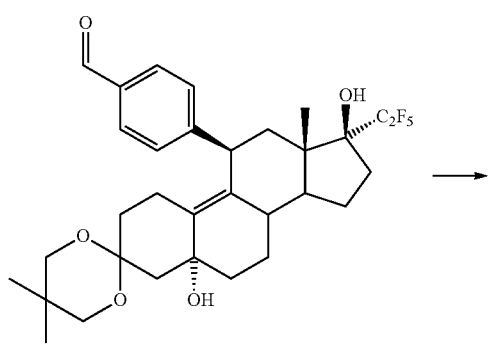

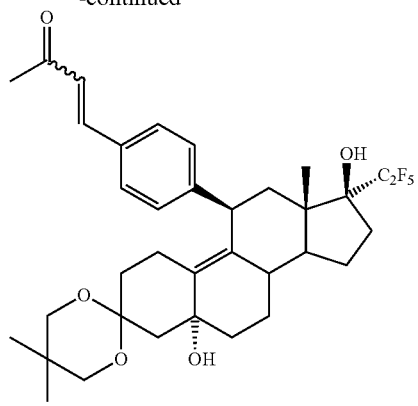

In analogy to Example 6a, 180 mg (0.3 mmol) of the compound prepared according to Example 28b were converted using dimethyl (2-oxopropyl)phosphonate and, after workup and purification, 33 mg (17%) of the title compounds were isolated as a colourless foam.

EXAMPLE 17

(2E,4E)-5-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]penta-2,4-dienoic acid

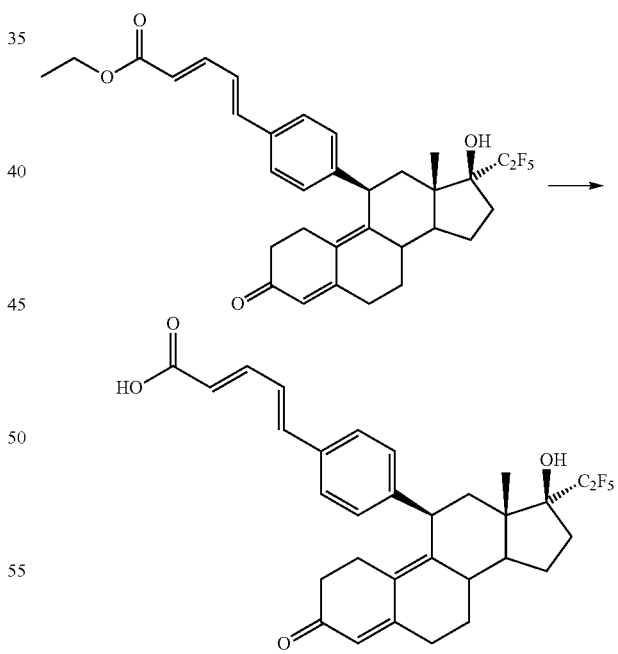

In analogy to Example 5, 20 mg (35 µmol) of the compound prepared according to Example 15 were converted and, after workup and purification, 3.1 mg (16%) of the title compound were isolated as a colourless foam.

$^1$H NMR (CD$_3$OD): =0.60 (3H), 1.35-1.59 (2H), 1.69-1.83 (3H), 2.09 (1H), 2.17-2.46 (5H), 2.54-2.74 (4H), 2.80 (1H), 4.51 (1H), 5.73 (1H), 5.99 (1H), 6.78-6.97 (2H), 7.19-7.32 (3H), 7.42 (2H) ppm.

EXAMPLE 18

(8S,11R,13S,14S,17S)-11-[((E/Z)-4-buta-1,3-dienyl)phenyl]-17-hydroxy-13-methyl-17-pentafluoroethyl-1,2,6,7,8,11,12,13,14,15,16,17-dodecahydrocyclopenta[a]phenanthren-3-one

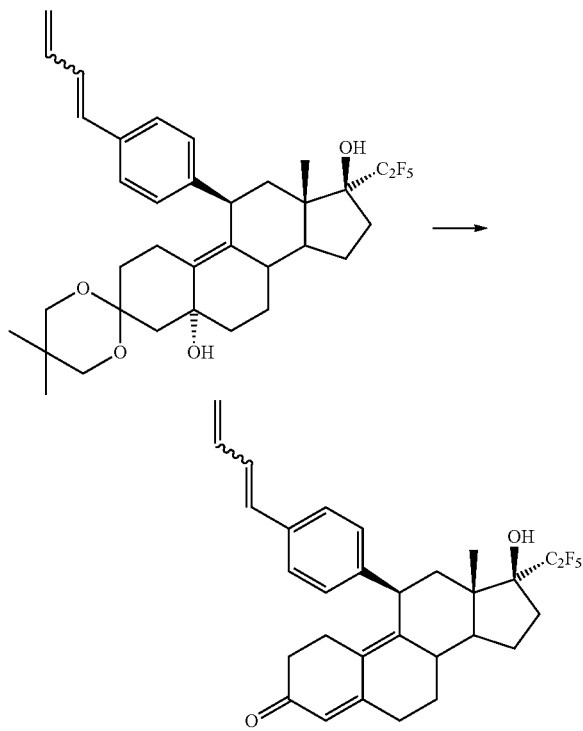

In analogy to Example 1, 39 mg (63 µmol) of a mixture of the compounds prepared according to Example 18a were converted and, after workup and purification, 12.9 mg (40%) of the title compounds were isolated as a pale yellow foam.

$^1$H NMR (CDCl$_3$): =0.62 (3H), 1.36-1.58 (2H), 1.73-1.88 (3H), 2.01-2.15 (2H), 2.22-2.65 (9H), 2.74 (1H), 4.44 (1H), 5.13-5.43 (2H), 5.79 (1H), 6.19-6.56 (2H), 6.69-6.95 (1H), 7.08-7.19 (2H), 7.21-7.36 (2H) ppm.

EXAMPLE 18a (5R,8S,11R,13S,14S,17S)-11-[((E/Z)-4-buta-1,3-dienyl)phenyl]-5',5',13-trimethyl-17-pentafluoroethyl-1,2,3,4,6,7,8,11,12,13,14,15,16,17-tetradecahydrospiro[cyclopenta[a]phenanthrene-3,2'-[1,3]dioxane]-5,17-diol

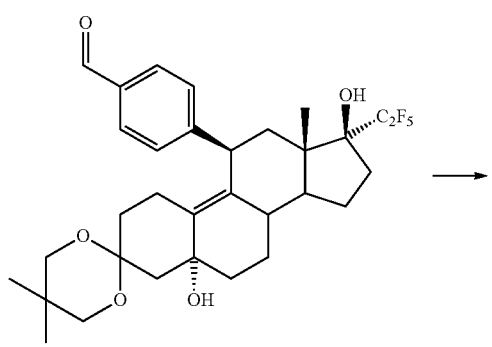

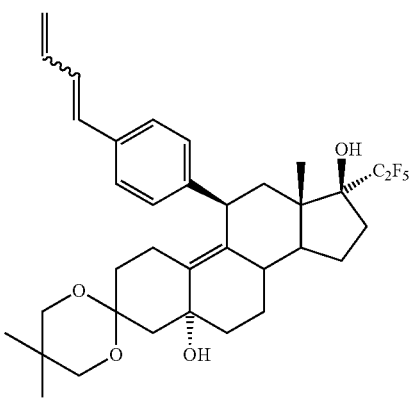

In analogy to Example 6a, 180 mg (0.3 mmol) of the compound prepared according to Example 28b were converted using cyclopropyl(triphenylphosphonium)bromide and, after workup and purification, 89 mg (48%) of the title compounds were isolated as a colourless foam.

EXAMPLE 19

(8S,11R,13S,14S,17S)-17-hydroxy-13-methyl-17-pentafluoroethyl-11-(3-vinylphenyl)-1,2,6,7,8,11,12,13,14,15,16,17-dodecahydrocyclopenta[a]phenanthren-3-one

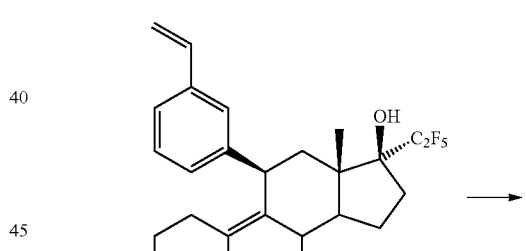

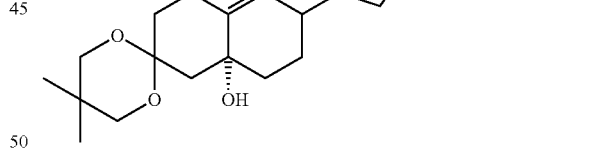

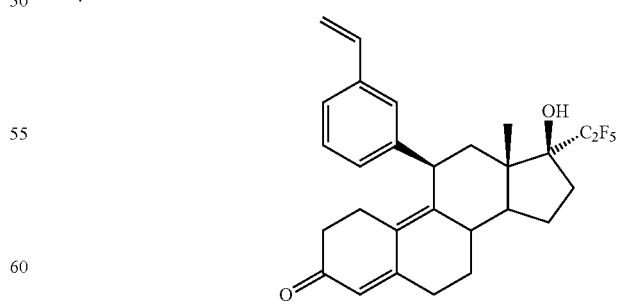

In analogy to Example 1, 300 mg (0.5 mmol) of the compound prepared according to Example 19a were converted and, after workup and purification, 165 mg (67%) of the title compound were isolated as a colourless foam.

¹H NMR (CDCl₃): =0.62 (3H), 1.41-1.55 (2H), 1.75-1.86 (3H), 2.07 (1H), 2.10 (1H), 2.24-2.65 (9H), 2.74 (1H), 4.45 (1H), 5.25 (1H), 5.71 (1H), 5.79 (1H), 6.68 (1H), 7.05 (1H), 7.20-7.26 (3H) ppm.

EXAMPLE 19a (5R,8S,11R,13S,14S,17S)-1-(3-ethenylphenyl)-5',5',13-trimethyl-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

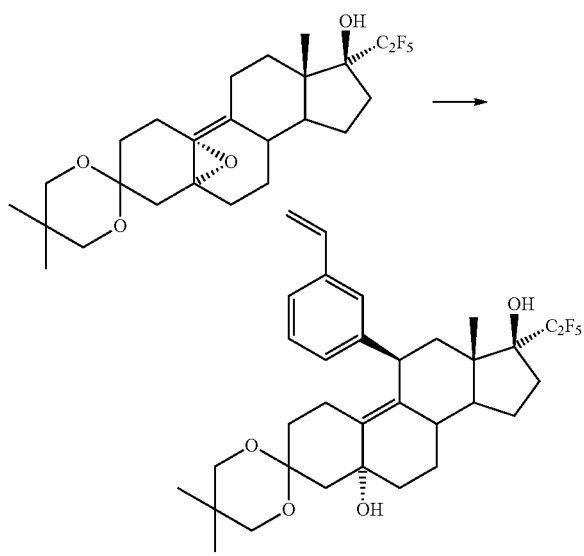

In analogy to Example 1a, 15 g (30.5 mmol) of (5R,8S,10R,13S,14S,17S)-17-(pentafluoroethyl)-5,10-epoxy-5',5',13-trimethyl-1,2,3,4,6,7,8,12,13,14,15,16,17-tridecahydrospiro[cyclopenta[a]phenanthrene-3,2'-[1,3]dioxan]-17-ol were reacted with the Grignard reagent prepared from 12 ml of 3-bromostyrene and, after workup and purification, 16.6 g (92%) of the title compound were isolated as a colourless foam.

EXAMPLE 20

(8S,11R,13S,14S,17S)-17-hydroxy-11-(3-isopropenylphenyl)-13-methyl-17-pentafluoroethyl-1,2,6,7,8,11,12,13,14,15,16,17-dodecahydrocyclopenta[a]phenanthren-3-one

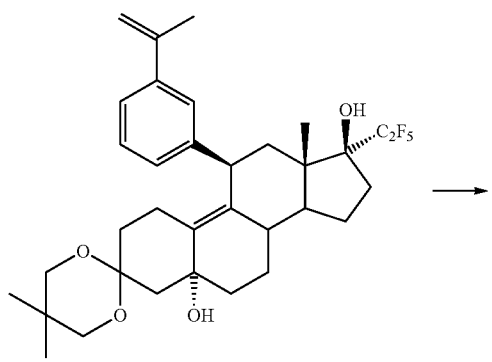

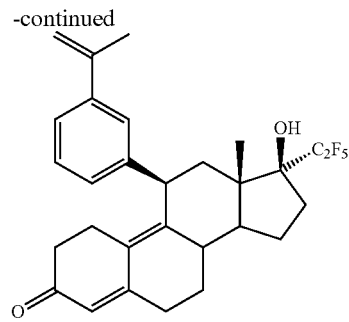

In analogy to Example 1, 250 mg (0.41 mmol) of the compound prepared according to Example 20a were converted and, after workup and purification, 164 mg (79%) of the title compound were isolated as a colourless foam.

¹H NMR (CDCl₃): =0.62 (3H), 1.41-1.56 (2H), 1.74-1.87 (3H), 2.05 (1H), 2.09 (1H), 2.13 (3H), 2.23-2.65 (9H), 2.75 (1H), 4.46 (1H), 5.08 (1H), 5.32 (1H), 5.79 (1H), 7.07 (1H), 7.20-7.31 (3H) ppm.

EXAMPLE 20a (5R,8S,11R,13S,14S,17S)-11-(3-isopropenylphenyl)-5',5',13-trimethyl-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

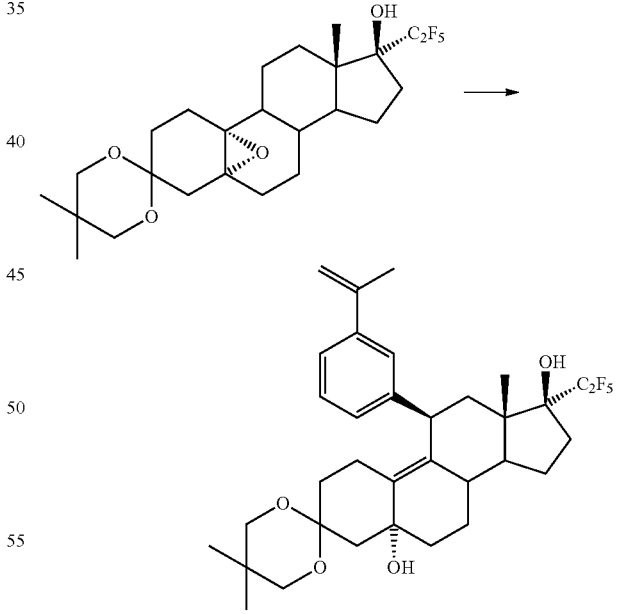

In analogy to Example 1a, 5.9 g (12.0 mmol) of (5R,8S,10R,13S,14S,17S)-17-(pentafluoroethyl)-5,10-epoxy-5',5',13-trimethyl-1,2,3,4,6,7,8,12,13,14,15,16,17-tridecahydrospiro[cyclopenta[a]phenanthrene-3,2'-[1,3]dioxan]-17-ol were reacted with the Grignard reagent prepared from 11.9 g of 1-bromo-3-isopropenylbenzene and, after workup and purification, 5.36 g (73%) of the title compound were isolated as a colourless foam.

EXAMPLE 21

(8S,11R,13S,14S,17S)-17-hydroxy-13-methyl-17-pentafluoroethyl-11-[3-((E)-2-pyridin-2-ylvinyl)phenyl]-1,2,6,7,8,11,12,13,14,15,16,17-dodecahydrocyclopenta[a]phenanthren-3-one

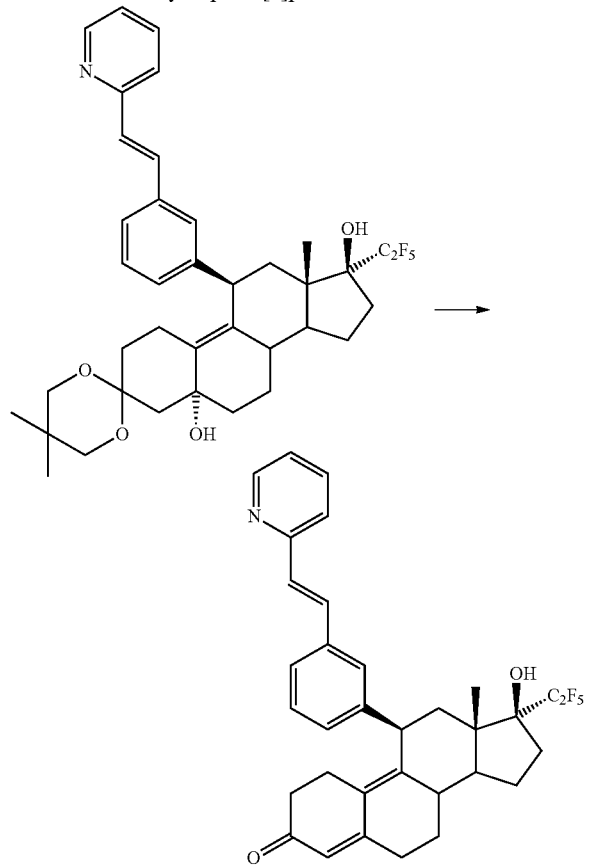

In analogy to Example 1, 70 mg (0.1 mmol) of the compound prepared according to Example 21a were converted and, after workup and purification, 45.4 mg (77%) of the title compound were isolated as a pale yellow foam.

$^1$H NMR (CDCl$_3$): =0.63 (3H), 1.42-1.56 (2H), 1.76-1.87 (3H), 2.08 (1H), 2.21 (1H), 2.26-2.67 (9H), 2.75 (1H), 4.47 (1H), 5.80 (1H), 7.10 (1H), 7.14 (1H), 7.17 (1H), 7.29 (1H), 7.36 (1H), 7.39 (1H), 7.43 (1H), 7.58 (1H), 7.68 (1H), 8.60 (1H) ppm.

EXAMPLE 21a (5R,8S,11R,13S,14S,17S)-5',5',13-trimethyl-17-(pentafluoroethyl)-11-{3-[(E)-2-(pyridin-2-yl)ethenyl]phenyl}-1,2,3,4,6,7,8,11,12,13,14,15,16,17-tetradecahydrospiro[cyclopenta[a]phenanthrene-3,2'-[1,3]dioxane]-5,17-diol

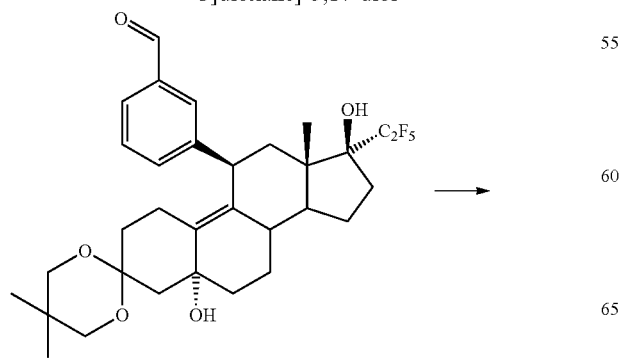

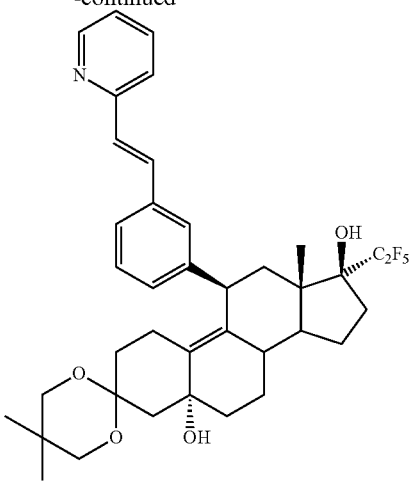

In analogy to Example 6a, 200 mg (0.33 mmol) of the compound prepared according to Example 21b were converted using diethyl pyridin-2-ylmethylphosphonate and, after workup and purification, 172 mg (76%) of the title compound were isolated as a yellow foam.

EXAMPLE 21B 3-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-1-yl)benzaldehyde

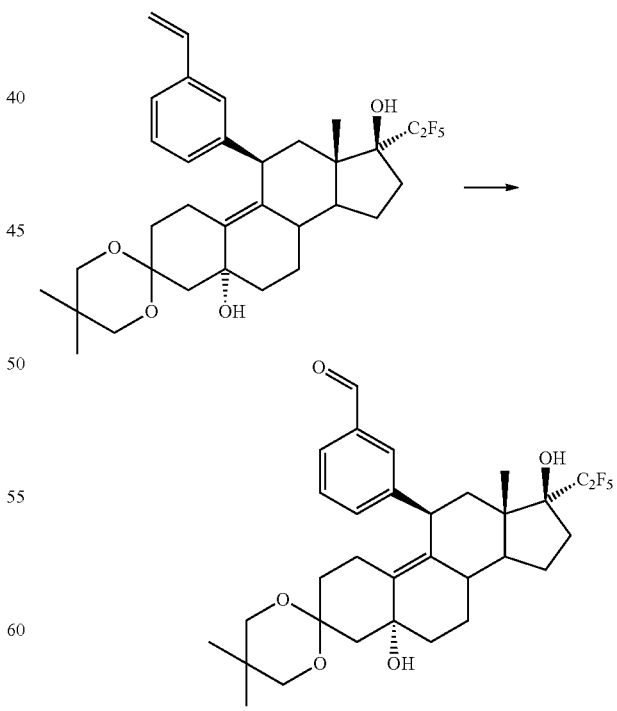

The solution of 5.0 g (8.38 mmol) of the compound prepared according to Example 19a in 250 ml of tetrahydrofuran was admixed with 20 ml of water, 1.25 ml of triethylamine, 5 ml of a saturated sodium hydrogencarbonate solution, 4.1 g of sodium periodate, 2.7 ml of a 40 mmolar solution of osmium tetroxide in tert-butanol, and the mixture was stirred at 23° C. After 5 hours, the addition of oxidizing agents was repeated and, after a further 16 hours, solid constituents were filtered off. They were rinsed with ethyl acetate and the combined organic phases were washed with semisaturated sodium thiosulphate solution and saturated sodium chloride solution. The residue obtained after filtration and removal of solvent was purified by crystallization from diisopropyl ether. 3.67 g (73%) of the title compound were isolated as a colourless foam.

EXAMPLE 22

(8S,11R,13S,14S,17S)-17-hydroxy-13-methyl-17-pentafluoroethyl-11-[3-((E)-2-pyridin-3-ylvinyl)phenyl]-1,2,6,7,8,11,12,13,14,15,16,17-dodecahydrocyclopenta[a]phenanthren-3-one In analogy to Example 1, 60 mg (89 μmol) of the compound prepared according to Example 22a were converted and, after workup and purification, 34.6 mg (68%) of the title compound were isolated as a pale yellow foam.

$^1$H NMR (CDCl$_3$): =0.72 (3H), 1.44-1.59 (2H), 1.79-1.91 (3H), 2.10 (1H), 2.24-2.67 (9H), 2.73 (1H), 4.44 (1H), 4.55 (1H), 5.80 (1H), 6.79 (1H), 6.86 (1H), 7.01 (1H), 7.20 (1H), 7.24-7.33 (2H), 7.36 (1H), 7.69 (1H), 8.49 (1H), 8.52 (1H) ppm.

EXAMPLE 22a (5R,8S,11R,13S,14S,17S)-5',5',13-trimethyl-17-(pentafluoroethyl)-11-{3-[(E)-2-(pyridin-3-yl)ethenyl]phenyl}-1,2,3,4,6,7,8,11,12,13,14,15,16,17-tetradecahydrospiro[cyclopenta[a]phenanthrene-3,2'-[1,3]dioxane]-5,17-diol

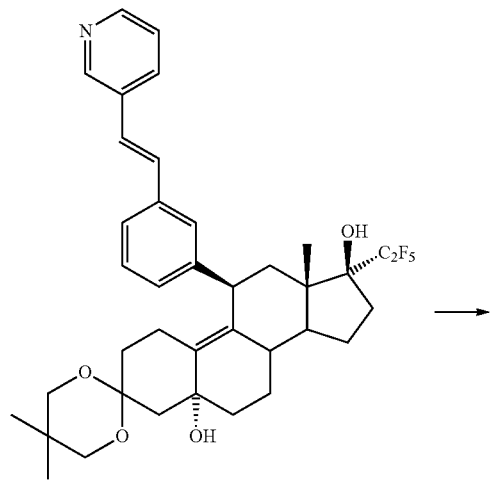

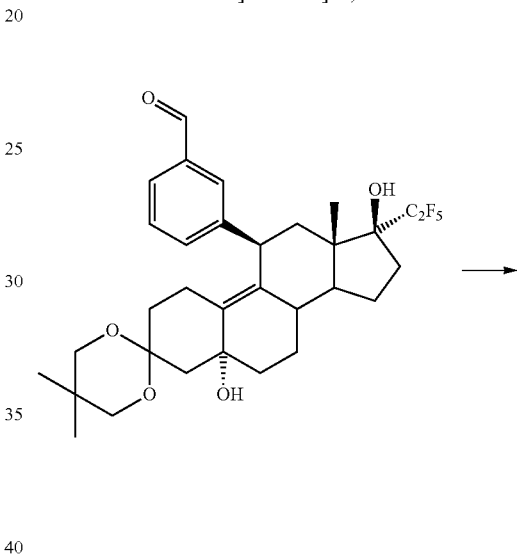

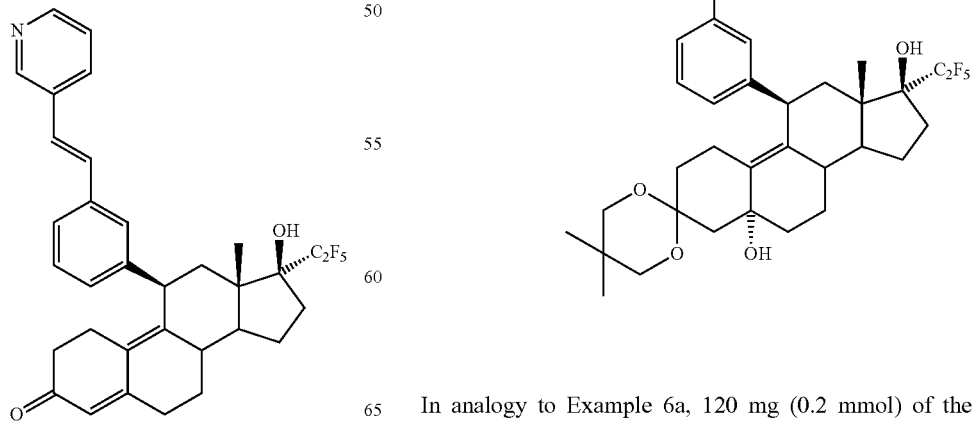

In analogy to Example 6a, 120 mg (0.2 mmol) of the compound prepared according to Example 21b were converted using diethyl pyridin-3-ylmethylphosphonate and, after workup and purification, 68 mg (50%) of the title compound were isolated as a pale yellow foam.

EXAMPLE 23

(8S,11R,13S,14S,17S)-17-hydroxy-13-methyl-17-pentafluoroethyl-11-[3-((E)-2-pyridin-4-ylvinyl)phenyl]-1,2,6,7,8,11,12,13,14,15,16,17-dodecahydrocyclopenta[a]phenanthren-3-one

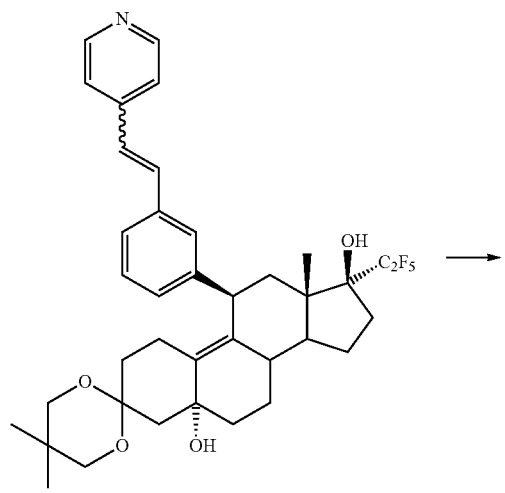

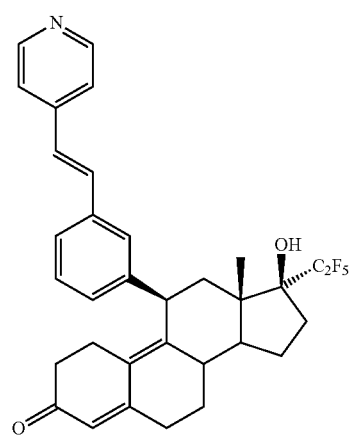

In analogy to Example 1, 70 mg (0.1 mmol) of a mixture of the compounds prepared according to Example 23a were converted and, after workup and purification, 38.4 mg (65%) of the title compound were isolated as a pale yellow foam.

$^1$H NMR (CDCl$_3$): =0.70 (3H), 1.45-1.57 (2H), 1.78-1.92 (3H), 2.10 (1H), 2.26-2.67 (8H), 2.70-2.80 (2H), 4.48 (1H), 5.80 (1H), 6.85 (1H), 7.03 (2H), 7.16 (1H), 7.28 (2H), 7.32 (2H), 7.40 (1H), 8.49 (2H) ppm.

EXAMPLE 23a (5R,8S,11R,13S,14S,17S)-5',5',13-trimethyl-17-(pentafluoroethyl)-11-{3-[(E/Z)-2-(pyridin-4-yl)ethenyl]phenyl}-1,2,3,4,6,7,8,11,12,13,14,15,16,17-tetradecahydrospiro[cyclopenta[a]phenanthrene-3,2'-[1,3]dioxane]-5,17-diol

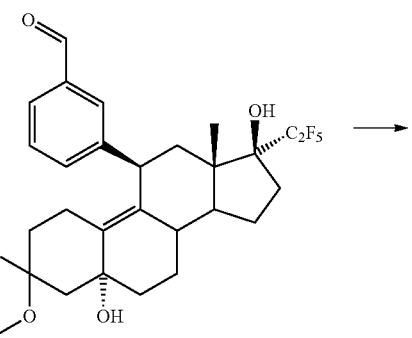

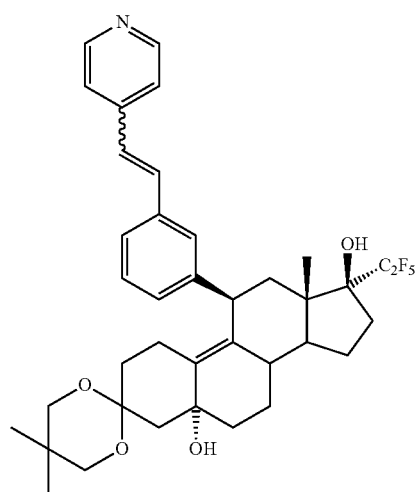

In analogy to Example 6a, 120 mg (0.2 mmol) of the compound prepared according to Example 21b were converted using diethyl pyridin-4-ylmethylphosphonate and, after workup and purification, 78 mg (58%) of the title compound were isolated as a pale yellow foam.

EXAMPLE 24

(8S,11R,13S,14S,17S)-17-hydroxy-13-methyl-11-
{3-[(E)-2-(2-methylthiazol-4-yl)vinyl]phenyl}-17-
pentafluoroethyl-1,2,6,7,8,11,12,13,14,15,16,17-
dodecahydrocyclopenta[a]phenanthren-3-one

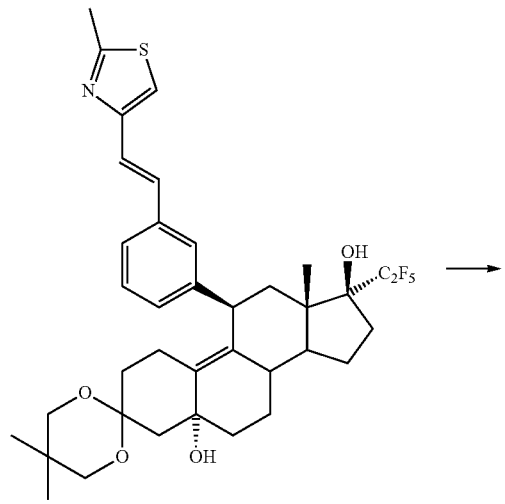

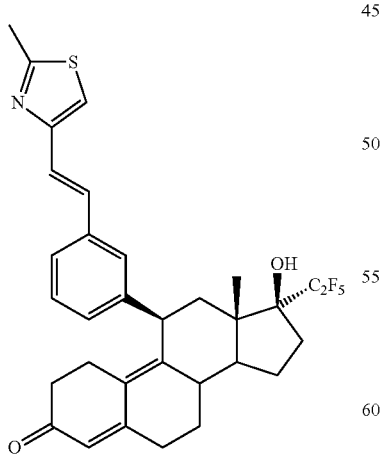

In analogy to Example 1, 62 mg (89 μmol) of the compound prepared according to Example 24a were converted and, after workup and purification, 37.6 mg (71%) of the title compound were isolated as a pale yellow foam.

$^1$H NMR (CDCl$_3$): =0.62 (3H), 1.42-1.55 (2H), 1.76-1.87 (3H), 2.06 (1H), 2.09 (1H), 2.25-2.66 (9H), 2.75 (4H), 4.46 (1H), 5.79 (1H), 6.99-7.09 (3H), 7.23-7.31 (2H), 7.35-7.41 (2H) ppm.

EXAMPLE 24a (5R,8S,11R,13S,14S,17S)-5',5',13-trimethyl-11-{3-
[(E)-2-(2-methyl-1,3-thiazol-4-yl)ethenyl]phenyl}-
17-(pentafluoroethyl)-1,2,3,4,6,7,8,11,12,13,14,15,
16,17-tetradecahydrospiro[cyclopenta[a]
phenanthrene-3,2'-[1,3]dioxane]-5,17-diol

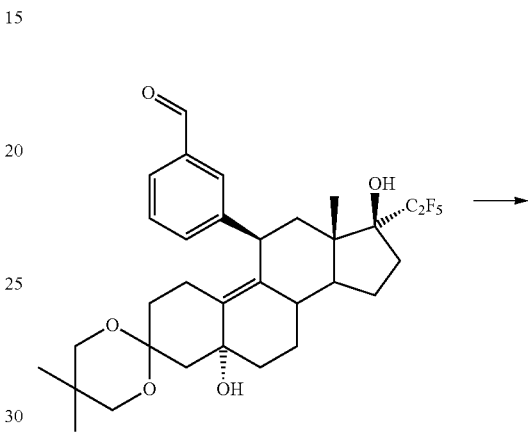

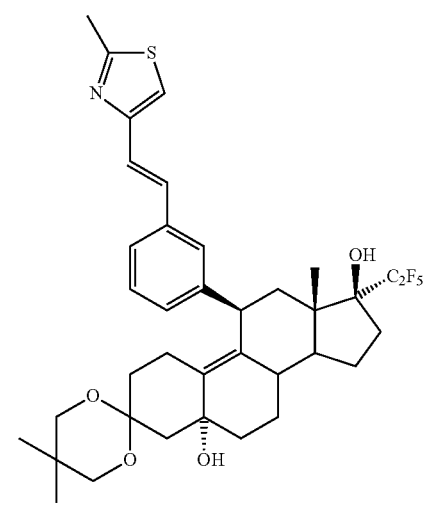

In analogy to Example 6a, 120 mg (0.2 mmol) of the compound prepared according to Example 21b were converted using diethyl (2-methylthiazol-4-ylmethyl)phosphonate and, after workup and purification, 70 mg (50%) of the title compound were isolated as a pale yellow foam.

EXAMPLE 25

(8S,11R,13S,14S,17S)-17-hydroxy-13-methyl-11-{3-[(E)-2-(2-methylbenzothiazol-5-yl)vinyl]phenyl}-17-pentafluoroethyl-1,2,6,7,8,11,12,13,14,15,16,17-dodecahydrocyclopenta[a]phenanthren-3-one

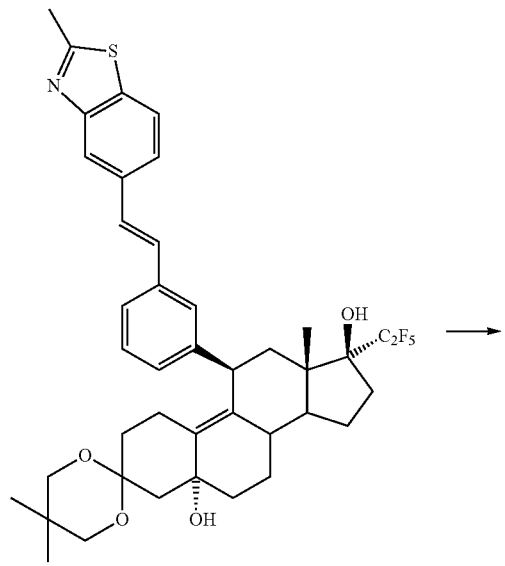

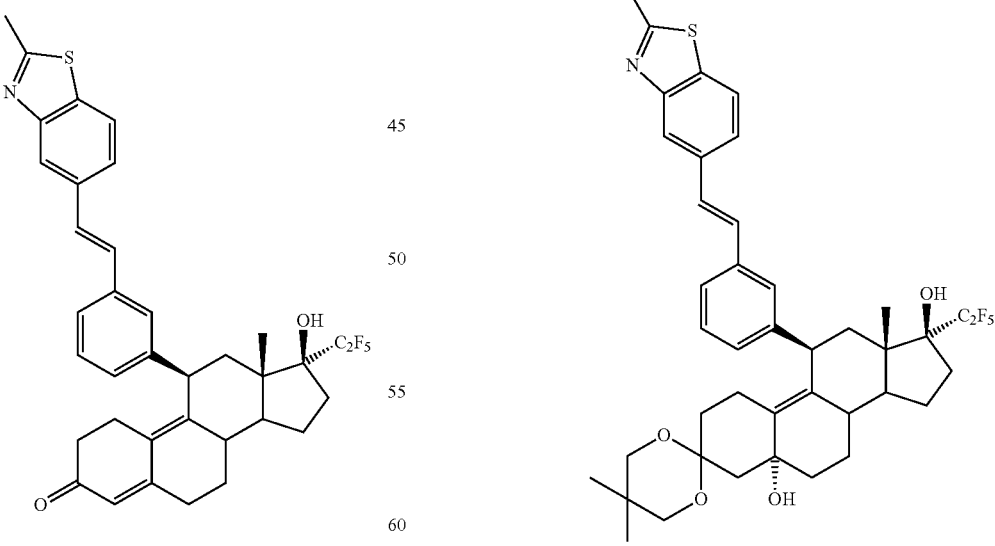

In analogy to Example 1, 51 mg (69 µmol) of the compound prepared according to Example 25a were converted and, after workup and purification, 23 mg (52%) of the title compound were isolated as a pale yellow foam.

$^1$H NMR (CDCl$_3$): =0.66 (3H), 1.43-1.57 (2H), 1.76-1.88 (3H), 2.09 (1H), 2.20 (1H), 2.27-2.67 (9H), 2.76 (1H), 2.85 (3H), 4.48 (1H), 5.80 (1H), 7.06 (1H), 7.12 (1H), 7.19 (1H), 7.29 (1H), 7.34 (1H), 7.39 (1H), 7.54 (1H), 7.79 (1H), 8.04 (1H) ppm.

EXAMPLE 25a (5R,8S,11R,13S,14S,17S)-5',5',13-trimethyl-11-{3-[(E)-2-(2-methyl-1,3-benzothiazol-5-yl)ethenyl]phenyl}-17-(pentafluoroethyl)-1,2,3,4,6,7,8,11,12,13,14,15,16,17-tetradecahydrospiro[cyclopenta[a]phenanthrene-3,2'-[1,3]dioxane]-5,17-diol

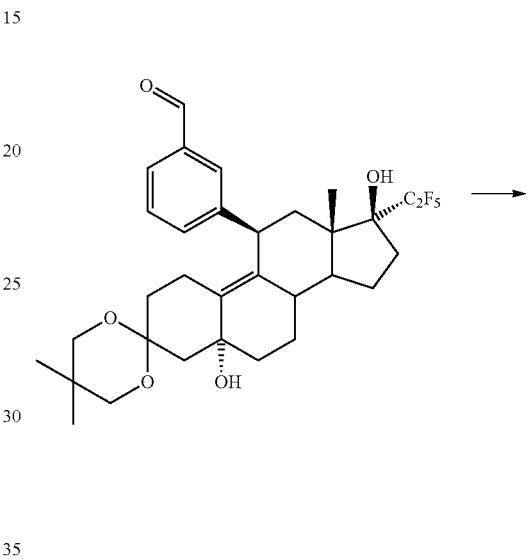

In analogy to Example 6a, 120 mg (0.2 mmol) of the compound prepared according to Example 21b were converted using diethyl (2-methylbenzothiazol-5-ylmethyl)

phosphonate and, after workup and purification, 70 mg (50%) of the title compound were isolated as a pale yellow foam.

EXAMPLE 26

(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]acrylic acid ethyl ester

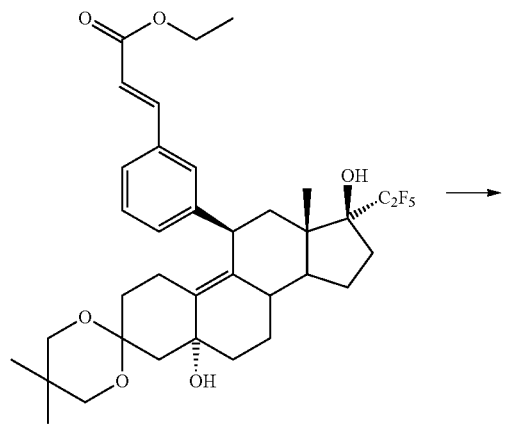

In analogy to Example 1, 163 mg (240 µmol) of the compound prepared according to Example 26a were converted and, after workup and purification, 101 mg (73%) of the title compound were isolated as a colourless foam.

$^1$H NMR (CDCl$_3$): =0.59 (3H), 1.34 (3H), 1.40-1.57 (2H), 1.74-1.87 (3H), 2.08 (1H), 2.16 (1H), 2.20-2.65 (9H), 2.74 (1H), 4.26 (2H), 4.46 (1H), 5.80 (1H), 6.40 (1H), 7.18 (1H), 7.27-7.39 (3H), 7.64 (1H) ppm.

EXAMPLE 26a (E)-3-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-11-yl)phenyl]acrylic acid ethyl ester

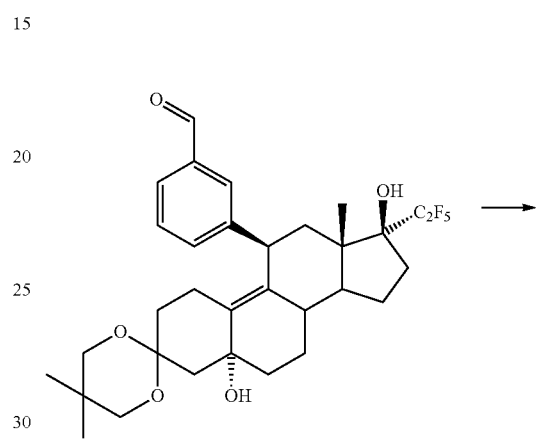

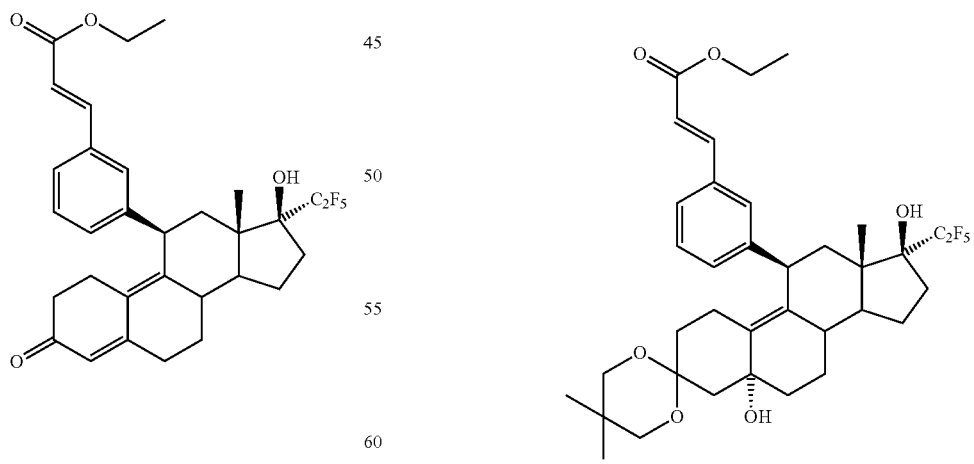

In analogy to Example 6a, 200 mg (0.33 mmol) of the compound prepared according to Example 21b were converted using ethyl(diethoxyphosphoryl)acetate and, after workup and purification, 171 mg (77%) of the title compound were isolated as a colourless foam.

EXAMPLE 27

2-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}malonitrile

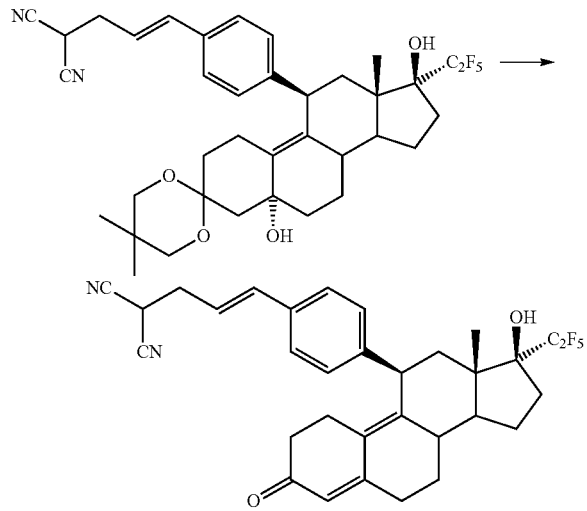

In analogy to Example 1, 27 mg (40 µmol) of the compound prepared according to Example 27a were converted and, after workup and purification, 14 mg (59%) of the title compound were isolated as a colourless foam.

$^1$H NMR (CDCl$_3$): =0.61 (3H), 1.42-1.55 (2H), 1.75-1.86 (3H), 2.03-2.11 (2H), 2.22-2.64 (9H), 2.73 (1H), 2.92 (2H), 3.84 (1H), 4.44 (1H), 5.79 (1H), 6.15 (1H), 6.67 (1H), 7.16 (2H), 7.32 (2H) ppm.

EXAMPLE 27a

2-{(E)-3-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-1-yl)phenyl]allyl}malonitrile

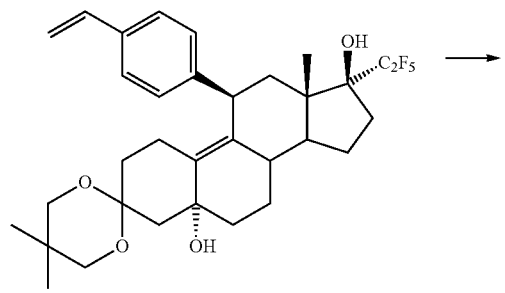

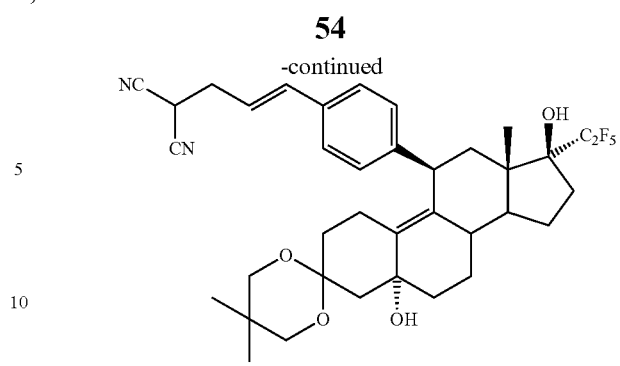

In analogy to Example 2a, 500 mg (0.84 mmol) of the compound prepared according to Example 1a were converted using allylmalonitrile and, after workup and purification, 93 mg (16%) of the title compound were isolated as a colourless foam.

EXAMPLE 28

3-{(E)-2-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]vinyl}benzoic acid

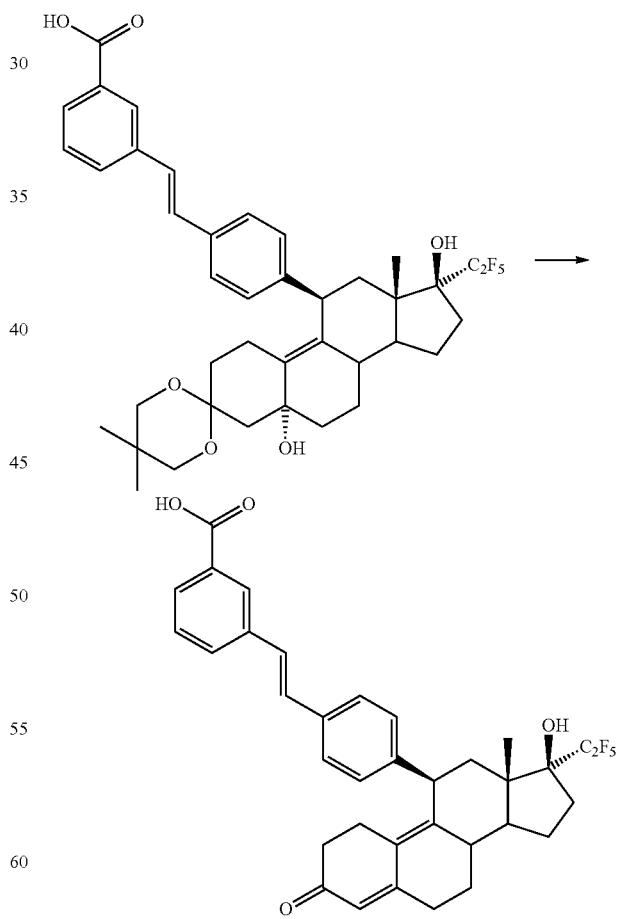

In analogy to Example 1, 1.36 g (1.67 mmol) of the compound prepared according to Example 28a were converted and, after workup and purification, 480 mg (47%) of the title compound were isolated as a colourless foam.

¹H NMR (CD₃OD): =0.61 (3H), 1.34-1.56 (2H), 1.69-1.83 (3H), 2.07 (1H), 2.18-2.46 (5H), 2.52-2.70 (4H), 2.80 (1H), 4.47 (1H), 5.71 (1H), 6.60 (2H), 7.06-7.30 (6H), 7.76 (1H), 7.84 (1H) ppm.

EXAMPLE 28a

3-{(E)-2-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-1-yl)phenyl]vinyl}benzoic acid

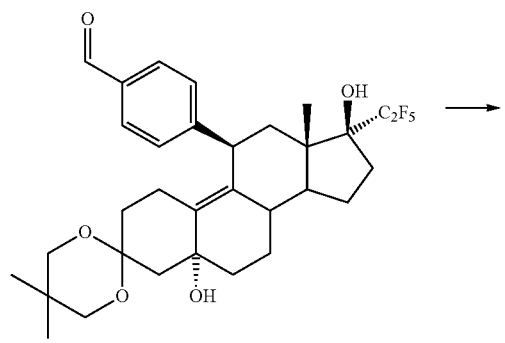

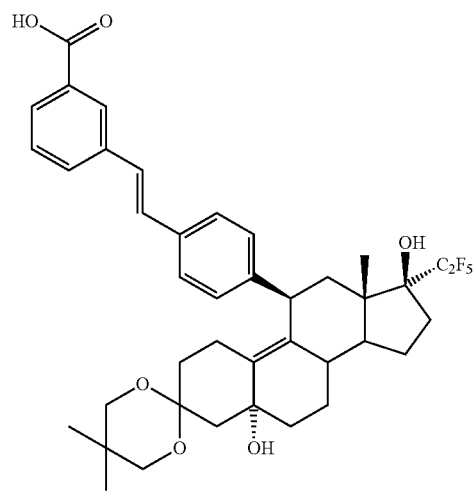

In analogy to Example 6a, 500 mg (0.84 mmol) of the compound prepared according to Example 28b were converted using 3-(diethoxyphosphorylmethyl)benzoic acid and, after workup and purification, 48 mg (9%) of the title compound were isolated as a colourless foam.

EXAMPLE 28B 4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-11-yl)benzaldehyde

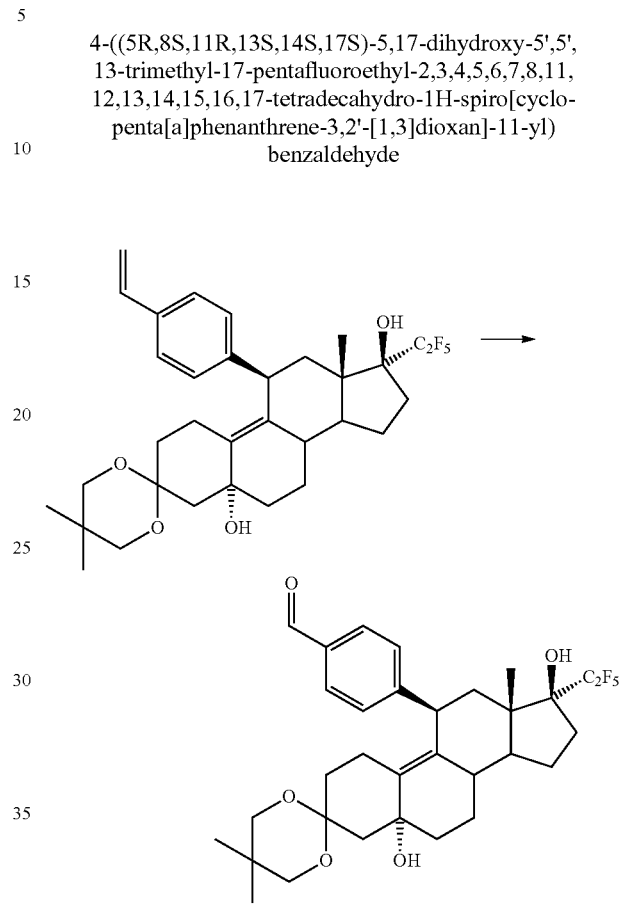

In analogy to Example 21b, 3.99 g (6.69 mmol) of the compound prepared according to Example 1a were converted and, after workup and purification, 3.56 g (89%) of the title compound were isolated as a colourless foam.

EXAMPLE 29

4-{(E)-2-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]vinyl}benzoic acid

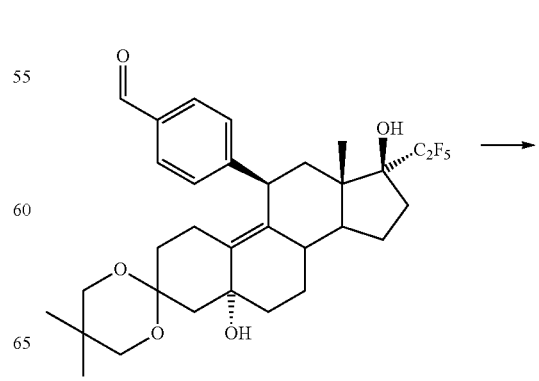

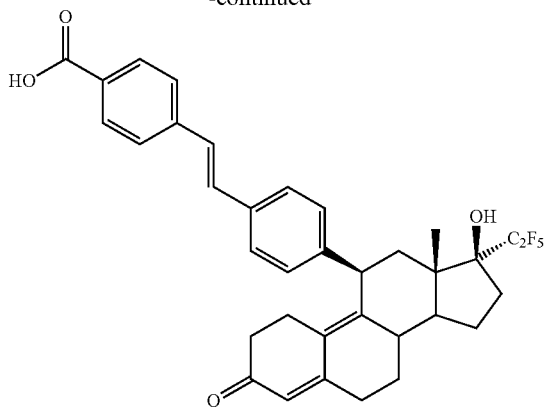

In analogy to Example 6a, 500 mg (0.84 mmol) of the compound prepared according to Example 28b were converted using 4-(diethoxyphosphorylmethyl)benzoic acid and, after workup and purification, 105 mg (21%) of the title compound were isolated as a colourless foam.

$^1$H NMR (CDCl$_3$): =0.63 (3H), 1.22-1.33 (2H), 1.40-1.58 (2H), 1.73-1.88 (3H), 2.08 (1H), 2.24-2.66 (9H), 2.75 (1H), 4.46 (1H), 5.81 (1H), 7.09 (1H), 7.16-7.24 (3H), 7.46 (2H), 7.58 (2H), 8.09 (2H) ppm.

EXAMPLE 30

3-{(E)-2-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]vinyl}benzoic acid methyl ester

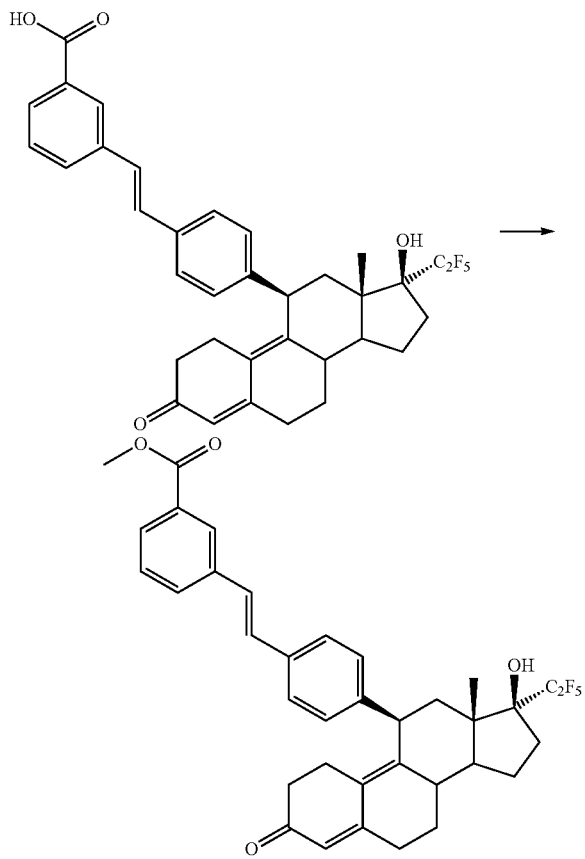

The solution of 24 mg (39 µmol) of the compound prepared according to Example 28 in 1 ml of tetrahydrofuran was admixed at 3° C. with 0.8 ml of an ethereal solution of diazomethane, and the mixture was stirred for 30 minutes. The residue obtained after removal of solvent was purified by chromatography, and 18 mg (75%) of the title compound were isolated as a colourless foam.

$^1$H NMR (CDCl$_3$): =0.64 (3H), 1.41-1.56 (2H), 1.75-1.87 (3H). 2.07 (1H), 2.26-2.69 (10H), 2.75 (1H), 3.94 (3H), 4.46 (1H), 5.79 (1H), 7.11 (2H), 7.18 (2H), 7.39-7.46 (3H), 7.67 (1H), 7.91 (1H), 8.18 (1H) ppm.

EXAMPLE 31

4-{(E)-2-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]vinyl}benzoic acid methyl ester

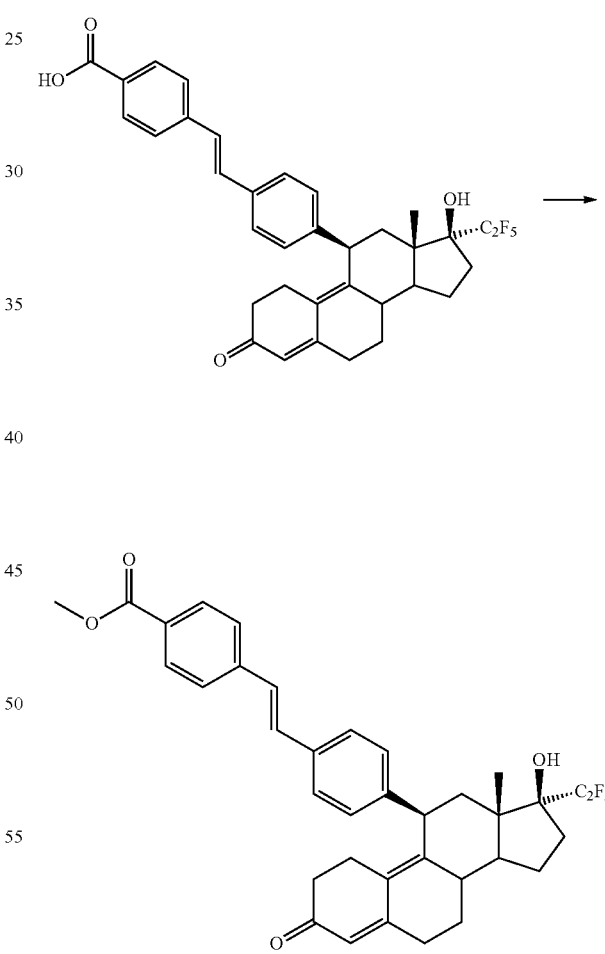

In analogy to Example 30, 13 mg (21 µmol) of the compound prepared according to Example 29 were converted and, after workup and purification, 12 mg (90%) of the title compound were isolated as a colourless foam.

$^1$H NMR (CDCl$_3$): =0.63 (3H), 1.44-1.56 (2H), 1.74-1.87 (3H), 2.07 (1H), 2.17 (1H), 2.25-2.66 (9H), 2.75 (1H), 3.92

(3H), 4.46 (1H), 5.80 (1H), 7.09 (1H), 7.17 (1H), 7.19 (2H), 7.45 (2H), 7.55 (2H), 8.01 (2H) ppm.

¹H NMR (CDCl₃): =0.63 (3H), 1.42-1.56 (2H), 1.75-1.87 (3H), 2.08 (1H), 2.21-2.68 (10H), 2.75 (1H), 3.07 (3H), 4.47 (1H), 5.80 (1H), 7.09 (1H), 7.16-7.24 (3H), 7.45 (2H), 7.66 (2H), 7.90 (2H) ppm.

EXAMPLE 32

(8S,11R,13S,14S,17S)-17-hydroxy-11-{4-[(E)-2-(4-methanesulphonylphenyl)vinyl]phenyl}-13-methyl-17-pentafluoroethyl-1,2,6,7,8,11,12,13,14,15,16,17-dodecahydrocyclopenta[a]phenanthren-3-one

EXAMPLE 32a (5R,8S,11R,13S,14S,17S)-11-{4-[(E)-2-(4-methanesulphonylphenyl)vinyl]phenyl}-5',5',13-trimethyl-17-pentafluoroethyl-1,2,3,4,6,7,8,11,12,13,14,15,16,17-tetradecahydrospiro[cyclopenta[a]phenanthrene-3,2'-[1,3]dioxane]-5,17-diol

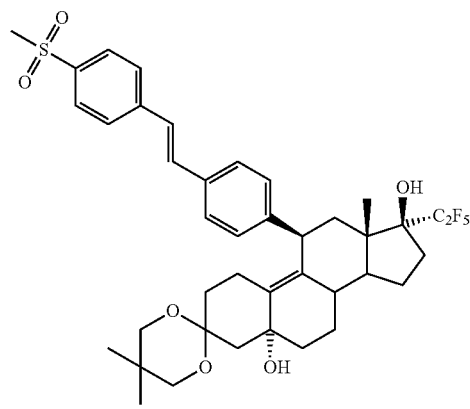

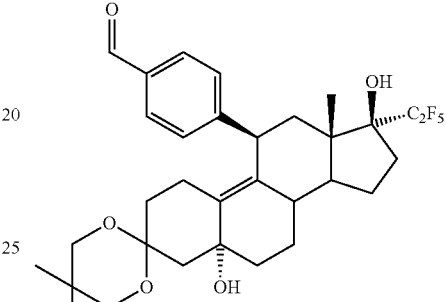 

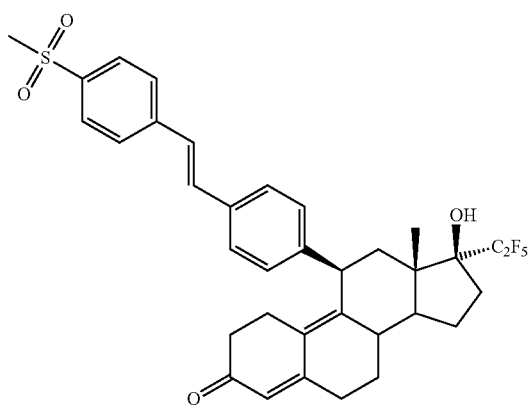

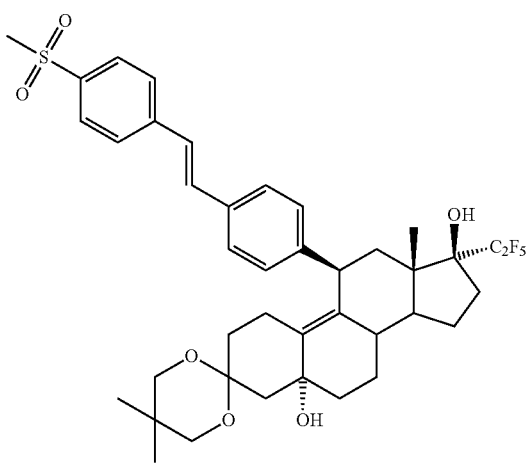

In analogy to Example 1, 25 mg (33 µmol) of the compound prepared according to Example 32a were converted and, after workup and purification, 11 mg (52%) of the title compound were isolated as a colourless foam.

In analogy to Example 6a, 200 mg (0.33 mmol) of the compound prepared according to Example 28b were converted using diethyl (4-methanesulphonylbenzyl)phosphonate and, after workup and purification, 198 mg (79%) of the title compound were isolated as a colourless foam.

EXAMPLE 33

(8S,11R,13S,14S,17S)-17-hydroxy-13-methyl-11-{4-[(E)-2-(4-methylsulphanylphenyl)vinyl]phenyl}-17-pentafluoroethyl-1,2,6,7,8,11,12,13,14,15,16,17-dodecahydrocyclopenta[a]phenanthren-3-one

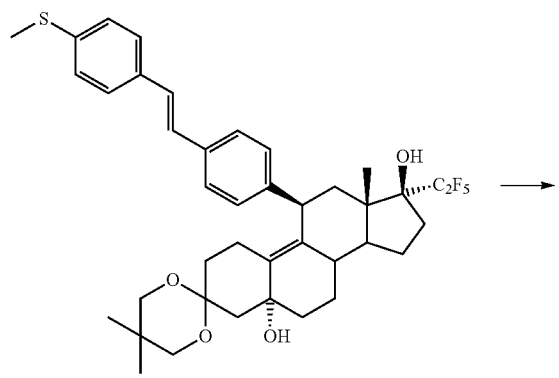

In analogy to Example 1, 25 mg (35 μmol) of the compound prepared according to Example 33a were converted and, after workup and purification, 10 mg (48%) of the title compound were isolated as a colourless foam.

$^1$H NMR (CDCl$_3$): =0.63 (3H), 1.41-1.56 (2H), 1.74-1.87 (3H), 2.07 (1H), 2.10 (1H), 2.25-2.65 (9H), 2.50 (3H), 2.75 (1H), 4.45 (1H), 5.79 (1H), 7.02 (2H), 7.16 (2H), 7.23 (2H), 7.42 (4H) ppm.

EXAMPLE 33a (5R,8S,11R,13S,14S,17S)-11-{4-[(E)-2-(4-methylsulphanylphenyl)vinyl]phenyl}-5',5',13-trimethyl-17-pentafluoroethyl-1,2,3,4,6,7,8,11,12,13,14,15,16,17-tetradecahydrospiro[cyclopenta[a]phenanthrene-3,2'-[1,3]dioxane]-5,17-diol

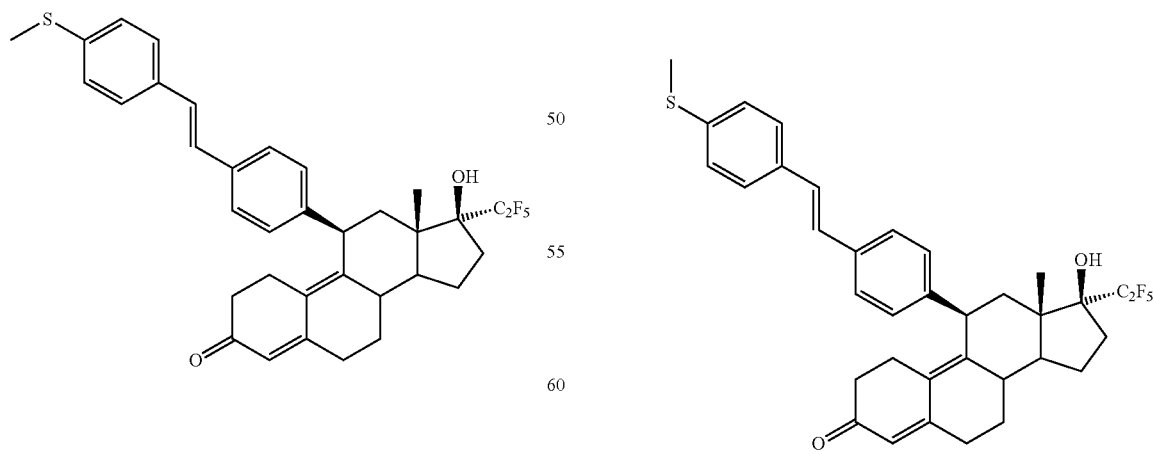

In analogy to Example 6a, 200 mg (0.33 mmol) of the compound prepared according to Example 28b were converted using diethyl (4-methylsulphanylbenzyl)phosphonate and, after workup and purification, 175 mg (73%) of the title compound were isolated as a colourless foam.

EXAMPLE 34

[1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]meth-(E)-ylideneaminooxy]acetic acid

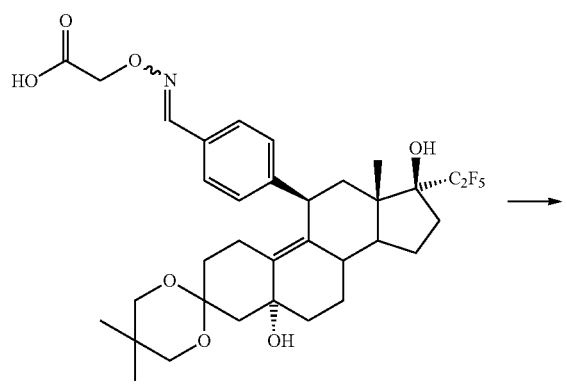

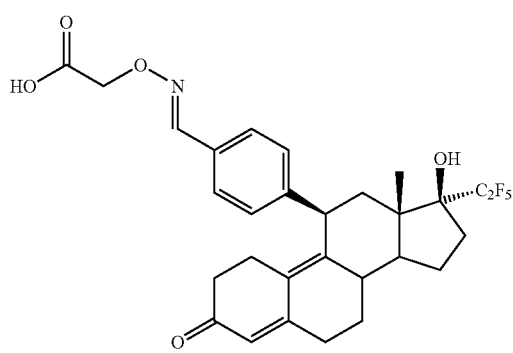

In analogy to Example 1, 59.6 mg (89 μmol) of the compound prepared according to Example 34a were converted and, after workup and purification, 39 mg (77%) of the title compound were isolated as a colourless foam.

$^1$H NMR (CD$_3$OD): =0.59 (3H), 1.35-1.59 (2H), 1.69-1.85 (3H), 2.10 (1H), 2.16-2.48 (5H), 2.55-2.74 (4H), 2.81 (1H), 4.55 (1H), 4.65 (2H), 5.75 (1H), 7.29 (2H), 7.54 (2H), 8.16 (1H) ppm.

EXAMPLE 34a

[1-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-11-yl)phenyl]meth-(E/Z)-ylideneaminooxy]acetic acid

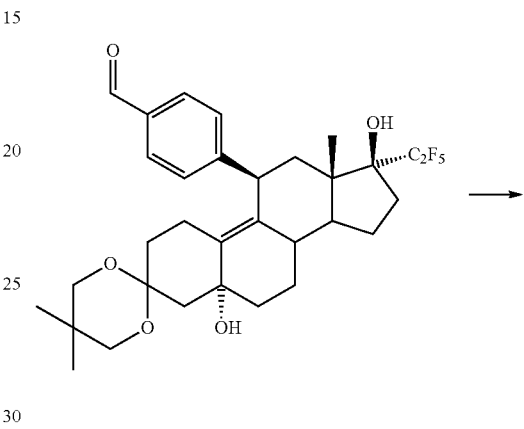

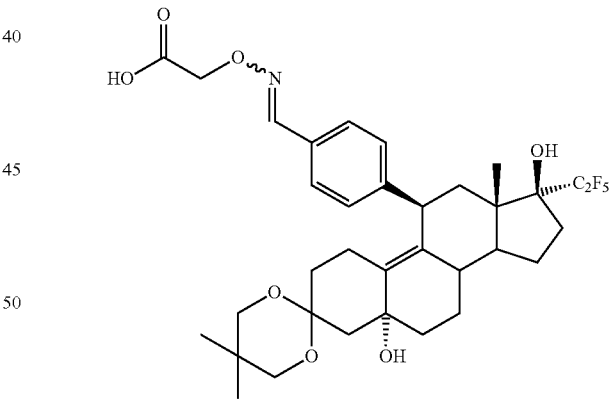

The suspension of 31.7 mg of aminooxyacetic acid hydrochloride in 2.5 ml of tetrahydrofuran was admixed at 23° C. with 230 μl of a 2.5 molar solution of n-butyllithium in hexane and, after 20 minutes, with the solution of 100 mg (0.17 mmol) of the compound prepared according to Example 28b in 1 ml of tetrahydrofuran. The mixture was heated to 55° C. for 2.5 hours and left to react at 23° C. for a further 16 hours. It was poured into water, acidified by addition of 1 molar hydrochloric acid and extracted repeatedly with ethyl acetate. The combined organic extracts were washed with water, saturated sodium chloride solution, saturated sodium hydrogencarbonate solution, and dried over sodium sulphate. The residue obtained after filtration and solvent removal was purified by chromatography. 60 mg (53%) of the title compound were isolated as a colourless foam.

EXAMPLE 35

4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzaldehyde O-benzyl oxime

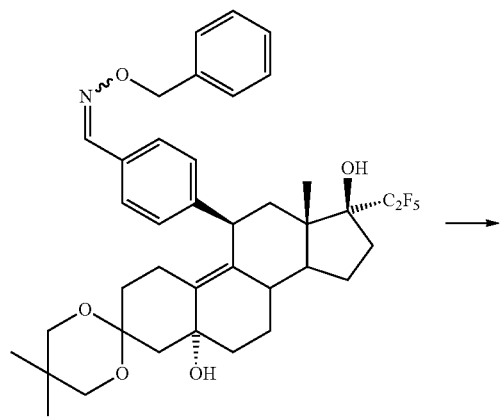

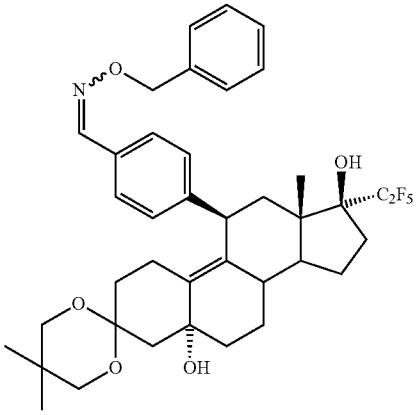

In analogy to Example 1, 86.9 mg (0.12 mmol) of the compound prepared according to Example 35a were converted and, after workup and purification, 51 mg (69%) of the title compound were isolated as a colourless foam.

$^1$H NMR (CDCl$_3$): =0.59 (3H), 1.42-1.54 (2H), 1.74-1.86 (3H), 2.06 (2H), 2.21-2.63 (9H), 2.72 (1H), 4.44 (1H), 5.19 (2H), 5.79 (1H), 8.18 (2H), 7.29-7.44 (5H), 7.50 (2H), 8.10 (1H) ppm.

EXAMPLE 35a 4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-11-yl)benzaldehyde O-benzyl oxime

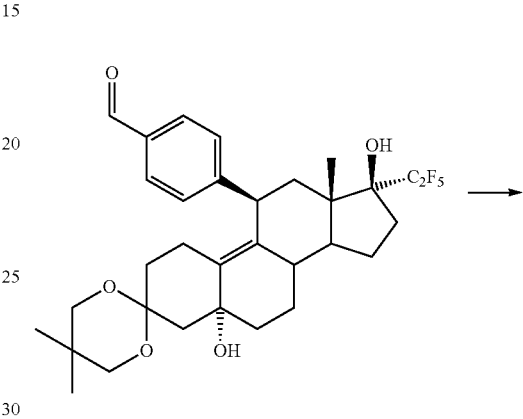

In analogy to Example 34a, 100 mg (0.17 mmol) of the compound prepared according to Example 28b were converted using O-benzylhydroxylamine hydrochloride and, after workup and purification, 87 mg (94%) of the title compound were isolated as a colourless foam.

$^1$H NMR (CDCl$_3$): =0.59 (3H), 1.31 (3H), 1.38-1.58 (2H), 1.71-1.88 (3H), 2.07 (1H), 2.18-2.65 (10H), 2.72 (1H), 4.20 (2H), 4.44 (1H), 5.78 (1H), 7.17 (2H), 7.50 (2H), 8.03 (1H) ppm.

EXAMPLE 36

4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzaldehyde O-ethyl oxime

EXAMPLE 36a 4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-11-yl)benzaldehyde O-ethyl oxime

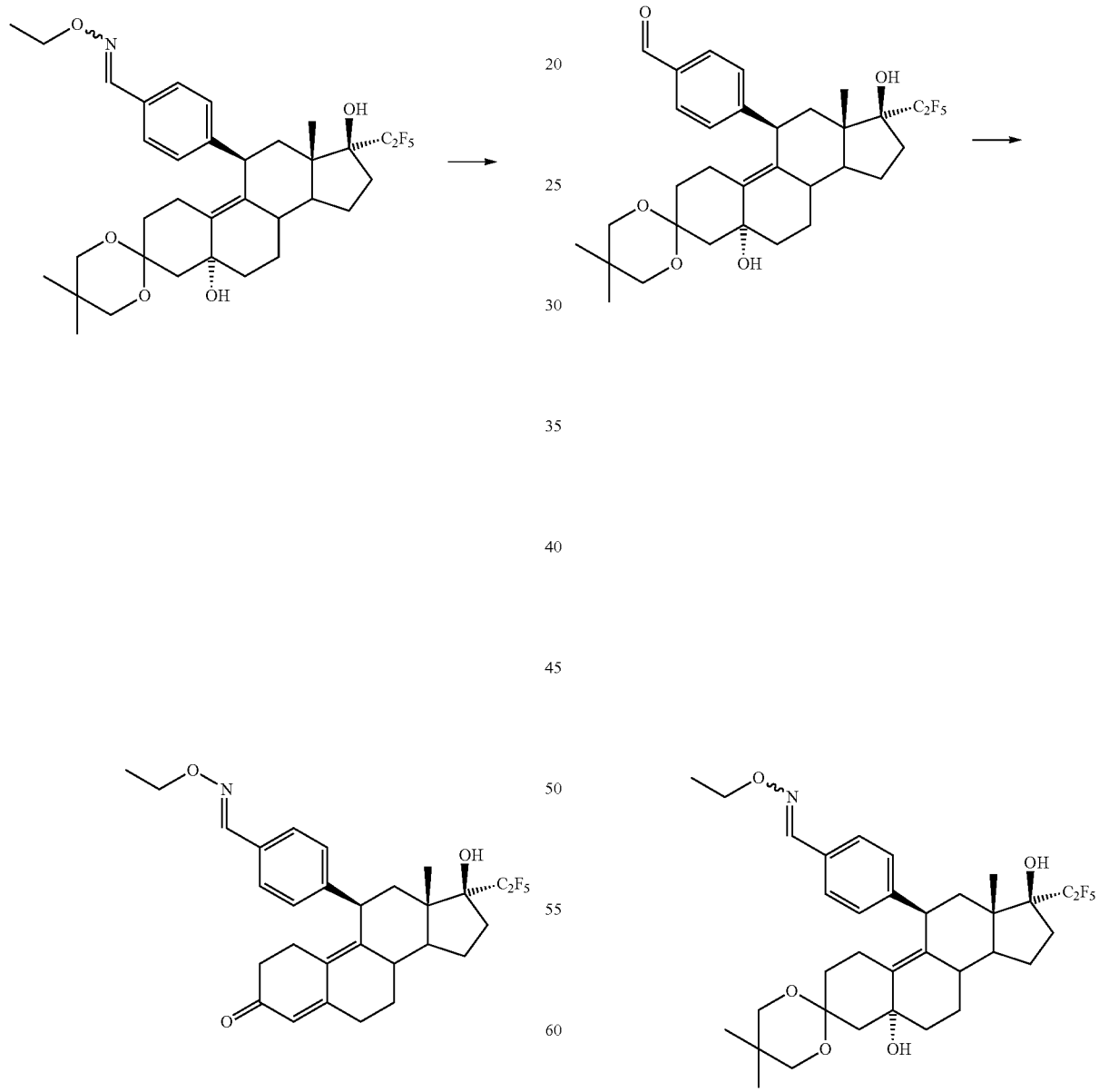

In analogy to Example 1, 40 mg (62 μmol) of the compound prepared according to Example 36a were converted and, after workup and purification, 19.7 mg (59%) of the title compound were isolated as a colourless foam.

In analogy to Example 34a, 100 mg (0.17 mmol) of the compound prepared according to Example 28b were converted using O-ethylhydroxylamine hydrochloride and, after workup and purification, 40 mg (37%) of the title compound were isolated as a colourless foam.

EXAMPLE 37

4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzaldehyde O-(3,4-dichlorobenzyl)oxime

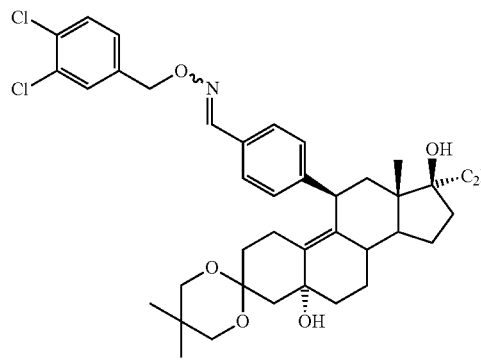

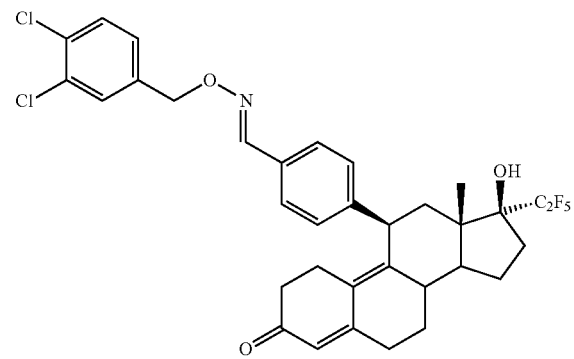

In analogy to Example 1, 105 mg (0.14 mmol) of the compound prepared according to Example 37a were converted and, after workup and purification, 50 mg (55%) of the title compound were isolated as a colourless foam.

$^1$H NMR (CDCl$_3$): =0.59 (3H), 1.39-1.55 (2H), 1.74-1.88 (3H), 2.04 (1H), 2.06 (1H), 2.21-2.63 (9H), 2.72 (1H), 4.45 (1H), 5.12 (2H), 5.79 (1H), 7.14-7.25 (3H), 7.43 (1H), 7.45-7.55 (3H), 8.09 (1H) ppm.

EXAMPLE 37a 4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-11-yl)benzaldehyde O-(3,4-dichlorobenzyl)oxime

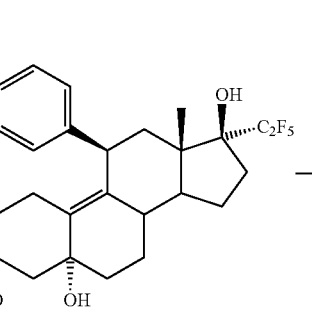

In analogy to Example 34a, 100 mg (0.17 mmol) of the compound prepared according to Example 28b were converted using O-(3,4-dichlorobenzyl)hydroxylamine hydrochloride and, after workup and purification, 105 mg (81%) of the title compound were isolated as a colourless foam.

EXAMPLE 38

4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzaldehyde O-isobutyl oxime

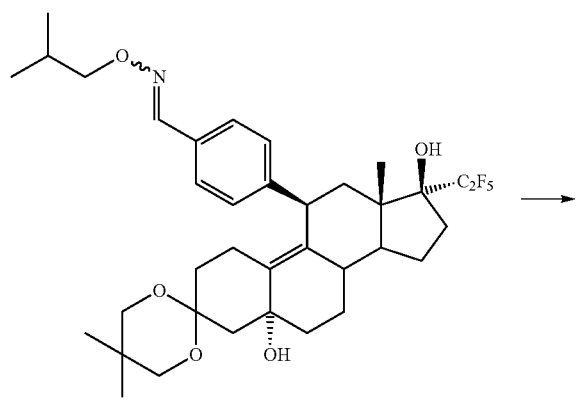

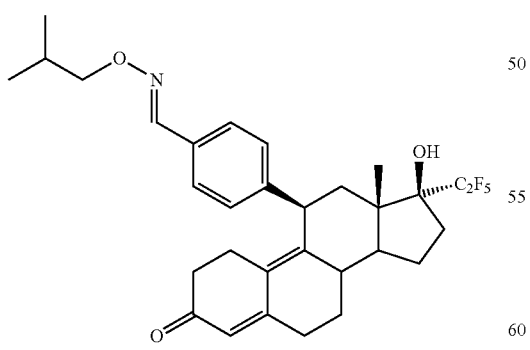

In analogy to Example 1, 58 mg (86 μmol) of the compound prepared according to Example 38a were converted and, after workup and purification, 28 mg (58%) of the title compound were isolated as a colourless foam.

$^1$H NMR (CDCl$_3$): =0.59 (3H), 0.95 (6H), 1.41-1.54 (2H), 1.74-1.86 (3H), 1.99-2.10 (3H), 2.22-2.65 (9H), 2.72 (1H), 3.93 (2H), 4.45 (1H), 5.79 (1H), 7.18 (2H), 7.50 (2H), 8.06 (1H) ppm.

EXAMPLE 38a 4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-11-yl)benzaldehyde O-isobutyl oxime

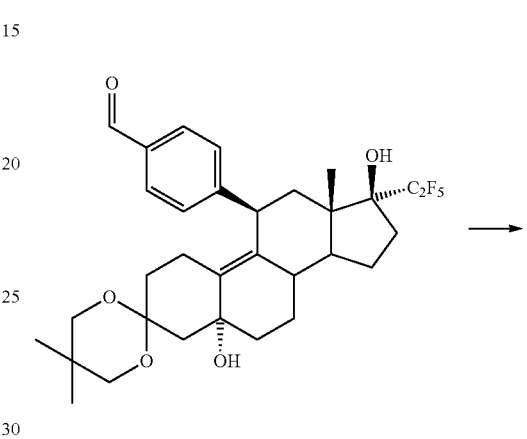

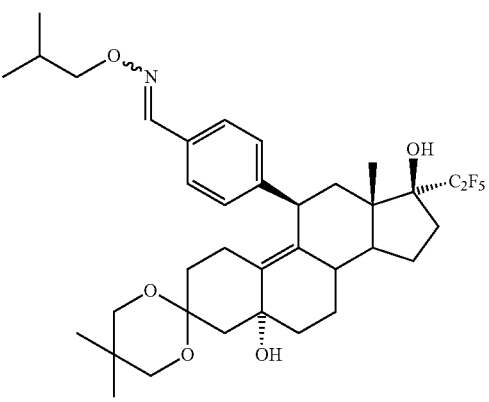

In analogy to Example 34a, 100 mg (0.17 mmol) of the compound prepared according to Example 28b were converted using O-isobutylhydroxylamine hydrochloride and, after workup and purification, 58 mg (52%) of the title compound were isolated as a colourless foam.

EXAMPLE 39

1-ethyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea

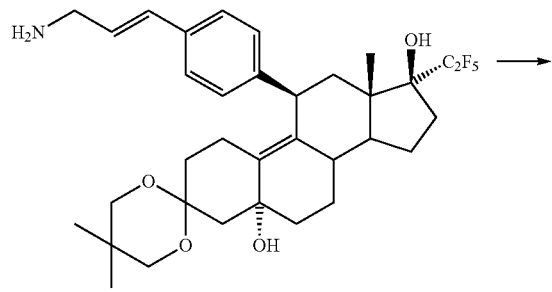

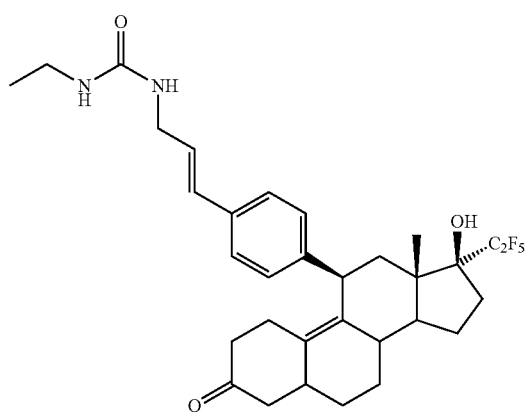

The solution of 40 mg (53 µmol) of the compound prepared according to Example 39a in 1 ml of dichloromethane was admixed with 5 µl of ethyl isocyanate and stirred at 23° C. for 1 hour. The mixture was concentrated and dissolved in 1 ml of acetone, 70 µl of 4 molar hydrochloric acid were added and the mixture was stirred for 1 hour. Saturated sodium hydrogencarbonate solution was added, and the mixture was extracted with dichloromethane and dried over sodium sulphate. The residue obtained after filtration and removal of solvent was purified by chromatography. 17 mg (54%) of the title compound were isolated as a colourless foam.

$^1$H NMR (CDCl$_3$): =0.60 (3H), 1.09 (3H), 1.39-1.55 (2H), 1.69-1.89 (3H), 2.05 (1H), 2.19-2.65 (9H), 2.72 (1H), 3.09- 3.27 (3H), 3.89 (2H), 4.41 (1H), 4.68 (1H), 4.80 (1H), 5.76 (1H), 6.12 (1H), 6.42 (1H), 7.10 (2H), 7.22 (2H) ppm.

EXAMPLE 39a (5R,8S,11R,13S,14S,17S)-11-[4-((E)-3-aminopropenyl)phenyl]-5',5',13-trimethyl-17-pentafluoroethyl-1,2,3,4,6,7,8,11,12,13,14,15,16,17-tetradecahydrospiro[cyclopenta[a]phenanthrene-3,2'-[1,3]dioxane]-5,17-diol

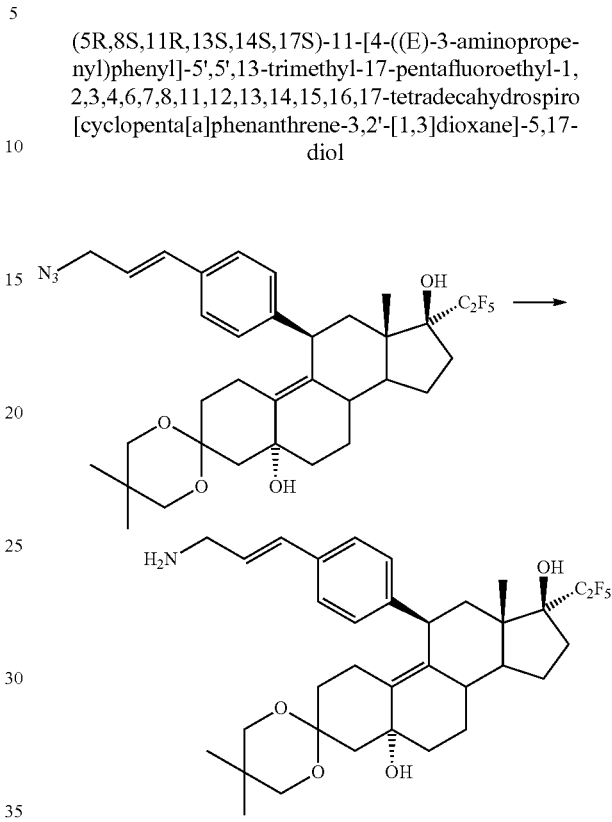

The solution of 778 g (1.19 mmol) of the compound prepared according to Example 39b in 20 ml of tetrahydrofuran was admixed with 3.3 ml of water, 0.24 ml of trimethylphosphine, and stirred at 23° C. for 4 hours. 2.5 ml of a 25% ammonia solution were added, and the mixture was stirred at 23° C. for a further 16 hours and concentrated. The title compound obtained as a crude product was converted further without purification.

EXAMPLE 39B (5R,8S,11R,13S,14S,17S)-1-[4-((E)-3-azidopropenyl)phenyl]-5',5',13-trimethyl-17-pentafluoroethyl-1,2,3,4,6,7,8,11,12,13,14,15,16,17-tetradecahydrospiro[cyclopenta[a]phenanthrene-3,2'-[1,3]dioxane]-5,17-diol

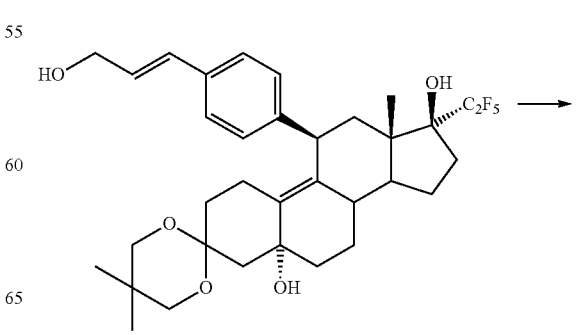

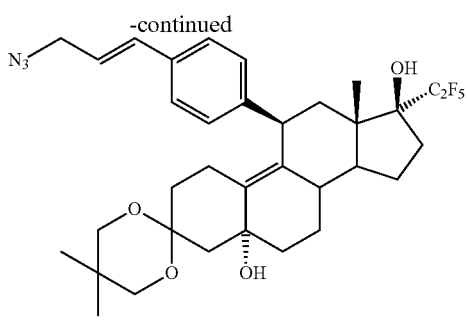

The solution of 800 mg (1.28 mmol) of the compound prepared according to Example 2a in 20 ml of tetrahydrofuran was admixed at 3° C. with 0.38 ml of diphenylphosphoryl azide, 0.22 ml of 1,8-diazabicyclo[5.4.0]undec-7-ene, and the mixture was left to react at 23° C. for 4 hours and at 23° C. for a further 16 hours. Water was added to the mixture, which was extracted repeatedly with ethyl acetate, and the combined organic extracts were washed with saturated sodium chloride solution and dried over sodium sulphate. The residue obtained after filtration and solvent removal was purified by chromatography. 785 mg (94%) of the title compound were isolated as a colourless foam.

EXAMPLE 40

1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]-3-isopropylurea

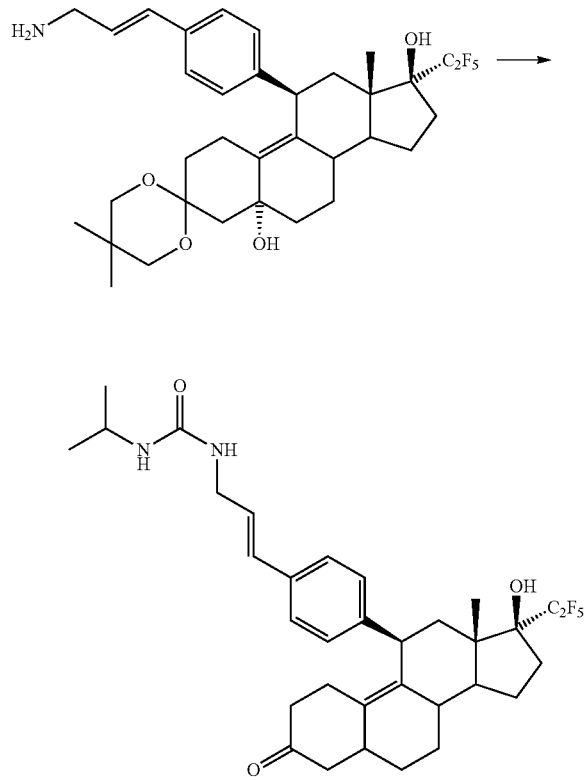

In analogy to Example 39, 40 mg (53 μmol) of the compound prepared according to Example 39a were converted using isopropyl isocyanate and, after workup and purification, 16 mg (50%) of the title compound were isolated as a colourless foam.

$^1$H NMR (CDCl$_3$): =0.60 (3H), 1.12 (6H), 1.40-1.55 (2H), 1.73-1.88 (3H), 2.05 (1H), 2.21-2.64 (9H), 2.72 (1H), 3.00 (1H), 3.86 (1H), 3.89 (2H), 4.41 (1H), 4.46 (1H), 4.68 (1H), 5.77 (1H), 6.13 (1H), 6.42 (1H), 7.11 (2H), 7.23 (2H) ppm.

EXAMPLE 41

1-tert-butyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1-yl)benzyl]urea

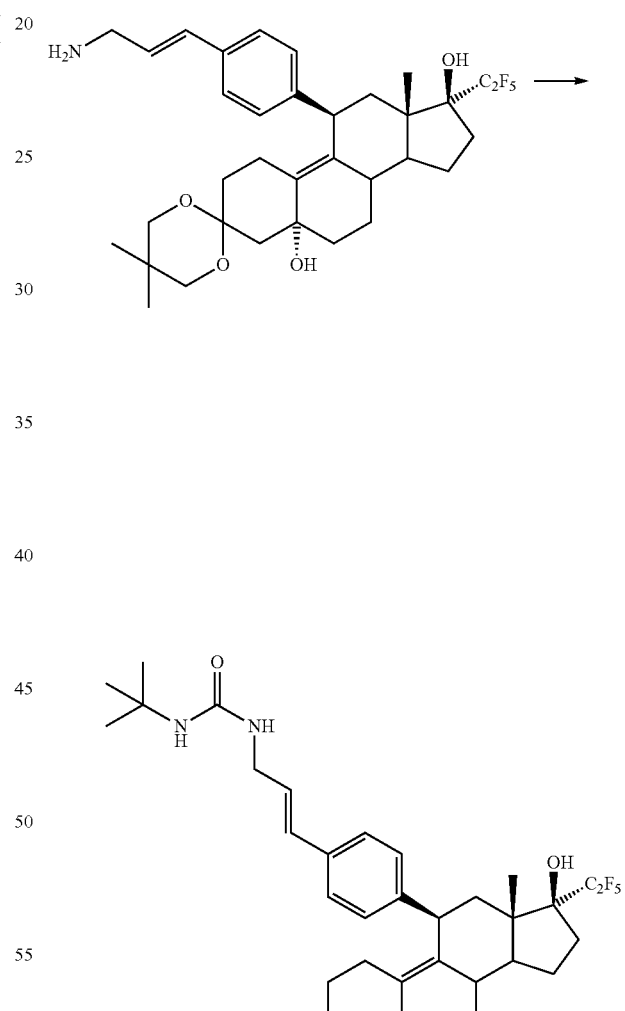

In analogy to Example 39, 40 mg (53 μmol) of the compound prepared according to Example 39a were converted using tert-butyl isocyanate and, after workup and purification, 16.3 mg (49%) of the title compound were isolated as a colourless foam.

$^1$H NMR (CDCl$_3$): =0.60 (3H), 1.32 (9H), 1.40-1.55 (2H), 1.73-1.87 (3H), 2.05 (1H), 2.21-2.63 (9H), 2.65 (1H), 2.73

(1H), 3.88 (2H), 4.41 (1H), 4.42 (1H), 4.47 (1H), 5.77 (1H), 6.15 (1H), 6.44 (1H), 7.10 (2H), 7.24 (2H) ppm.

EXAMPLE 42

1-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}-3-phenylurea

EXAMPLE 43

1-(4-cyanophenyl)-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea

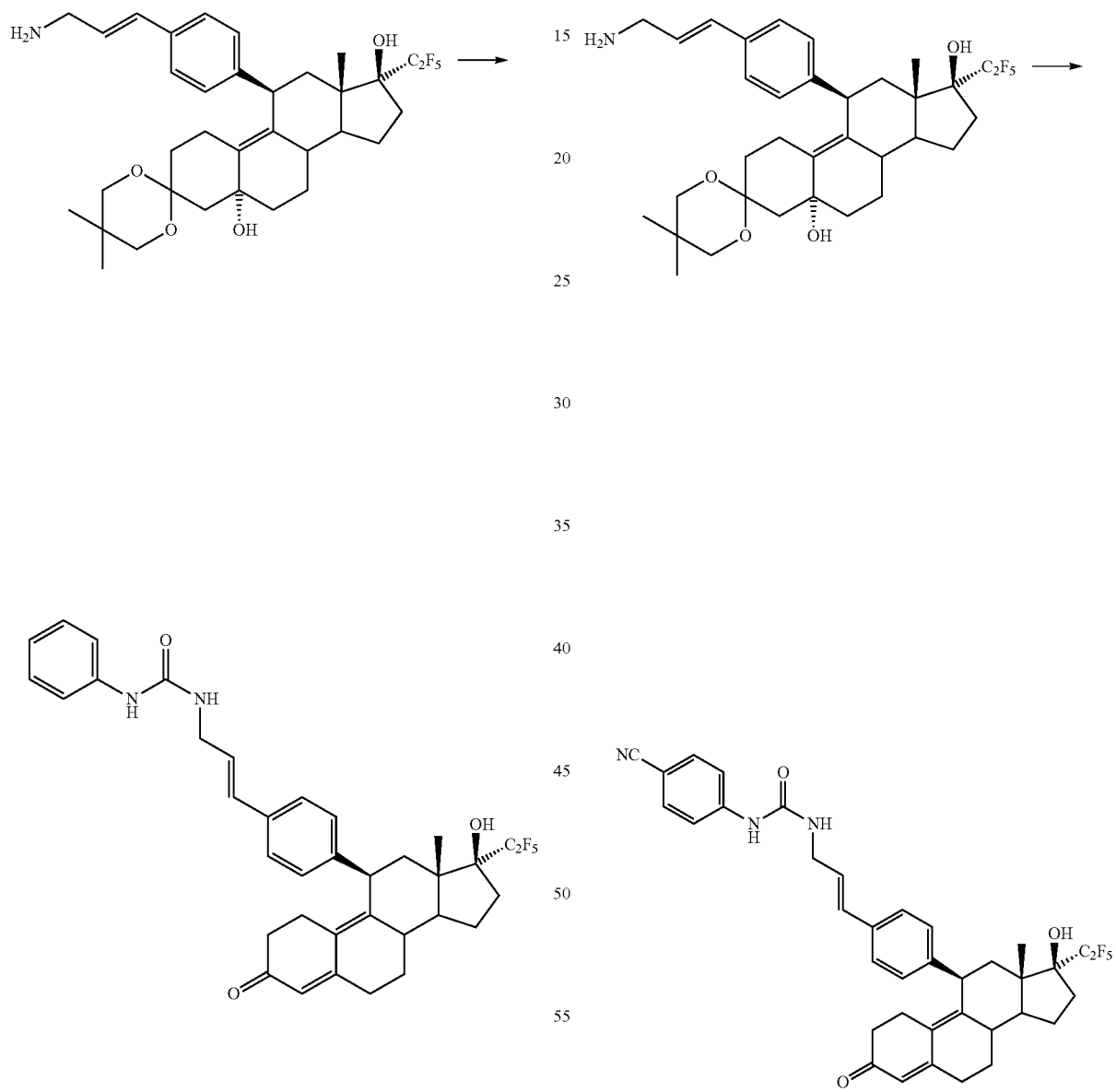

In analogy to Example 39, 40 mg (53 μmol) of the compound prepared according to Example 39a were converted using phenyl isocyanate and, after workup and purification, 10.2 mg (30%) of the title compound were isolated as a colourless foam.

$^1$H NMR (CDCl$_3$): =0.58 (3H), 1.38-1.53 (2H), 1.72-1.87 (3H), 2.04 (1H), 2.18-2.63 (9H), 2.70 (1H), 2.85 (1H), 3.93 (2H), 4.39 (1H), 5.48 (1H), 5.77 (1H), 6.11 (1H), 6.40 (1H), 6.99-7.11 (3H), 7.12-7.35 (7H) ppm.

In analogy to Example 39, 40 mg (53 μmol) of the compound prepared according to Example 39a were converted using 4-isocyanatobenzonitrile and, after workup and purification, 19 mg (54%) of the title compound were isolated as a colourless foam.

$^1$H NMR (CDCl$_3$): =0.63 (3H), 1.40-1.55 (2H), 1.73-1.87 (3H), 2.05 (1H), 2.19-2.65 (9H), 2.72 (1H), 2.96 (1H), 4.01

(2H), 4.41 (1H), 5.77 (1H), 5.90 (1H), 6.13 (1H), 6.45 (1H), 7.09 (2H), 7.17 (2H), 7.38 (2H), 7.46 (2H), 8.07 (1H) ppm.

EXAMPLE 44

1-(4-fluorophenyl)-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea

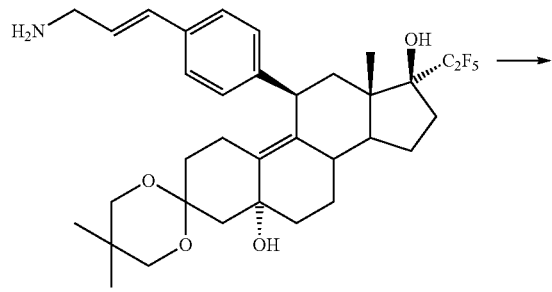

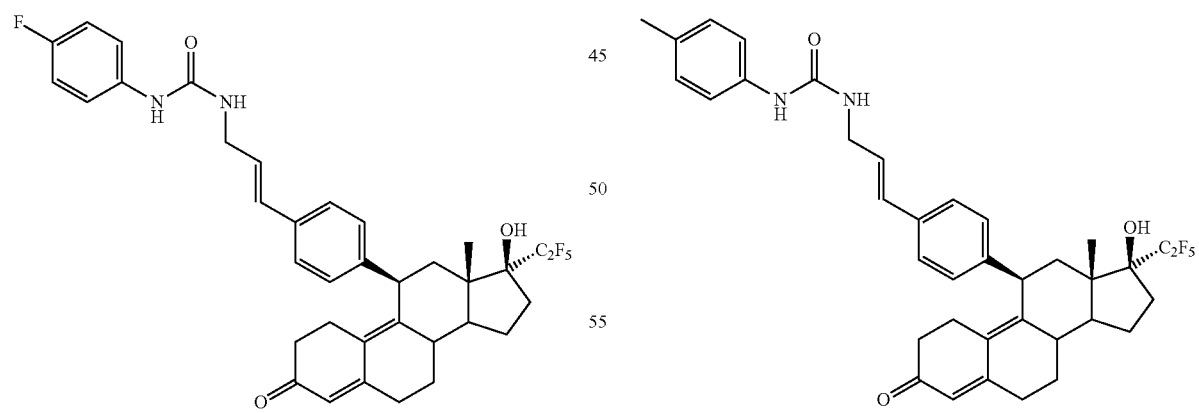

In analogy to Example 39, 40 mg (53 µmol) of the compound prepared according to Example 39a were converted using 4-fluorophenyl isocyanate and, after workup and purification, 21 mg (60%) of the title compound were isolated as a colourless foam.

$^1$H NMR (CDCl$_3$): =0.58 (3H), 1.38-1.54 (2H), 1.73-1.87 (3H), 2.04 (1H), 2.18-2.62 (9H), 2.70 (1H), 2.95 (1H), 3.92 (2H), 4.41 (1H), 5.77 (1H), 5.90 (1H), 6.13 (1H), 6.45 (1H), 7.09 (2H), 7.17 (2H), 7.38 (2H), 7.46 (2H), 8.07 (1H) ppm.

(2H), 4.39 (1H), 5.50 (1H), 5.76 (1H), 6.10 (1H), 6.39 (1H), 6.88 (2H), 7.06 (2H), 7.15-7.23 (4H), 7.26 (1H) ppm.

EXAMPLE 45

1-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}-3-p-tolylurea In analogy to Example 39, 40 mg (53 µmol) of the compound prepared according to Example 39a were converted using 4-tolyl isocyanate and, after workup and purification, 20.2 mg (58%) of the title compound were isolated as a colourless foam.

$^1$H NMR (CDCl$_3$): =0.58 (3H), 1.39-1.54 (2H), 1.73-1.87 (3H), 2.05 (1H), 2.18-2.63 (9H), 2.27 (3H), 2.71 (1H), 2.90

(1H), 3.93 (2H), 4.40 (1H), 5.32 (1H), 5.77 (1H), 6.11 (1H), 6.40 (1H), 6.89 (1H), 7.06 (2H), 7.08 (2H), 7.15 (2H), 7.20 (2H) ppm.

EXAMPLE 46

1-benzyl-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea

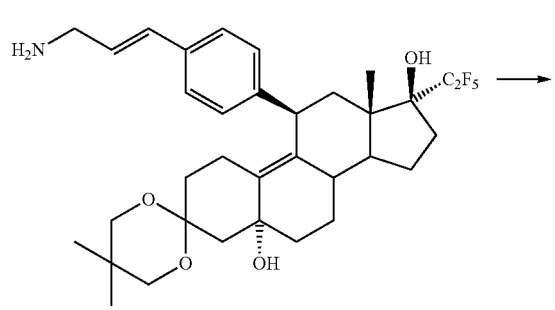

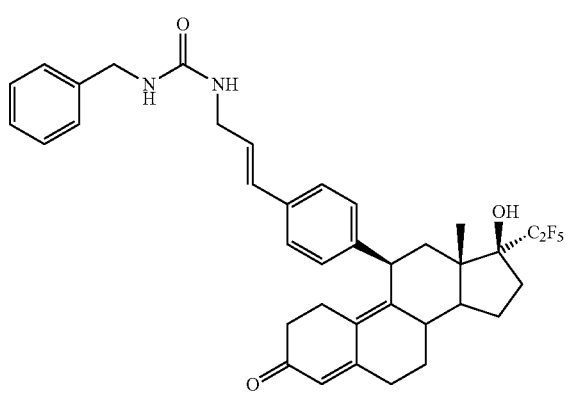

In analogy to Example 39, 40 mg (53 µmol) of the compound prepared according to Example 39a were converted using benzyl isocyanate and, after workup and purification, 18.2 mg (52%) of the title compound were isolated as a colourless foam.

$^1$H NMR (CDCl$_3$): =0.60 (3H), 1.38-1.54 (2H), 1.73-1.88 (3H), 2.05 (1H), 2.18-2.64 (9H), 2.70 (1H), 2.97 (1H), 3.87 (2H), 4.31 (2H), 4.40 (1H), 4.90 (1H), 5.11 (1H), 5.75 (1H), 6.10 (1H), 6.38 (1H), 7.09 (2H), 7.17-7.32 (7H) ppm.

EXAMPLE 47

1-tert-butyl-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea

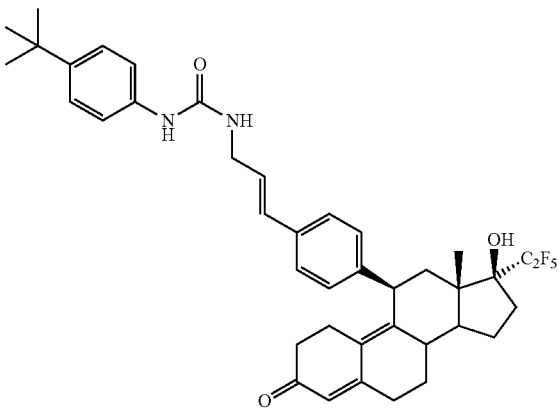

In analogy to Example 39, 40 mg (53 µmol) of the compound prepared according to Example 39a were converted using 4-tert-butylphenyl isocyanate and, after workup and purification, 18.6 mg (50%) of the title compound were isolated as a colourless foam.

$^1$H NMR (CDCl$_3$): =0.58 (3H), 1.27 (9H), 1.39-1.55 (2H), 1.72-1.89 (3H), 2.05 (1H), 2.19-2.65 (9H), 2.71 (1H), 2.80

(1H), 3.95 (2H), 4.40 (1H), 5.32 (1H), 5.77 (1H), 6.13 (1H), 6.41 (1H), 6.85 (1H), 7.08 (2H), 7.17-7.33 (6H) ppm.

EXAMPLE 48

1-(3,5-dimethyl isoxazol-4-yl)-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea

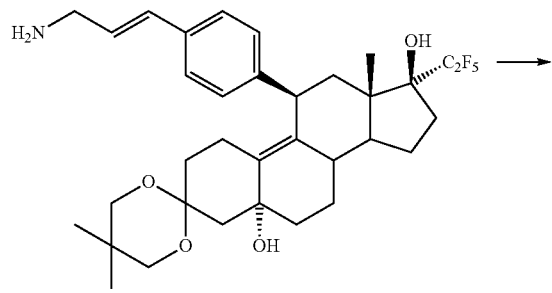

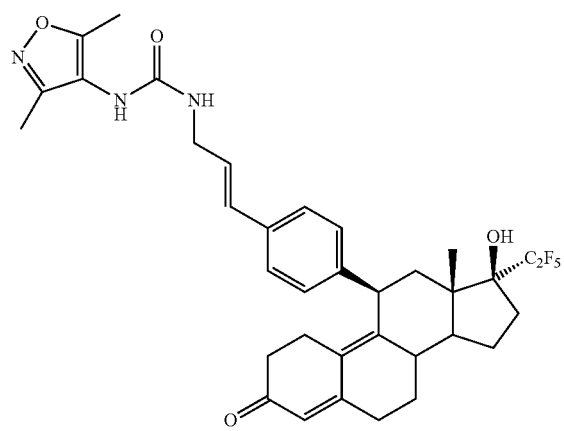

In analogy to Example 39, 40 mg (53 µmol) of the compound prepared according to Example 39a were converted using 3,5-dimethylisoxazol-4-yl isocyanate and, after workup and purification, 9.1 mg (26%) of the title compound were isolated as a colourless foam.

$^1$H NMR (CDCl$_3$): =0.59 (3H), 1.40-1.53 (2H), 1.74-1.86 (3H), 2.06 (1H), 2.18 (3H), 2.21-2.62 (9H), 2.33 (3H), 2.65

(1H), 2.72 (1H), 3.97 (2H), 4.42 (1H), 4.84 (1H), 5.77 (1H), 5.80 (1H), 6.11 (1H), 6.42 (1H), 7.11 (2H), 7.23 (2H) ppm.

EXAMPLE 49

(3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)propionic acid ethyl ester

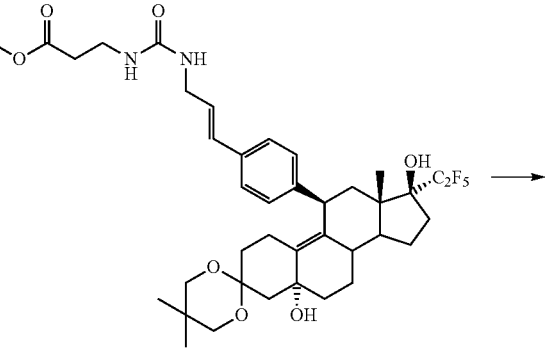

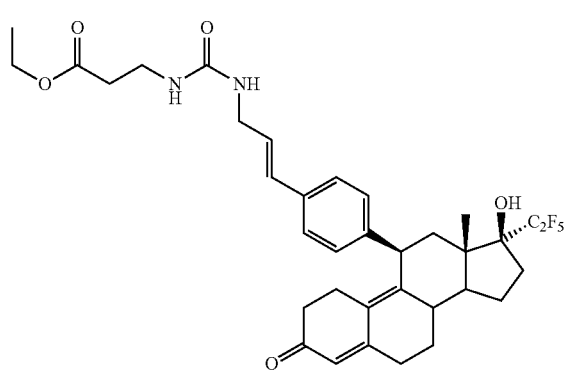

In analogy to Example 1, 40 mg of the crude product prepared according to Example 49a were converted and, after workup and purification, 16 mg (47%) of the title compound were isolated as a colourless foam.

$^1$H NMR (CDCl$_3$): =0.60 (3H), 1.23 (3H), 1.38-1.56 (2H), 1.72-1.87 (3H), 2.05 (1H), 2.19-2.64 (12H), 2.72 (1H), 3.44

(1H), 3.48 (1H), 3.91 (2H), 4.08 (1H), 4.13 (1H), 4.42 (1H), 4.64 (1H), 5.06 (1H), 5.78 (1H), 6.14 (1H), 6.45 (1H), 7.11 (2H), 7.25 (2H) ppm.

EXAMPLE 49a 3-(3-{(E)-3-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-1-yl)phenyl]allyl}ureido)propionic acid ethyl ester

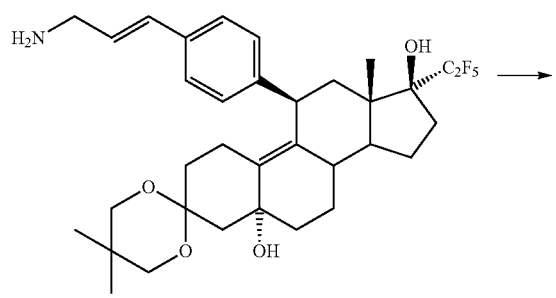

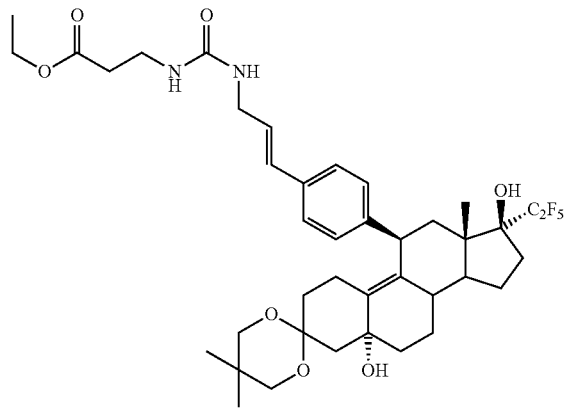

The solution of 100 mg (0.13 mmol) of the compound prepared according to Example 39a in 2.5 ml of dichloromethane was admixed with 21 μl of ethyl 3-isocyanatopropionate and stirred at 23° C. for 1 hour. The mixture was concentrated, and 104 mg of the title compound were isolated as a crude product, which was converted further without purification.

EXAMPLE 50

(3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)propionic acid

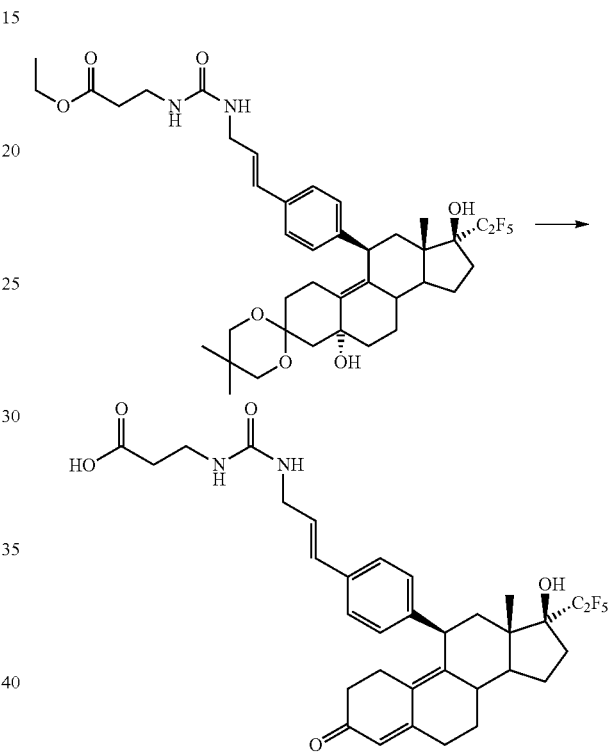

The solution of 64 mg (83 μmol) of the compound prepared according to Example 49a in 0.8 ml of tetrahydrofuran and 0.8 ml of ethanol was admixed with 0.8 ml of a 5% aqueous solution of lithium hydroxide and stirred at 23° C. for 4 hours. The mixture was diluted with water, acidified by adding 1 molar hydrochloric acid and extracted repeatedly with dichloromethane, and the combined organic extracts were washed with saturated sodium chloride solution and dried over sodium sulphate. The residue obtained after filtration and removal of solvent was dissolved in 1.2 ml of acetone, 90 μl of 4N hydrochloric acid were added and the mixture was stirred at 23° C. for 2 hours. The mixture was poured into a saturated sodium hydrogencarbonate solution and extracted repeatedly with dichloromethane, the combined organic extracts were dried over sodium sulphate and the residue obtained after filtration and removal of solvent was purified by chromatography. 16 mg (30%) of the title compound were isolated as a colourless foam.

$^1$H NMR (CD$_3$OD): =0.60 (3H), 1.35-1.55 (2H), 1.68-1.85 (3H), 2.09 (1H), 2.17-2.48 (7H), 2.54-2.72 (4H), 2.80 (1H), 3.35 (2H), 3.85 (2H), 4.50 (1H), 5.74 (1H), 6.19 (1H), 6.46 (1H), 7.17 (2H), 7.31 (2H) ppm.

EXAMPLE 51

3-(3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)acetic acid ethyl ester

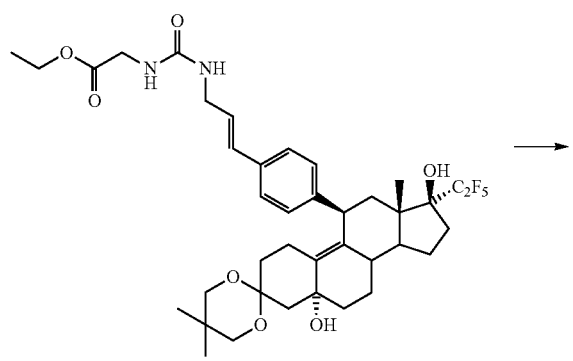

In analogy to Example 1, 40 mg of the crude product prepared according to Example 51a were converted and, after workup and purification, 12.4 mg (36%) of the title compound were isolated as a colourless foam.

$^1$H NMR (CDCl$_3$): =0.59 (3H), 1.25 (3H), 1.38-1.56 (2H), 1.72-1.87 (3H), 2.05 (1H), 2.19-2.64 (10H), 2.72 (1H), 3.93 (2H), 3.99 (2H), 4.18 (2H), 4.41 (1H), 4.90 (1H), 5.13 (1H), 5.77 (1H), 6.14 (1H), 6.46 (1H), 7.10 (2H), 7.25 (2H) ppm.

EXAMPLE 51a 3-(3-{(E)-3-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-1-yl)phenyl]allyl}ureido)acetic acid ethyl ester

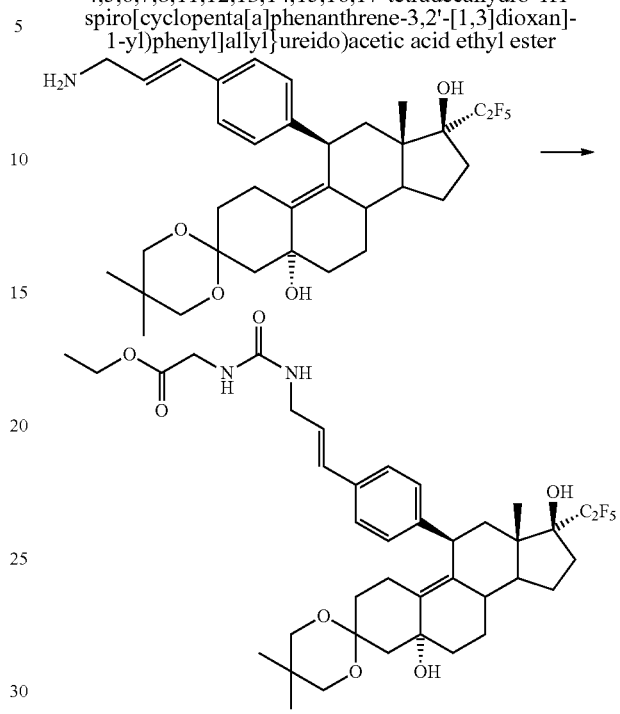

In analogy to Example 49a, 100 mg (0.13 mmol) of the compound prepared according to Example 39a were converted using ethyl isocyanatoacetate and, after workup, 101 mg of the title compound were isolated as a crude product.

EXAMPLE 52

3-(3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)acetic acid

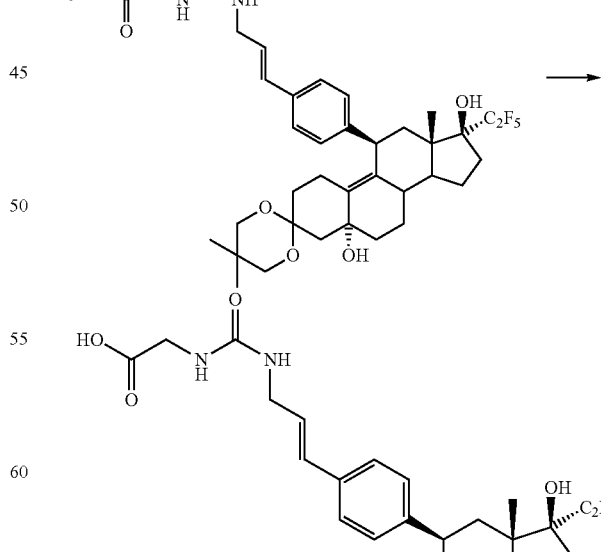

In analogy to Example 50, 60 mg (79 μmol) of the compound prepared according to Example 51a were converted and, after workup and purification, 21 mg (42%) of the title compound were isolated as a colourless foam.

$^{1}$H NMR (CD$_{3}$OD): =0.60 (3H), 1.36-1.57 (2H), 1.68-1.84 (3H), 2.09 (1H), 2.17-2.48 (5H), 2.54-2.72 (4H), 2.80 (1H), 3.71 (2H), 3.87 (2H), 4.50 (1H), 5.74 (1H), 6.21 (1H), 6.49 (1H), 7.17 (2H), 7.31 (2H) ppm.

EXAMPLE 53

1-(4-chlorophenyl)-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea

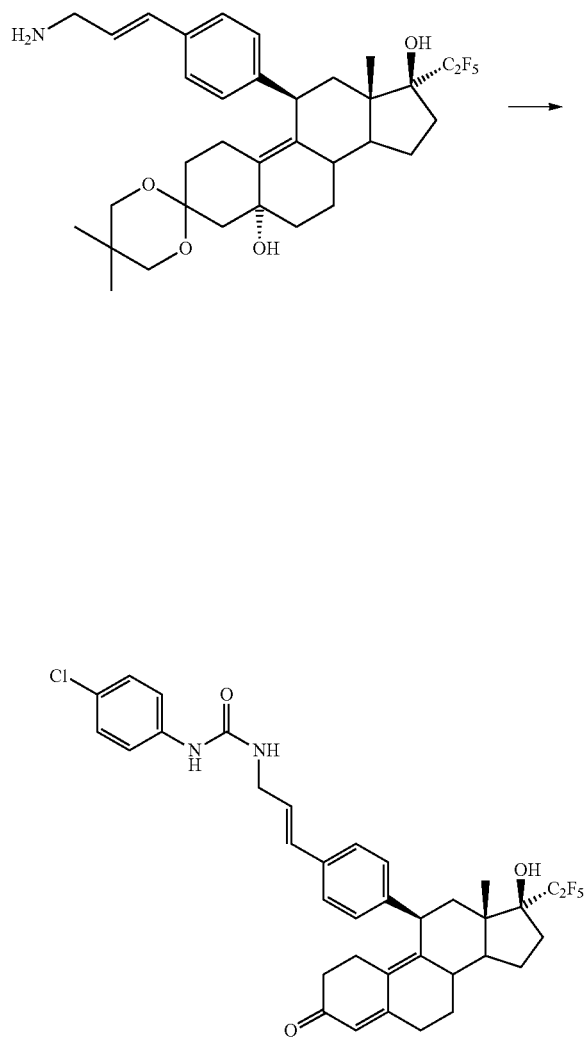

In analogy to Example 39, 40 mg (53 μmol) of the compound prepared according to Example 39a were converted using 4-chlorophenyl isocyanate and, after workup and purification, 23.5 mg (66%) of the title compound were isolated as a colourless foam.

$^{1}$H NMR (CDCl$_{3}$): =0.58 (3H), 1.36-1.56 (2H), 1.70-1.90 (3H), 2.04 (1H), 2.15-2.63 (9H), 2.70 (1H), 3.00 (1H), 3.91 (2H), 4.39 (1H), 5.70 (1H), 5.76 (1H), 6.07 (1H), 6.38 (1H), 7.01-7.25 (8H), 7.53 (1H) ppm.

EXAMPLE 54

1-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}-3-(4-methoxyphenyl)urea

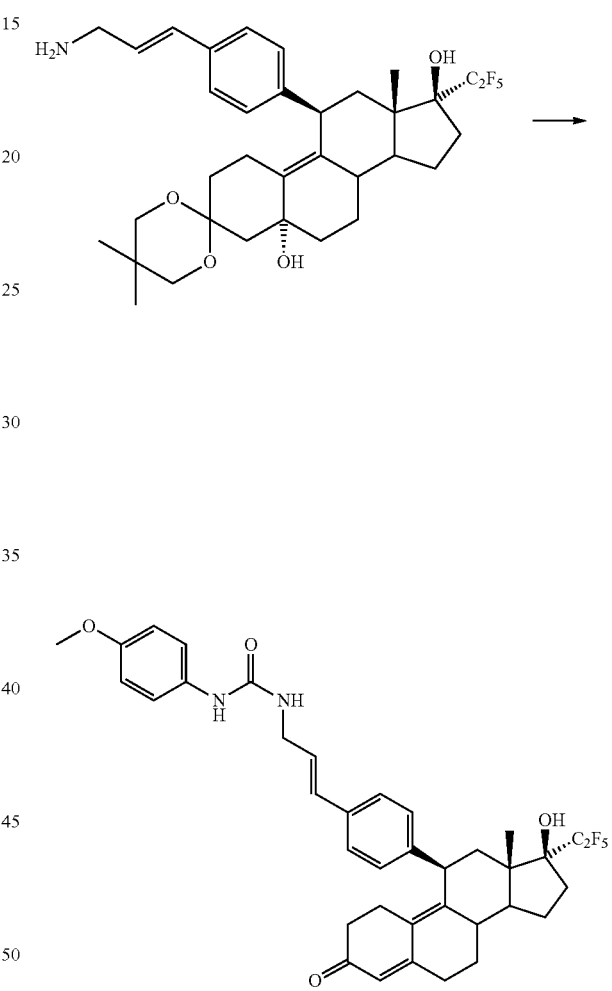

In analogy to Example 39, 40 mg (53 μmol) of the compound prepared according to Example 39a were converted using 4-methoxyphenyl isocyanate and, after workup and purification, 22.2 mg (62%) of the title compound were isolated as a colourless foam.

$^{1}$H NMR (CDCl$_{3}$): =0.58 (3H), 1.37-1.55 (2H), 1.72-1.88 (3H), 2.04 (1H), 2.17-2.63 (9H), 2.71 (1H), 2.95 (1H), 3.75 (3H), 3.93 (2H), 4.39 (1H), 5.22 (1H), 5.76 (1H), 6.11 (1H), 6.40 (1H), 6.75-6.84 (3H), 7.07 (2H), 7.16 (2H), 7.20 (2H) ppm.

EXAMPLE 55
4-(3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)benzoic acid ethyl ester
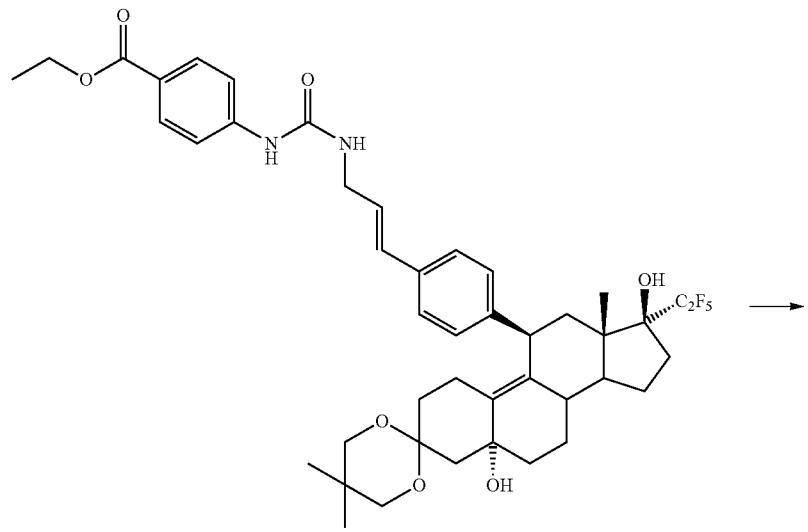
5
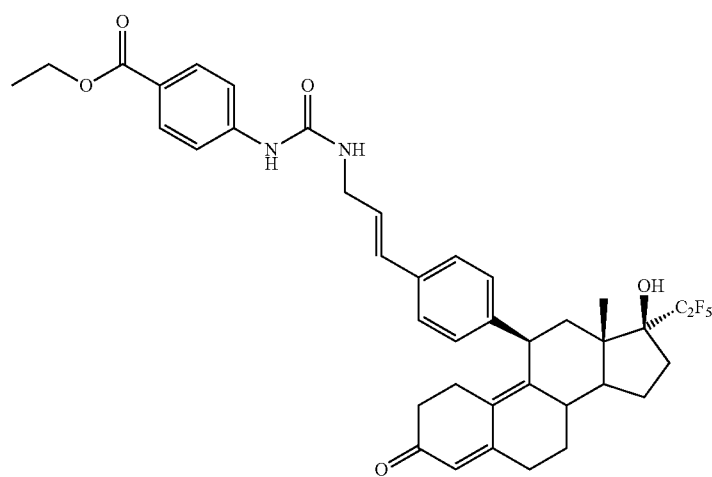

In analogy to Example 1, 41 mg of the crude product prepared according to Example 55a were converted and, after workup and purification, 18.7 mg (50%) of the title compound were isolated as a colourless foam.

$^1$H NMR (CDCl$_3$): =0.61 (3H), 1.35 (3H), 1.39-1.54 (2H), 1.71-1.88 (3H), 2.04 (1H), 2.16-2.64 (9H), 2.70 (1H), 3.55 (1H), 3.98 (2H), 4.30 (2H), 4.38 (1H), 5.77 (1H), 6.11 (1H), 6.15 (1H), 6.43 (1H), 7.04 (2H), 7.11 (2H), 7.39 (2H), 7.82 (2H), 8.09 (1H) ppm.

EXAMPLE 55a

4-[3-(3-{(E)-3-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxan]-1-yl)phenyl]allyl}ureido)]benzoic acid ethyl ester

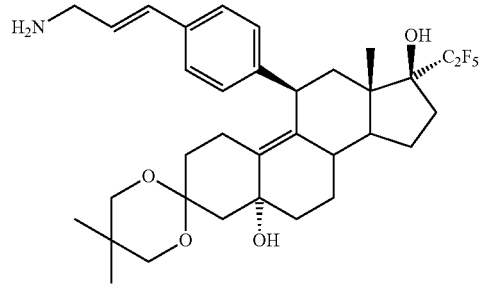

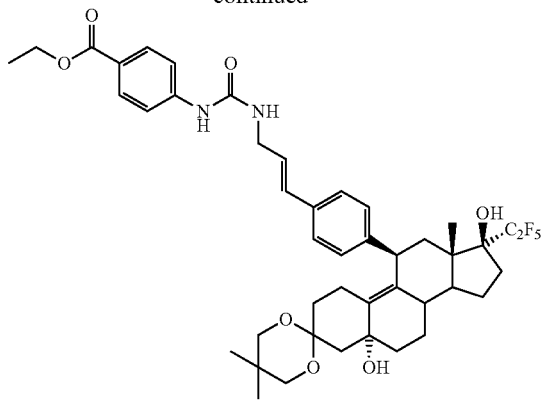

In analogy to Example 49a, 120 mg (0.16 mmol) of the compound prepared according to Example 39a were converted using ethyl 4-isocyanatobenzoate and, after workup, 121 mg of the title compound were isolated as a crude product.

EXAMPLE 56

4-(3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)benzoic acid

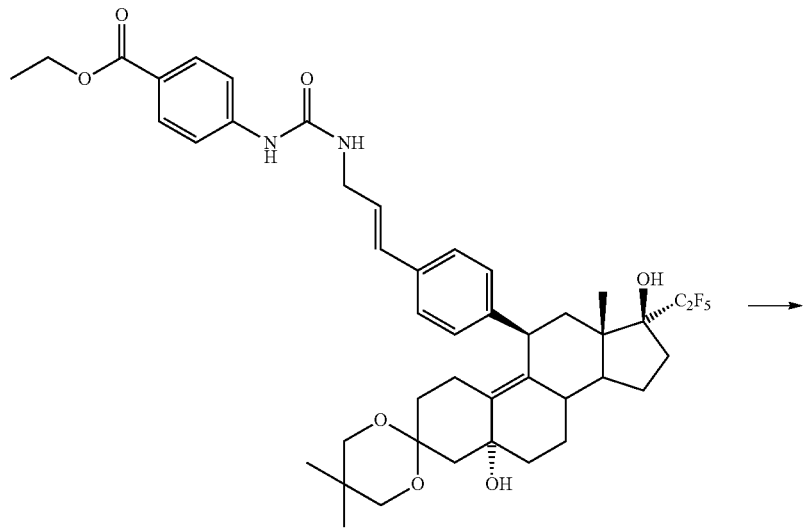

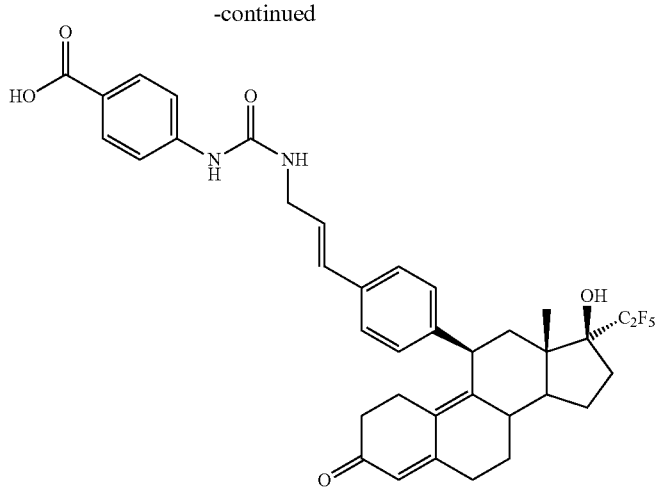

In analogy to Example 50, 80 mg of the compound prepared according to Example 55a were converted and, after workup and purification, 35 mg (52%) of the title compound were isolated as a colourless foam.

$^1$H NMR (CD$_3$OD): =0.58 (3H), 1.35-1.54 (2H), 1.69-1.82 (3H), 2.08 (1H), 2.17-2.46 (5H), 2.55-2.71 (4H), 2.80 (1H), 3.95 (2H), 4.49 (1H), 5.73 (1H), 6.24 (1H), 6.52 (1H), 7.17 (2H), 7.32 (2H), 7.42 (2H), 7.87 (2H) ppm.

EXAMPLE 57

1-allyl-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea In analogy to Example 39, 20 mg (27 μmol) of the compound prepared according to Example 39a were converted using allyl isocyanate and, after workup and purification, 10 mg (62%) of the title compound were isolated as a colourless foam.

$^1$H NMR (CD$_3$OD): =0.60 (3H), 1.40-1.55 (2H), 1.74-1.87 (3H), 2.06 (1H), 2.21-2.64 (10H), 2.73 (1H), 3.80 (2H), 3.94 (2H), 4.42 (1H), 4.61 (1H), 4.66 (1H), 5.11 (1H), 5.19 (1H), 5.78 (1H), 5.84 (1H), 6.16 (1H), 6.46 (1H), 7.11 (2H), 7.25 (2H) ppm.

EXAMPLE 58

1-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}-3-(4-piperidin-1-ylphenyl)urea

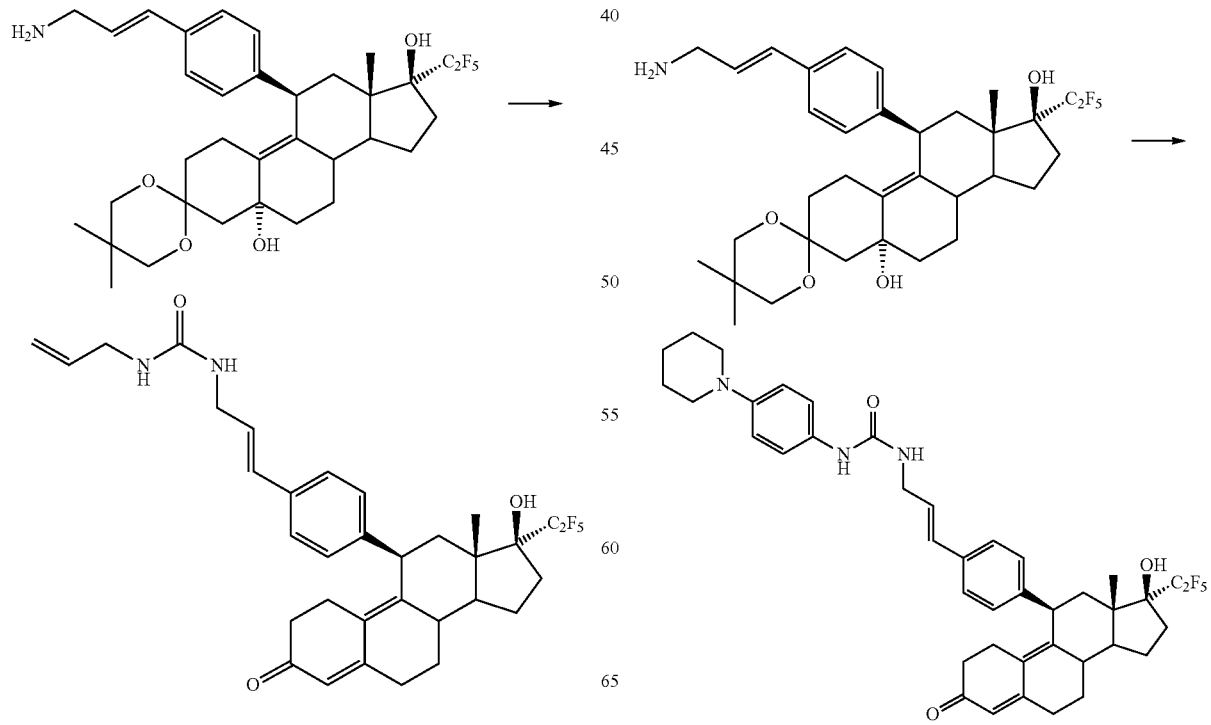

In analogy to Example 39, 40 mg (53 µmol) of the compound prepared according to Example 39a were converted using 4-piperidinephenyl isocyanate and, after workup and purification, 17 mg (43%) of the title compound were isolated as a colourless foam.

$^1$H NMR (CD$_3$OD): =0.58 (3H), 1.39-1.61 (4H), 1.63-1.87 (7H), 2.05 (1H), 2.20-2.63 (9H), 2.71 (1H), 2.73 (1H), 3.11 (4H), 3.95 (2H), 4.40 (1H), 4.95 (1H), 5.77 (1H), 6.13 (1H), 6.37 (1H), 6.41 (1H), 6.87 (2H), 7.09 (2H), 7.12 (2H), 7.23 (2H) ppm.

EXAMPLE 59

Determination of Progesterone Receptor-Antagonistic Action in Stable Transfectants of Human Neuroblastoma Cells (SK-N-MC Cells) with the Human Progesterone A or Progesterone B Receptor and an MN-LUC Reporter Construct SK-N-MC cells (human neuroblastoma cells) which have been stably transfected with plasmids expressing the human progesterone receptor B (pRChPR-B-neo) or the human progesterone receptor A (pRChPR-A-neo) and a reporter construct (pMMTV-LUC) were incubated for 24 hours either in the absence (negative control) or in the presence of ascending amounts of the particular test compound (0.01 nmol/l, 0.1 nmol/l, 1 nmol/l, 10 nmol/l, 100 nmol/l and 1 pmol/l), in order to determine the agonistic efficacy. As a positive control of the reporter gene induction, the cells were treated with the synthetic gestagen promegestone (0.01 nmol/l, 0.1 nmol/l, 1 nmol/l, 10 nmol/l, 100 nmol/l and 1 pmol/l). To determine the antagonistic activity, the cells were treated with 0.1 nmol/l promegestone and additionally with ascending amounts of the particular test compound (0.01 nmol/l, 0.1 nmol/l, 1 nmol/l, 10 nmol/l, 100 nmol/l and 1 pmol/l). The activity of the reporter gene LUC (LUC=luciferase) was determined in the cell lysates and measured as RLU (relative light units). All measurements are reported as % efficacy and as EC$_{50}$ and IC$_{50}$ concentrations.

a) Agonistic Activity:

None of the compounds mentioned exhibits agonistic activity.

b) Antagonistic Activity:

All compounds mentioned exhibit 100% antagonistic activity.

The antagonistic potency of the compounds is summarized in Table 1. Preference is given in accordance with the invention to compounds whose PR-A or PR-B value is ≤0.2 nM.

TABLE 1

| Ex. | PR-A IC$_{50}$ [nM] | PR-B IC$_{50}$ [nM] |
|---|---|---|
| 1 | 0.011 | 0.012 |
| 2 | 0.14 | 0.25 |
| 3 | 1.5 | 1.8 |
| 4 | 1.0 | 1.1 |
| 5 | 0.4 | 0.13 |
| 6 | 0.16 | 0.12 |
| 7 | 0.012 | 0.011 |
| 8 | 0.012 | 0.077 |
| 9 | 0.055 | 0.09 |
| 10 | 0.2 | 0.86 |
| 11 | 0.011 | 0.012 |
| 12 | 0.13 | 0.26 |
| 13 | 0.1 | 0.3 |
| 14 | 0.011 | 0.011 |
| 15 | 0.011 | <0.01 |
| 16 | 0.1 | 0.3 |
| 17 | 0.1 | 0.7 |
| 18 | 0.01 | 0.02 |
| 19 | 3 | 3 |
| 20 | 9 | 11 |
| 21 | 0.9 | 1 |
| 22 | 0.3 | 1 |
| 23 | 0.2 | 0.2 |
| 24 | 1 | 1 |
| 25 | 1 | 2 |
| 26 | 0.9 | 1 |
| 27 | 0.2 | 0.1 |
| 28 | 0.06 | 0.1 |
| 29 | 0.08 | 0.09 |
| 30 | 0.09 | 0.08 |
| 31 | 0.09 | 0.1 |
| 32 | 0.01 | 0.01 |
| 33 | 0.1 | 0.8 |
| 34 | 3.9 | 2.8 |
| 35 | 0.1 | 0.09 |
| 36 | 0.08 | 0.08 |
| 37 | 0.4 | 0.5 |
| 38 | 0.09 | 0.1 |
| 39 | 0.09 | 0.1 |
| 40 | 0.1 | 0.1 |
| 41 | 0.1 | 0.1 |
| 42 | 0.1 | nn |
| 43 | nn | nn |
| 44 | 0.1 | 0.1 |
| 45 | 0.1 | 0.1 |
| 46 | 0.07 | 0.09 |
| 47 | 0.8 | 0.3 |
| 48 | 0.09 | 0.03 |
| 49 | 0.1 | 0.3 |
| 50 | 8 | 3 |
| 51 | 0.1 | 0.1 |
| 52 | 3 | 2 |
| 53 | 0.1 | 0.2 |
| 54 | 0.1 | nn |
| 55 | 0.1 | 0.09 |
| 56 | 0.9 | 1.9 |
| 57 | 0.09 | 0.1 |
| 58 | 0.5 | nn |
| Ref. 1* | 0.7 | 0.8 | nn = not measured

*Ref. 1 Table 1: The comparative compound (reference substance) is the compound, described in Example 10 of WO 1998/34947, (8S,11R,13S,14S,17S)-17-hydroxy-11-[4-(hydroxymethyl)phenyl]-13-methyl-17-pentafluoroethyl-1,2,6,7,8,11,12,13,14,15,16,17-dodecahydrocyclopenta[a]phenanthren-3-one.

EXAMPLE 60

Determination of Metabolic Stability in Human and Rat Liver Microsomes

Isolated human liver microsomes (HLM) were used to assess the metabolic stability of compounds of general formula I.

The incubations were conducted with 2.4 ml of HLM solution (protein content 0.5 mg/ml), 30 µl of the test compound (final concentration 1 µM) and 0.6 ml of the cofactor mixture (=NADPH-generating system composed of 3 IU glucose-6-phosphate dehydrogenase, 14.6 mg glucose-6-phosphate, 1.2 mg NADP) at 37° C. in 100 mM phosphate buffer at pH 7.4. Samples were taken at 6 time points (2-60 min) and precipitated with an equal volume of methanol, and the recovery of the test substances used in the supernatant was determined by LC-MS/MS analysis. The half-life of substance degradation determined therefrom was used to calculate what is called the intrinsic clearance of the substance in the liver microsome preparation. With the aid of this, together with various physiological parameters (human hepatic blood flow: 1.3 l*kg/h;

specific liver weight (per kg of body weight): 21 g/kg; microsomal protein content: 40 mg/g of liver), in accordance with the well-stirred model, (metabolic) in vivo clearance in relation to phase I reactions was predicted. In addition, under the assumptions that (i) absorption of the test substance is 100%, and (ii) the first pass is completely reflected by liver microsome metabolism, a maximum oral bioavailability (Fmax) was calculated.

The compounds tested have surprisingly high metabolic stability (small based on the clearance rate predicted on the basis of the in vitro data) and good predicted maximum oral bioavailability $F_{max}$ (Table 2).

In addition, some compounds have an unusually good solubility, for this active ingredient class, in aqueous medium under physiological conditions (Table 2).

TABLE 2

| Ex. | Predicted clearance [l/h/kg] Human | Rat | Predicted $F_{max}$ [%] (maximum oral bioavailability) Human | Rat | Solubility at pH 7.4 [mg/l] |
|---|---|---|---|---|---|
| Ref. 1* | 0.7 | 0.8 | 42 | 80 | 17 |
| 1 | 0.90 | 1.9 | 31 | 54 | 6 |
| 2 | 0.41 | 1.3 | 69 | 69 | 11 |
| 5 | 0.00 | 0.5 | 100 | 88 | 203 |
| 6 | 0.21 | 0.7 | 84 | 83 | 9 |
| 7 | 0.38 | 0.9 | 71 | 79 | 6 |
| 8 | 0.18 | 0.3 | 87 | 92 | 7 |
| 9 | 0.43 | 1.0 | 68 | 76 | 8 |
| 10 | 0.36 | 1.0 | 73 | 76 | 8 |
| 13 | 0.63 | 0.1 | 52 | 97 | >179 |
| 14 | 0.9 | 1.1 | 31 | 75 | 9 |
| 16 | 1.02 | 2.0 | 23 | 52 | 10 |
| 17 | 0.89 | 0.4 | 33 | 91 | >188 |
| 18 | 0.84 | 1.8 | 36 | 57 | 6 |
| 21 | 0.7 | 0.5 | 48 | 88 | 7 |
| 22 | 0.8 | 1.0 | 41 | 77 | 6 |
| 23 | 0.4 | 0.2 | 67 | 95 | 8 |
| 27 | 0.98 | 0.9 | 26 | 79 | 10 |
| 28 | 0.35 | 0.1 | 74 | 97 | 120 |
| 29 | 0.08 | 0.0 | 94 | 100 | 102 |
| 36 | 0.36 | 0.8 | 72 | 82 | 5 |

*Ref. 1 Table 2: The comparative compound (reference substance) is the compound, described in Example 10 of WO 1998/34947, (8S,11R,13S,14S,17S)-17-hydroxy-11-[4-(hydroxymethyl)phenyl]-13-methyl-17-pentafluoroethyl-1,2,6,7,8,11,12,13,14,15,16,17-dodecahydrocyclopenta[a]phenanthren-3-one.

This compound has good predicted maximum bioavailability in rats, but not in humans.

Particular preference is therefore given to those compounds which have a predicted maximum oral bioavailability greater than 50% in different species (rats, humans).

Very particular preference is given to those compounds which have a predicted maximum oral bioavailability greater than 70% in different species (rats, humans). Examples include compounds of Examples 5, 6, 7, 8, 10, 28, 29 and 36.

Particular preference is likewise given to compounds with improved solubility. Examples include compounds of Examples 5, 13, 17, 28 and 29.

EXAMPLE 61

Abortion Test on Female Rats

The action of progesterone and of the progesterone receptor is a fundamental precondition for successful pregnancy or gestation in mammals. The progesterone-antagonistic action of the inventive compounds was tested on pregnant rats (6 rats per group) on days 5 to 7 post coitum under conventional housing and feeding conditions.

After successful mating, the pregnant animals (presence of sperm in the vaginal smear on day 1 of pregnancy=d1 p.c.) were randomized and divided into the treatment group and the control group. The animals then each received subcutaneously or orally 0.15; 0.5; 1.5 or 5 mg/kg of the test compound or 1.0 ml/kg of vehicle (benzyl benzoate/castor oil: 1+4 [v/v]) daily from day 5 to day 7 (d5-d7 p.c.).

Autopsy was conducted on day 9 (d9 p.c.). As a characteristic of progesterone receptor-antagonistic action, the uterus was examined for the presence of nidation sites. Complete absence, or else the presence of pathological, haemorrhagic or otherwise abnormal nidation sites, on day 9 (d9 p.c.) was considered as abortion. The results of the tests are shown in Table 3.

TABLE 3

| Test compound | Daily dose [mg/kg] p.o. | Abortion rate [%] |
|---|---|---|
| Vehicle | | 0 |
| Example 17 | 0.5 | 0 |
| | 1.5 | 16.7 |
| | 5.0 | 100.0 |
| Example 29 | 0.5 | 0 |
| | 1.5 | 16.7 |
| | 5.0 | 100.0 |

The invention claimed is:

1. 17-Hydroxy-17-pentafluoroethylestra-4,9(10)-diene 11-benzylidene derivatives of the general formula (I)

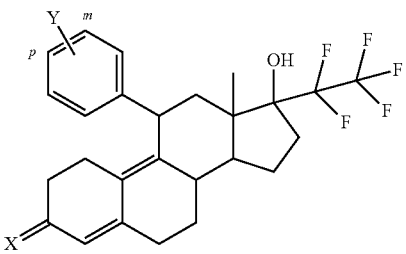

(I)

in which

Y is a —$CR^1$=$CHR^2$ or a —$CR^1$=$NR^3$ group, each of which is joined to the phenyl ring in the meta (m) or para (p) position, in which $R^1$ is hydrogen or a $C_1$-$C_{10}$-alkyl radical, $R^2$ is hydrogen, a $C_1$-$C_{10}$-alkyl, $C_2$-$C_{10}$-alkenyl, aryl, $C_7$-$C_{20}$-aralkyl, $C_1$-$C_{10}$-acyl, $CO_2R^4$, CN, CH=CH—$CO_2R^4$, $CH_2CH(CO_2R^4)_2$, $CH_2CH(CN)_2$ or a $CH_2NHCONHR^5$ radical and $R^3$ is a $C_1$-$C_{10}$-alkyl, O—$(CH_2)_n$—$COOR^4$, O—$CH_2$-aryl, aryl, $C_7$-$C_{20}$-aralkyl or a $CH_2CO_2R^4$ radical in which $R^4$ is hydrogen, or a $C_1$-$C_{10}$-alkyl group and $R^5$ is a $C_1$-$C_{10}$-alkyl, $C_2$-$C_{10}$-alkenyl, aryl, $C_7$-$C_{20}$-aralkyl, $(CH_2)_nCO_2R^4$ group where n=1 or 2 and $R^4$ is defined as specified, or $R^5$ is a

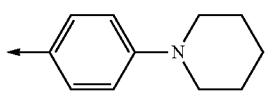

group and

X is oxygen, an NOR$^6$ or an NNHSO$_2$R$^6$ group, in which

R$^6$ is hydrogen, a C$_1$-C$_{10}$-alkyl, aryl or C$_7$-C$_{20}$-aralkyl radical, or a salts, or α-, β- or γ-cyclodextrin clathrate thereof.

2. Compound according to claim 1 in which X is oxygen.

3. Compound according to claim 1 in which the Y group is bonded to the phenyl ring in the para position.

4. Compound according to claim 1, in which Y is a —CR$^1$═CHR$^2$ group where R$^1$ is defined as hydrogen and R$^2$ is defined as in claim 1.

5. (8S,11R,13S,14S,17S)-17-hydroxy-13-methyl-17-pentafluoroethyl-11-(4-vinylphenyl)-1,2,6,7,8,11,12,13,14,15, 16, 17-dodecahydrocyclopenta[a]phenanthren-3-one;

(8S,11R,13S,14S,17S)-17-hydroxy-11-[4-((E)-3-hydroxypropenyl)phenyl]-13-methyl-17-pentafluoroethyl-1,2, 6,7,8,11,12, 13,14,15,16,17-dodecahydrocyclopenta[a] phenanthren-3-one;

2-{(E)-3[4-(8S,11R,13S,14S,17S)-17-hydroxy-13-methyl-3-oxo-17-pentafluoroethyl-2,3,6,7,8,11,12,13,14, 15,16,17-dodecahydro-1H-cyclopenta[a]phenanthren-11-yl)phenyl]allyl}malonic acid;

(8S,11R,13S,14S,17S)-17-hydroxy-13-methyl-17-pentafluoroethyl-11-[4-((E)-2-pyridin-2-ylvinyl)phenyl]-1,2,6,7,8,11,12,13,14,15,16,17-dodecahydrocyclopenta[a]phenanthren-3-one;

(8S,11R,13S,14S,17S)-17-hydroxy-13-methyl-17-pentafluoroethyl-11-[4-((E)-2-pyridin-3-ylvinyl)phenyl]-1,2,6,7,8,11,12,13,14,15,16,17-dodecahydrocyclopenta[a]phenanthren-3-one;

(8S,11R,13S,14S,17S)-17-hydroxy-13-methyl-17-pentafluoroethyl-11-[4-((E)-2-pyridin-4-ylvinyl)phenyl]-1,2,6,7,8,11,12,13,14,15,16,17-dodecahydrocyclopenta[a]phenanthren-3-one;

(8S,11R,13S,14S,17S)-17-hydroxy-13-methyl-11-{4-[(E)-2-(2-methylthiazol-4-yl)vinyl]phenyl}-17-pentafluoroethyl-1,2,6,7,8,11,12,13,14,15,16,17-dodecahydrocyclopenta[a]phenanthren-3-one;

(8S,11R,13S,14S,17S)-17-hydroxy-13-methyl-11-{4-[(E)-2-(2-methylbenzothiazol-5-yl)vinyl]phenyl}-17-pentafluoroethyl-1,2,6,7,8,11,12,13,14,15,16,17-dodecahydrocyclopenta[a]phenanthren-3-one;

(8S,11R,13S,14S,17S)-17-hydroxy-11-(4-isopropenylphenyl)-13-methyl-17-pentafluoroethyl-1,2,6,7,8, 11,12,13,14,15,16,17-dodecahydrocyclopenta[a] phenanthren-3-one;

(E)-3-[4-((8S,11R,13S,14S,17S)-17-hydroxy-13-methyl-3-oxo-17-pentafluoroethyl-2,3,6,7,8,11,12,13,14,15, 16,17-dodecahydro-1H-cyclopenta[a]phenanthren-11-yl)phenyl]acrylic acid ethyl ester;

(E)-3-[4-((8S,11R,13S,14S,17S)-17-hydroxy-13-methyl-3-oxo-17-pentafluoroethyl-2,3,6,7,8,11,12,13,14,15, 16,17-dodecahydro-1H-cyclopenta[a]phenanthren-11-yl)phenyl]acrylic acid;

(E)-3-[4-((8S,11R,13S,14S,17S)-17-hydroxy-13-methyl-3-oxo-17-pentafluoroethyl-2,3,6,7,8,11,12,13,14,15, 16,17-dodecahydro-1H-cyclopenta[a]phenanthren-11-yl)phenyl]acrylonitrile;

(2E,4E)-5-[4-((8S,11R,13S,14S,17S)-17-hydroxy-13-methyl-3-oxo-17-pentafluoroethyl-2,3,6,7,8,11,12,13, 14,15,16,17-dodecahydro-1H-cyclopenta[a]phenanthren-11-yl)phenyl]penta-2,4-dienoic acid ethyl ester;

(8S,11R,13S,14S,17S)-17-hydroxy-13-methyl-11-{4-[(E)-3-oxobut-1-enyl)phenyl]-17-pentafluoroethyl-1,2, 6,7,8,11,12,13,14,15, 16,17-dodecahydrocyclopenta[a] phenanthren-3-one;

(2E,4E)-5-[4-((8S,11R,13S,14S,17S)-17-hydroxy-13-methyl-3-oxo-17-pentafluoroethyl-2,3,6,7,8,11,12,13, 14,15,16,17-dodecahydro-1H-cyclopenta[a]phenanthren-11-yl)phenyl]penta-2,4-dienoic acid;

(8S,11R,13S,14S,17S)-11-[((E/Z)-4-buta-1,3-dienyl)phenyl]-17-hydroxy-13-methyl-17-pentafluoroethyl-1,2,6, 7,8,11,12,13,14,15, 16,17-dodecahydrocyclopenta[a] phenanthren-3-one;

(8S,11R,13S,14S,17S)-17-hydroxy-13-methyl-17-pentafluoroethyl-11-[3-((E)-2-pyridin-4-ylvinyl)phenyl]-1,2,6,7,8,11,12,13,14,15,16,17-dodecahydrocyclopenta[a]phenanthren-3-one;

2-{(E)-3-[4-((8S,11R,13S,14S,17S)-17-hydroxy-13-methyl-3-oxo-17-pentafluoroethyl-2,3,6,7,8,11,12,13,14, 15,16,17-dodecahydro-1H-cyclopenta[a]phenanthren-11-yl)phenyl]allyl}malonitrile;

3-{(E)-2-[44-((8S,11R,13S,14S,17S)-17-hydroxy-13-methyl-3-oxo-17-pentafluoroethyl-2,3,6,7,8,11,12,13, 14,15,16,17-dodecahydro-1H-cyclopenta[a]phenanthren-11-yl)phenyl]vinyl}benzoic acid;

4-{(E)-2-[4-((8S,11R,13S,14S,17S)-17-hydroxy-13-methyl-3-oxo-17-pentafluoroethyl-2,3,6,7,8,11,12,13,14, 15,16,17-dodecahydro-1H-cyclopenta[a]phenanthren-11-yl)phenyl]vinyl}benzoic acid;

3-{(E)-2-[4-((8S,11R,13S,14S,17S)-17-hydroxy-13-methyl-3-oxo-17-pentafluoroethyl-2,3,6,7,8,11,12,13,14, 15,16,17-dodecahydro-1H-cyclopenta[a]phenanthren-11-yl)phenyl]vinyl}benzoic acid methyl ester;

4-{(E)-2-[4-((8S,11R,13S,14S,17S)-17-hydroxy-13-methyl-3-oxo-17-pentafluoroethyl-2,3,6,7,8,11,12,13,14, 15,16,17-dodecahydro-1H-cyclopenta[a]phenanthren-11-yl)phenyl]vinyl}benzoic acid methyl ester;

(8S,11R,13S,14S,17S)-17-hydroxy-11-{4-[(E)-2-(4-methanesulphonylphenyl)vinyl]phenyl}-13-methyl-17-pentafluoroethyl-1,2,6,7,8,11,12,13,14,15,16,17-dodecahydrocyclopenta[a]phenanthren-3-one;

(8S,11R,13S,14S,17S)-17-hydroxy-13-methyl-11-{4-[(E)-2-(4-methylsulphanylphenyl)vinyl]phenyl}-17-pentafluoroethyl-1,2,6,7,8,11,12,13,14,15,16,17-dodecahydrocyclopenta[a]phenanthren-3-one;

4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzaldehyde O-benzyl oxime;

4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzaldehyde O-ethyl oxime;

4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzaldehyde O-isobutyl oxime;

1-ethyl-3-[4-((8S,11R,13S,14S,17S)-17-hydroxy-13-methyl-3-oxo-17-pentafluoroethyl-2,3,6,7,8,11,12,13,14, 15,16,17-dodecahydro-1H-cyclopenta[a]phenanthren-11-yl)benzyl]urea;

1-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]-3-isopropylurea;

1-tert-butyl-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)benzyl]urea;

1-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}-3-phenylurea;

1-(4-fluorophenyl)-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea;

1-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}-3-p-tolylurea;

1-benzyl-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea;

1-tert-butyl-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea;

1-(3,5-dimethylisoxazol-4-yl)-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea;

3-(3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)propionic acid ethyl ester;

(3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)acetic acid ethyl ester;

1-(4-chlorophenyl)-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea;

1-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}-3-(4-methoxyphenyl)urea;

4-(3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}ureido)benzoic acid ethyl ester; or 1-allyl-3-{(E)-3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]allyl}urea.

6. Process for preparing the compounds of the general formula I according to claim 1 comprising the steps of converting an epoxide of the general formula II

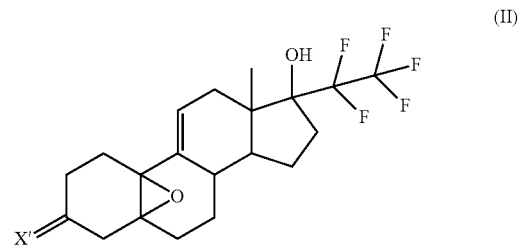

in which

X' is a $C_2$-$C_{10}$-alkylene-α,ω-dioxy group which is straight-chain or branched, in an organometallic coupling reaction into a compound of the general formula III

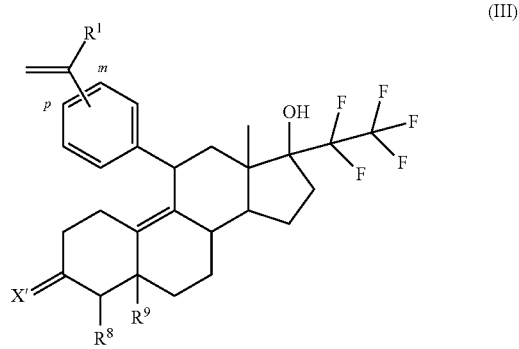

in which $R^1$ is defined as in claim 1, and X' is defined as specified herein above and $R^8$ is hydrogen, $R^9$ is a hydroxyl group, or $R^8$, $R^9$ together are a bond, and converting the compound of the general formula III to give a compound of the general formula I'

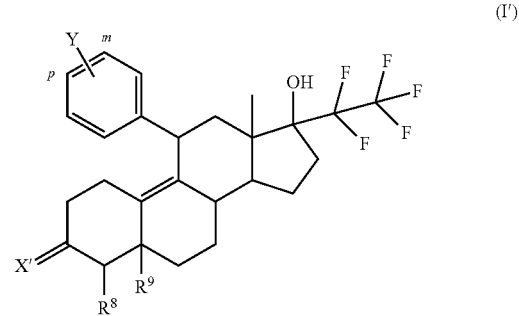

wherein Y is as defined in claim 1 and X', $R^8$ and $R^9$ is defined as specified herein above, and converting the compound of general formula I' to give a compound of the general formula I

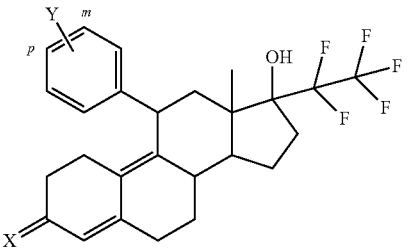

(I)

wherein X and Y are as defined in claim 1, wherein in the case that $R^8$ is hydrogen and $R^9$ is a hydroxyl group in the compound of the general formula (I'), a double bond is obtained by elimination of water, and so $R^8$ and $R^9$ together are a bond.

7. Pharmaceutical formulation comprising at least one compound according to claim 1 and a pharmaceutically suitable carrier.

8. Method of treatment of fibroids of the uterus, endometriosis, heavy menstrual bleeds, meningiomas, breast cancers, or for fertility control and emergency contraception by administering a compound according to claim 1 to a patient in need thereof.

9. Process for preparing the compounds of the general formula I according to claim 1 comprising the steps of converting an epoxide of the general formula II

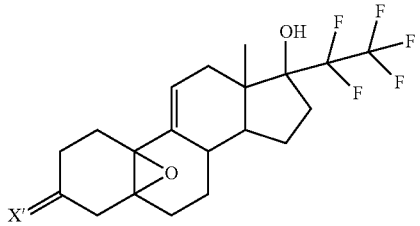

(II)

in which

X' is an oxygen atom, in an organometallic coupling reaction into a compound of the general formula III

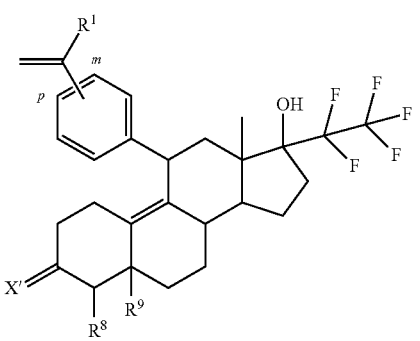

(III)

in which $R^1$ is defined as in claim 1, and X' is defined as specified herein above and $R^8$ is hydrogen, $R^9$ is a hydroxyl group, or $R^8$, $R^9$ together are a bond, and converting the compound of general formula III to give a compound of the general formula I'

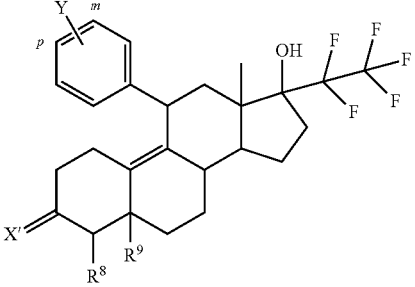

(I')

wherein Y is as defined in claim 1 and X', $R^8$ and $R^9$ is defined as specified herein above, wherein the compound of the general formula I' is a compound of the general formula I, wherein X is O, and $R^8$ and $R^9$ together are a bond;

when $R^8$ is hydrogen and $R^9$ is a hydroxyl group the process further comprises a step of converting the compound of the general formula I' into the compound of the general formula I by eliminating water to form a second bond between $R^8$ and $R^9$; and optionally converting the compound of general formula I' to the compound of general formula I, wherein X is $NOR^6$ or $NNHSO_2R^6$, wherein $R^6$ is defined as in claim 1.

10. Process for preparing the compounds of the general formula I according to claim 1 comprising the steps of converting an epoxide of the general formula II

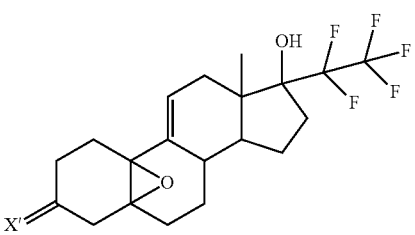

(II)

in which

X' is two alkoxy groups $OR^7$, and $R^7$ is a $C_1$-$C_4$-alkyl group in an organometallic coupling reaction into a compound of the general formula III

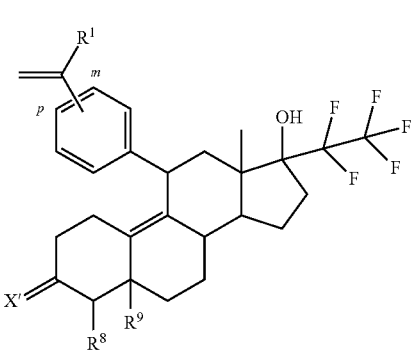

(III)

in which
R¹ is defined as in claim 1, and X' is defined as specified herein above and
R⁸ is hydrogen,
R⁹ is a hydroxyl group, or
R⁸, R⁹ together are a bond,
and converting the compound of general formula III to give a compound of the general formula I'

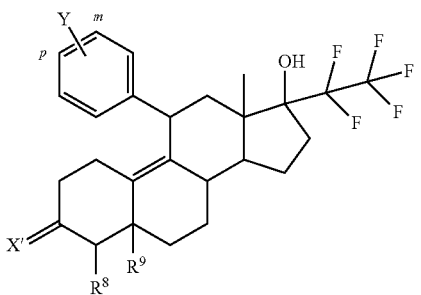

(I')

wherein Y is as defined in claim 1 and X', R⁸ and R⁹ is defined as specified herein above, and
converting the compound of general formula I' to give a compound of the general formula I

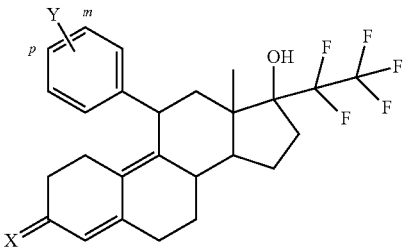

(I)

wherein X is O, and Y is defined in claim 1.

* * * * *